United States Patent
Dellinger et al.

(10) Patent No.: US 10,597,421 B2
(45) Date of Patent: Mar. 24, 2020

(54) PROTECTED MONOMER AND METHOD OF FINAL DEPROTECTION FOR RNA SYNTHESIS

(71) Applicant: Agilent Technologies, Inc., Santa Clara, CA (US)

(72) Inventors: Douglas J. Dellinger, Boulder, CO (US); Joel Myerson, Berkeley, CA (US); Agnieszka Sierzchala, Boulder, CO (US); Geraldine F. Dellinger, Boulder, CO (US); Zoltan Timar, Boulder, CO (US)

(73) Assignee: Agilent Technologies, Inc., Santa Clara, CA (US)

( * ) Notice: Subject to any disclaimer, the term of this patent is extended or adjusted under 35 U.S.C. 154(b) by 52 days.

(21) Appl. No.: 15/839,547

(22) Filed: Dec. 12, 2017

(65) Prior Publication Data

US 2018/0186826 A1   Jul. 5, 2018

Related U.S. Application Data

(60) Continuation of application No. 14/853,790, filed on Sep. 14, 2015, now Pat. No. 9,896,472, which is a division of application No. 13/531,191, filed on Jun. 22, 2012, now Pat. No. 9,273,086, which is a division of application No. 12/466,326, filed on May 14, 2009, now abandoned.

(60) Provisional application No. 61/099,131, filed on Sep. 22, 2008.

(51) Int. Cl.
| | |
|---|---|
| C07H 21/02 | (2006.01) |
| C07H 21/04 | (2006.01) |
| C07H 21/00 | (2006.01) |
| C08L 85/02 | (2006.01) |
| C07H 19/067 | (2006.01) |
| C07H 13/12 | (2006.01) |
| A61K 31/7125 | (2006.01) |
| A61K 31/712 | (2006.01) |
| C07H 19/00 | (2006.01) |
| C07H 19/167 | (2006.01) |
| C07H 23/00 | (2006.01) |
| C07H 1/00 | (2006.01) |

(52) U.S. Cl.
CPC ......... *C07H 19/067* (2013.01); *A61K 31/712* (2013.01); *A61K 31/7125* (2013.01); *C07H 1/00* (2013.01); *C07H 13/12* (2013.01); *C07H 19/00* (2013.01); *C07H 19/167* (2013.01); *C07H 21/00* (2013.01); *C07H 21/02* (2013.01); *C07H 21/04* (2013.01); *C07H 23/00* (2013.01); *C08L 85/02* (2013.01); *Y02P 20/55* (2015.11)

(58) Field of Classification Search
None
See application file for complete search history.

(56) References Cited

U.S. PATENT DOCUMENTS

| | | | |
|---|---|---|---|
| 4,426,517 A | 1/1984 | Hsiung | |
| 5,514,789 A | 5/1996 | Kempe | |
| 5,750,672 A | 5/1998 | Kempe | |
| 6,600,032 B1 | 7/2003 | Manoharan et al. | |
| 6,822,089 B1 | 11/2004 | Sanghvi et al. | |
| 8,202,983 B2 | 6/2012 | Dellinger et al. | |
| 9,273,086 B2 * | 3/2016 | Dellinger | C07H 19/00 |
| 2002/0045221 A1 | 4/2002 | Dellinger et al. | |
| 2002/0058802 A1 | 5/2002 | Dellinger et al. | |
| 2004/0116687 A1 | 6/2004 | Dellinger | |
| 2004/0158055 A1 | 8/2004 | Song et al. | |
| 2004/0230052 A1 | 11/2004 | Dellinger et al. | |
| 2005/0048496 A1 | 3/2005 | Dellinger et al. | |
| 2005/0048497 A1 | 3/2005 | Dellinger et al. | |
| 2005/0048601 A1 | 3/2005 | Dellinger et al. | |
| 2005/0049407 A1 | 3/2005 | Dellinger et al. | |
| 2005/0049411 A1 | 3/2005 | Dellinger et al. | |
| 2006/0147918 A1 | 7/2006 | Goldsborough | |
| 2006/0247430 A1 | 11/2006 | Dellinger et al. | |
| 2006/0252924 A1 | 11/2006 | Dellinger et al. | |
| 2006/0293511 A1 | 12/2006 | Dellinger | |
| 2007/0099859 A1 | 5/2007 | Dellinger et al. | |
| 2007/0100136 A1 | 5/2007 | Dellinger et al. | |
| 2007/0100137 A1 | 5/2007 | Dellinger et al. | |
| 2007/0100138 A1 | 5/2007 | Dellinger et al. | |
| 2007/0224602 A1 | 9/2007 | Dellinger et al. | |
| 2007/0224603 A1 | 9/2007 | Dellinger et al. | |
| 2008/0076913 A1 | 3/2008 | Dellinger et al. | |
| 2008/0146787 A1 | 6/2008 | Timar et al. | |

(Continued)

FOREIGN PATENT DOCUMENTS

| | | |
|---|---|---|
| EP | 0977767 B1 | 9/2007 |
| WO | WO0173095 A2 | 10/2001 |
| WO | WO2008141248 A2 | 11/2008 |

OTHER PUBLICATIONS

Oba, et al., "Radical-Based Transformation of Vicinal Diols to Olefins via Thioxocarbamate Derivatives: a simple approach to 2',3'-didehydro-2',3'-dideoxynucleosides", Tetrahedron Letters, 2003, pp. 4027-4209, vol. 44, No. 21.

(Continued)

*Primary Examiner* — Eric Olson

(57) ABSTRACT

A method of deprotecting a solid support bound polynucleotide comprising at least one 2'-protected ribonucleotide in which a step of contacting the polynucleotide with a composition comprising a diamine is performed under conditions sufficient to deprotect and cleave the polynucleotide which remains retained on the solid support.

17 Claims, 5 Drawing Sheets

Specification includes a Sequence Listing.

(56) References Cited

U.S. PATENT DOCUMENTS

2009/0209479 A1  8/2009  Dellinger et al.
2012/0238737 A1  9/2012  Dellinger et al.
2012/0289691 A1  11/2012 Dellinger et al.

OTHER PUBLICATIONS

Reese et al., "The H-Phosphate Approach to the Synthesis of Oligonucleotides and Their Phosphorothioate Analogues in Solution", JCS, Perkin Transactions, 1999, pp. 1477-1486, vol. 1.
Velazquez, "Stereospecific Synthesis and NMR conformational Studies of g-Butyrolactones of Nucleosides as Chiral Synthons for the Preparation of 2'-C- and 3'-C-Branched-Chain Nucleosides", Journal of Organic Chemistry, 1994, pp. 7661-7670, vol. 59.
Aldrich, "The Sigma-Aldrich Family Chemical Catalog", 2005, 3 pages.
Sinha et al., "Synthesis of Oligodeoxynucleoside Methylphosphonates Utilizing the tert- Butylphenoxyacetyl Group for Exocyclic Amine Protection", Nucleic Acids Research, 1994, pp. 3119-3123, vol. 22, No. 15.
Sundaram et al., "Synthesis and Characterization of the Native Anticodon Domain of *E coli* tRNAlys: Simultaneous Incorporation of Modified Nucleosides Mnm5s2u, t6A, and Pseudouridine Using Phosphoramidite Chemistry", Journal of Organic Chemistry, 2000, pp. 5609-5614, vol. 65.
Nair et al., "Synthetic Approaches to New Doubly Modified Nucleosides: Congeners of cordycepin and related 2'- deoxyadenosine", Tetrahedron, Elsevier Science Publisher, 1991, pp. 365-382, vol. 47, No. 3.
Communication pursuant to Article 94(3) EPC dated Jun. 24, 2005 for EP Application No. 09815409.9, 5 pages.
Communication Pursuant to Article 94(3) dated Mar. 29, 2016 for EP Application No. 09815409.9, 4 pages.
Extended European Search Report and Search Opinion received for dated Nov. 16, 2012 for EP Application No. 09815409.9, 6 pages.
Non-final Office Action for U.S. Appl. No. 13/339,082 dated Jul. 1, 2014, 13 pages.
Un-published U.S. Appl. No. 12/118,655, May 9, 2008, 99 pages.
International Search Report dated May 18, 2010 for PCT Application No. PCT/US2009/057922, 5pages.

\* cited by examiner

PROTECTED MONOMER AND METHOD OF FINAL DEPROTECTION FOR RNA SYNTHESIS

CROSS REFERENCE TO RELATED APPLICATION

This is a continuation application of U.S. patent application Ser. No. 14/853,790, filed on Sep. 14, 2015, which is a divisional application of U.S. patent application Ser. No. 13/531,191, filed on Jun. 22, 2012, now U.S. Pat. No. 9,273,086, which is a divisional application of application Ser. No. 12/466,326, filed on May 14, 2009, now abandoned, which claims the benefit of U.S. provisional application Ser. No. 61/099,131, filed on Sep. 22, 2008. This application claims the benefits of these prior applications and hereby incorporates disclosures of these prior applications by reference herein in their entireties.

BACKGROUND

Chemical synthesis of RNA is a more difficult task than chemical synthesis of DNA, because the 2'-hydroxyl group in the ribose has to be protected during chemical synthesis. The close proximity of a protected 2'-hydroxyl to the internucleotide phosphate may present problems, both in terms of formation of the internucleotide linkage and in the removal of the 2'-protecting group once the oligoribonucleotide is synthesized. In addition, the internucleotide bond in RNA is less stable than that in DNA.

Until recently, the typical approach to RNA synthesis utilized ribonucleotide monomers in which the 5'-hydroxyl group was protected by the acid-labile dimethoxytrityl (DMT) protecting group, which can be removed under acidic conditions after coupling of the monomer to the growing oligoribonucleotide. Various acid-stable protecting groups have been placed on the 2'-hydroxyl to prevent isomerization and cleavage of the internucleotide bond during the acid deprotection step, for example the tert-butyldimethylsilyl group, known as TBDMS (Ogilvie et al., 1979). The use of TBDMS as 2'-protecting group dominated the previously small market for RNA chemical synthesis for a very long time (Usman et al., 1987; Ogilvie et al., 1988).

However, oligoribonucleotide syntheses carried out using TBDMS are by no means satisfactory and may produce RNA products of poor quality. In some cases the coupling efficiency of these monomers is decreased due to steric hindrance of the 2'-TBDMS protecting group, which may affect the yield and purity of the full-length product, and also limit the length of the oligoribonucleotide that can be achieved by this method. Furthermore, in some cases, the synthesis of the monomer (e.g., 5'-O-DMT-2'-O-TBDMS-ribo-3'-O-(beta-cyanoethyl-N,N-diisopropyl)phosphoramidite) can be both challenging and costly due to the non regiospecific introduction of the TBDMS group on the 2'-hydroxyl and to the migration of the silyl group from the 2' to the 3' position, that occurs during subsequent steps of the synthesis of the monomer.

The demand for synthetic RNA has increased in the past decade, largely due to the discovery of RNA interference. To meet this growing need, it is desirable to develop improved RNA synthesis schemes, particularly 2'-protecting groups that can be introduced at low cost in high yield, along with stream-lined deprotection methods.

SUMMARY

Ribonucleotide monomers that are protected by a thionocarbamate protecting group are provided, as well as a method for making a polynucleotide that uses the same. In addition, a polynucleotide that comprises a thionocarbamate protected ribonucleotide residue is provided. Also provided is a polynucleotide synthesis method and a composition comprising a diamine reagent to deprotect a protected polynucleotide comprising a ribonucleotide residue.

Aspects of this disclosure relate to the use of a diamine composition (e.g., a composition comprising 1,2-diaminoethane or a substituted version thereof) for the deprotection of synthetic RNA molecules under conditions that in certain cases do not lead to significant cleavage or isomerization of the internucleotide bond, where significant cleavage or isomerization of an RNA molecule decreases the yield, or make it difficult to isolate or purify. Also described are methods for on-column deprotection of RNA molecules and polynucleotides containing a protected ribonucleotide and the automated final deprotection of RNA molecules. Further aspects of this disclosure relate to the simultaneous deprotection of base-labile 2'-hydroxyl protecting group moieties and the nucleobase exocyclic amine protecting group moieties in a single step. Some aspects of the disclosure relate to one pot deprotection of base-labile 2'-hydroxyl protecting group moieties, the nucleobase exocyclic amine protecting group moieties, and the phosphorus protecting group moiety, where one pot deprotection can be done using: a) a single deprotection reagent (e.g., a diamine composition) that deprotects the above protecting groups simultaneously, or b) multiple deprotection agents that deprotect the above protecting groups simultaneously or in series without the need to remove a prior deprotection agent and its reaction products from the deprotection reaction. Additional aspects include one pot deprotection of base-labile 2'-hydroxyl protecting group moieties, the nucleobase exocyclic amine protecting group moieties, the phosphorus protecting group moiety, and cleavage of a solid support linker. Another aspect is solid support cleavage simultaneously with cleavage of the 2'-hydroxyl protecting group under conditions that retain the deprotected RNA product on the column. Some aspects of the disclosure include 2' protected nucleoside or nucleotide monomers that are protected at the 2' site with thionocarbamate protecting groups and can be removed simultaneously with the nucleobase exocyclic amine moieties. In further aspects 2'-thionocarbamate protecting groups can be removed simultaneously with cleavage of a solid support linking group or simultaneously with cleavage of a solid support linking group and cleavage of protecting groups on the nucleobase exocyclic amine moieties. Additional aspects of the disclosure include a diamine composition that deprotects both 2'-thionocarbamate protecting groups and nucleobase exocyclic amine protecting groups and also cleaves polynucleotide from a solid support while the polynucleotide remains adsorbed to solid support and is not eluted with the deprotection composition. Further additional aspects of the disclosure include the protecting groups of the disclosure as well as methods of synthesizing nucleic acids using the protecting groups of the disclosure and the deprotecting of synthetic RNA.

Provided herein is a compound of the structure of Formula (I):

wherein:

B$^P$ is a protected or unprotected heterocycle; and

R$^1$ and R$^2$ are independently selected from hydrogen, a protecting group, and a group comprising a phosphorus; and PG is a thionocarbamate protecting group.

In certain embodiments, the compound is of the structure of Formula (I) wherein:

B$^P$ is a protected or unprotected heterocycle; and one of R$^1$ and R$^2$ is selected from a phosphoramidite group and a H-phosphonate group; and one of R$^1$ and R$^2$ is a protecting group; and PG is a thionocarbamate protecting group.

In certain embodiments, the compound is of the structure of Formula (I) wherein:

B$^P$ is a protected or unprotected heterocycle; and one of R$^1$ and R$^2$ is selected from a phosphoramidite group and a H-phosphonate group; and one of R$^1$ and R$^2$ is a protecting group; and PG is a thionocarbamate protecting group selected from one of the structures:

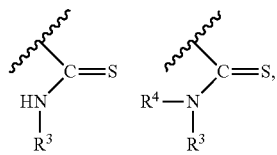

wherein:

R$^3$, R$^4$ and R$^5$ are independently selected from a hydrocarbyl, a substituted hydrocarbyl, an aryl, and a substituted aryl, and wherein optionally R$^4$ and R$^5$ can be cyclically linked.

In certain embodiments, the compound is of the structure of Formula (I) wherein:

B$^P$ is a protected or unprotected heterocycle; and one of R$^1$ and R$^2$ is selected from a phosphoramidite group and a H-phosphonate group; and one of R$^1$ and R$^2$ is a protecting group; and PG is a thionocarbamate protecting group selected from one of the structures:

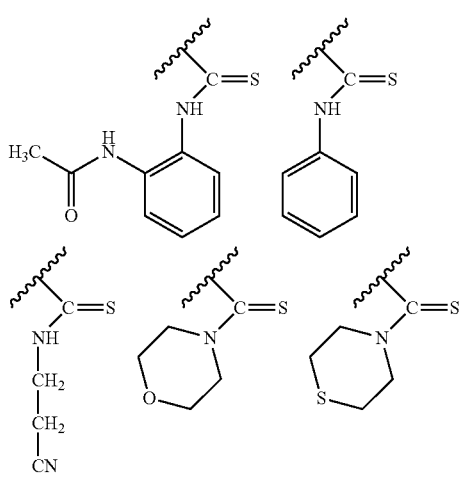

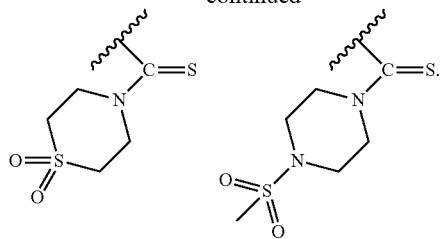

In certain embodiments, the compound is of the structure of Formula (I) wherein:

B$^P$ is a protected or unprotected heterocycle; and one of R$^1$ and R$^2$ is selected from a phosphoramidite group and a H-phosphonate group; and one of R$^1$ and R$^2$ is a protecting group; and PG is a thionocarbamate protecting group of the structure:

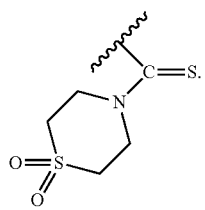 [SMILES: *C(=S)N1CCS(=O)(=O)CC1]

In certain embodiments, the compound is of the structure of Formula (I) wherein:

B$^P$ is selected from the group consisting of U, N$^6$-benzoyl-A, N$^6$-isobutyryl-A, N$^6$—(N,N)-dimethylacetamidine-A, N$^6$—(N,N)-dibutylformamidine-A, N$^6$-phenoxyacetyl-A, N$^6$-4-tert-butylphenoxyacetyl-A, N$^4$-acetyl-C, N$^4$-isobutyryl-C, N$^4$-phenoxyacetyl-C, N$^4$-4-tert-butylphenoxyacetyl-C, N$^2$-isobutyryl-G, N$^2$—(N,N)-dibutylformamidine-G, N$^2$—(N,N)-dimethylformamidine-G, N$^2$-phenoxyacetyl-G and N$^2$-4-tert-butylphenoxyacetyl-G; and R$^1$ is DMT;

R$^2$ is beta-cyanoethyl-N,N-diisopropylphosphoramidite; and

PG is a thionocarbamate protecting group of the structure:

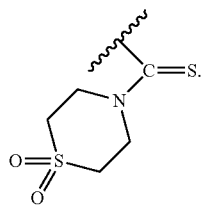 [SMILES: *C(=S)N1CCS(=O)(=O)CC1]

A method of synthesizing a polynucleotide comprising at least one ribonucleotide residue is provided. In certain embodiments the method comprises contacting a nucleotide residue or a nucleoside monomer having an unprotected hydroxyl group with a compound of the structure of Formula (I) wherein:

B$^P$ is a protected or unprotected heterocycle; and one of R$^1$ and R$^2$ is selected from a phosphoramidite group and a H-phosphonate group; and one of R$^1$ and R$^2$ is a protecting group; and PG is a thionocarbamate protecting group;

under conditions sufficient to covalently bond the compound to the nucleotide residue or the nucleoside monomer and produce the polynucleotide.

In particular embodiments the method comprises contacting a nucleotide residue or a nucleoside monomer having an unprotected hydroxyl group with the compound of the structure of Formula (I) wherein:

$B^P$ is a protected or unprotected heterocycle; and
one of $R^1$ and $R^2$ is selected from a phosphoramidite group and a H-phosphonate group; and
one of $R^1$ and $R^2$ is a protecting group; and
PG is a thionocarbamate protecting group;
under conditions sufficient to covalently bond the compound to the nucleotide residue or the nucleoside monomer and produce the polynucleotide; and
further comprises contacting the polynucleotide with a composition comprising a sulfurization agent to produce an oxidized polynucleotide.

In particular embodiments the method comprises contacting a nucleotide residue or a nucleoside monomer having an unprotected hydroxyl group with the compound of the structure of Formula (I) wherein:

$B^P$ is a protected or unprotected heterocycle; and
one of $R^1$ and $R^2$ is selected from a phosphoramidite group and a H-phosphonate group; and
one of $R^1$ and $R^2$ is a protecting group; and
PG is a thionocarbamate protecting group;
under conditions sufficient to covalently bond the compound to the nucleotide residue or the nucleoside monomer and produce the polynucleotide; and
wherein the nucleotide residue or the nucleoside monomer is bound to a solid support. In particular embodiments the solid support is selected from a CPG support and a polystyrene support. In particular embodiments the solid support is selected from a bead and an array substrate.

In particular embodiments the method comprises contacting a nucleotide residue or a nucleoside monomer having an unprotected hydroxyl group with the compound of the structure of Formula (I) wherein:

$B^P$ is a protected or unprotected heterocycle; and
one of $R^1$ and $R^2$ is selected from a phosphoramidite group and a H-phosphonate group; and
one of $R^1$ and $R^2$ is a protecting group; and
PG is a thionocarbamate protecting group;
under conditions sufficient to covalently bond the compound to the nucleotide residue or the nucleoside monomer and produce the polynucleotide; and
wherein the polynucleotide is cleaved from a solid support to produce a free polynucleotide. In particular embodiments the free polynucleotide is retained on the solid support. In particular embodiments the free polynucleotide is separated from the solid support, for example dissolved into a solvent, an aqueous solution, or mixtures thereof. In particular embodiments the free polynucleotide may be chemically modified to produce a modified polynucleotide. In some cases the modified polynucleotide may still be retained on the solid support, in other cases the modified polynucleotide may be separate from the solid support, for example in the solution phase.

A polynucleotide product produced by the above mentioned synthesis method is provided.

A polynucleotide comprising a ribonucleotide residue is provided. In some embodiments the polynucleotide comprises the structure of Formula (II):

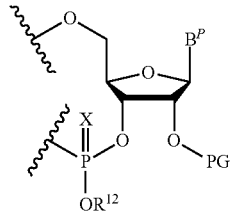

(II)

wherein:
$B^P$ is a protected or unprotected heterocycle; and
$R^{12}$ is selected from hydrogen, a hydrocarbyl, a substituted hydrocarbyl, an aryl, and a substituted aryl; and
X is O or S; and
PG is a thionocarbamate protecting group.

In some embodiments the polynucleotide comprises the structure of Formula (II):
wherein:
$B^P$ is a protected or unprotected heterocycle; and
$R^{12}$ is selected from hydrogen, a hydrocarbyl, a substituted hydrocarbyl, an aryl, and a substituted aryl; and
X is O or S; and
PG is a thionocarbamate protecting group selected from one of the structures:

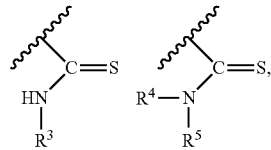

wherein:
$R^3$, $R^4$ and $R^5$ are independently selected from a hydrocarbyl, a substituted hydrocarbyl, an aryl, and a substituted aryl, and wherein optionally $R^4$ and $R^5$ can be cyclically linked.

In some embodiments the polynucleotide comprises the structure of Formula (II) wherein:
$B^P$ is a protected or unprotected heterocycle; and
$R^{12}$ is selected from hydrogen, a hydrocarbyl, a substituted hydrocarbyl, an aryl, and a substituted aryl; and
X is O or S; and
PG is a thionocarbamate protecting group selected from one of the structures:

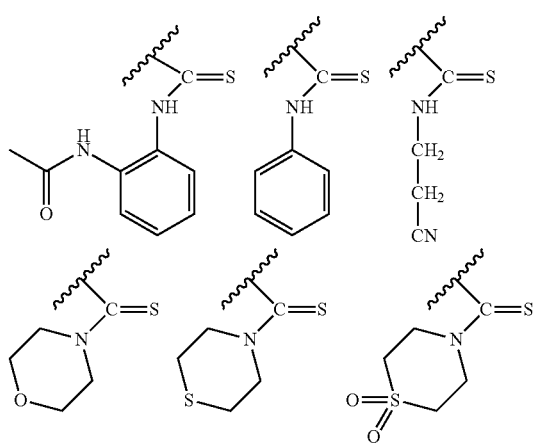

-continued

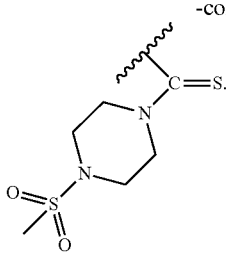

In some embodiments the polynucleotide comprises the structure of Formula (II) wherein:

$B^P$ is selected from the group consisting of U, $N^6$-benzoyl-A, $N^6$-isobutyryl-A, $N^6$—(N,N)-dimethylacetamidine-A, $N^6$—(N,N)-dibutylformamidine-A, $N^6$-phenoxyacetyl-A, $N^6$-4-tert-butylphenoxyacetyl-A, $N^4$-acetyl-C, $N^4$-isobutyryl-C, $N^4$-phenoxyacetyl-C, $N^4$-4-tert-butylphenoxyacetyl-C, $N^2$-isobutyryl-G, $N^2$—(N,N)-dibutylformamidine-G, $N^2$—(N,N)-dimethylformamidine-G, $N^2$-phenoxyacetyl-G and $N^2$-4-tert-butylphenoxyacetyl-G; and $R^{12}$ is selected from beta-cyanoethyl, and methyl; and X is O or S; and PG is a thionocarbamate protecting group of the structure:

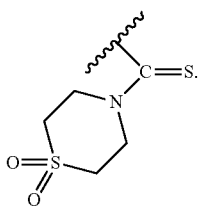

A method of deprotecting a solid support bound polynucleotide comprising at least one 2'-protected ribonucleotide residue is provided, where the residue is not a 2'-ester protected ribonucleotide residue, i.e., a ribonucleotide residue that is protected at the 2'-hydroxyl with an ester protecting group. In certain embodiments the method comprises:

contacting the polynucleotide with a composition comprising a diamine under conditions sufficient to deprotect the 2'-protected ribonucleotide residue.

In certain embodiments the method comprises:

contacting the polynucleotide with a composition comprising a diamine under conditions sufficient to deprotect the 2'-protected ribonucleotide residue; wherein the 2'-protected ribonucleotide residue comprises the structure:

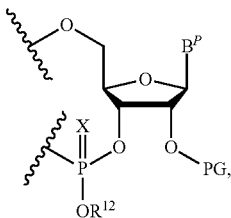

wherein:

$B^P$ is a protected or unprotected heterocycle; and $R^{12}$ is a protecting group selected from a hydrocarbyl, a substituted hydrocarbyl, an aryl, and a substituted aryl; and X is O or S; and PG is a thionocarbamate protecting group.

In particular embodiments of the above described deprotection method the thionocarbamate protecting group (PG) is selected from one of the structures:

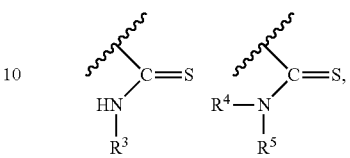

wherein:

$R^3$, $R^4$ and $R^5$ are independently selected from a hydrocarbyl, a substituted hydrocarbyl, an aryl, and a substituted aryl, and wherein optionally $R^4$ and $R^5$ can be cyclically linked.

In particular embodiments of the above mentioned deprotection method the thionocarbamate protecting group (PG) is selected from one of the structures:

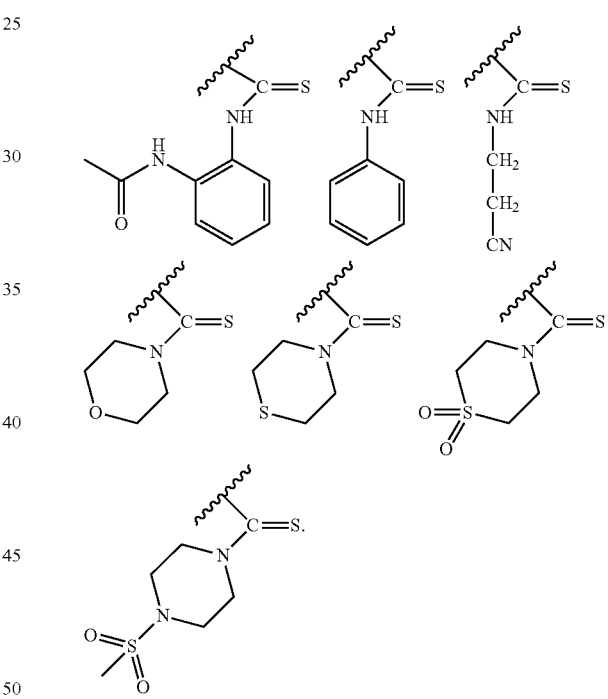

In particular embodiments of the above mentioned deprotection method the 2'-protected ribonucleotide residue comprises the structure:

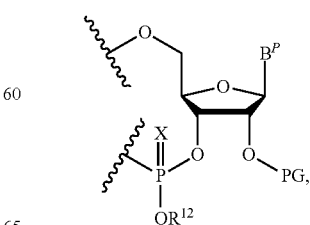

wherein:

B$^P$ is selected from the group consisting of U, N$^6$-benzoyl-A, N$^6$-isobutyryl-A, N$^6$—(N,N)-dimethylacetamidine-A, N$^6$—(N,N)-dibutylformamidine-A, N$^6$-phenoxyacetyl-A, N$^6$-4-tert-butylphenoxyacetyl-A, N$^4$-acetyl-C, N$^4$-isobutyryl-C, N$^4$-phenoxyacetyl-C, N$^4$-4-tert-butylphenoxyacetyl-C, N$^2$-isobutyryl-G, N$^2$—(N,N)-dibutylformamidine-G, N$^2$—(N,N)-dimethylformamidine-G, N$^2$-phenoxyacetyl-G and N$^2$-4-tert-butylphenoxyacetyl-G; and R$^{12}$ is selected from beta-cyanoethyl, and methyl; and X is O or S; and PG is a thionocarbamate protecting group of the structure:

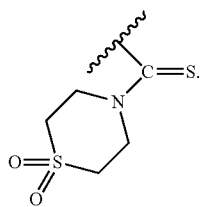

In certain embodiments of the deprotection method described above the diamine reagent comprises two primary amino groups connected by a linker of about 2 to 12 atoms in length. In particular embodiments the linker is of about 2 to 6 atoms in length.

In certain embodiments of the deprotection method described above the diamine is selected from 1,2-diaminoethane, 1,2-diaminopropane, 1,3-diaminopropane, 1,4-diaminobutane, 2,2'-diaminodiethylamine, and substituted versions thereof.

In certain embodiments of the above mentioned deprotection method the diamine is 1,2-diaminoethane.

In certain embodiments of the deprotection method described above the composition comprises at least 50% by volume 1,2-diaminoethane.

In certain embodiments of the deprotection method described above, the composition comprises 1,2-diaminoethane and a solvent.

A method is provided. In certain embodiments the method comprises:

(a) contacting a solid support bound polynucleotide comprising:
a ribonucleotide residue comprising a 2'-protecting group, a phosphate protecting group, and optionally a nucleobase protecting group;
with a first composition comprising a phosphate deprotection reagent, to remove the phosphate protecting group and produce a first deprotected polynucleotide that remains bound to the solid support;

(b) contacting the first deprotected polynucleotide with a second composition comprising a diamine to remove the 2'-protecting group and remove the nucleobase protecting group, if present, to produce a second deprotected polynucleotide; and (c) or (d) wherein:
(c) comprises simultaneously cleaving the second deprotected polynucleotide from the solid support; and
(d) comprises contacting the second deprotected polynucleotide with a third composition comprising a linker cleaving reagent to cleave the second deprotected polynucleotide from the solid support, to produce a deprotected, cleaved polynucleotide.

In particular embodiments of the method described above the phosphate protecting group is a 2-cyanoethyl group or a methyl group. In particular embodiments of the method above the phosphate deprotection reagent is selected from diethylamine, t-butylamine, diaza(1,3)bicyclo[5.4.0]undecane (DBU), thiophenol and disodium 2-carbamoyl-2-cyanoethylene-1, 1-dithiolate; and the diamine is 1,2-diaminoethane.

A method of deprotecting a polynucleotide comprising a nucleobase protecting group; and a ribonucleotide residue comprising a 2'-protecting group; selected from tert-butyldimethylsilyl (TBDMS), triisopropylsilyloxymethyl (TOM) and 2'-O-bis(2-acetoxyethoxy)methyl (ACE); is provided. In certain embodiments the method comprises:

(a) contacting the polynucleotide with a first composition comprising a 2'-deprotection reagent, under conditions sufficient to remove the 2'-protecting group and produce a first deprotected polynucleotide;

(b) contacting the first deprotected polynucleotide with a second composition comprising a diamine, under conditions sufficient to remove the nucleobase protecting group and produce a fully deprotected polynucleotide.

A method of deprotecting a solid support bound polynucleotide comprising a phosphate protecting group, a nucleobase protecting group; and a ribonucleotide residue comprising 2'-protecting group is provided. In certain embodiments the method comprises:

(a) contacting the polynucleotide with a first composition comprising a phosphate deprotection reagent, under conditions sufficient to remove the phosphate protecting group and produce a first deprotected polynucleotide;

(b) contacting the first deprotected polynucleotide with a second composition comprising a 2'-deprotection reagent under conditions sufficient to remove the 2'-protecting group and produce a second deprotected polynucleotide;

(c) contacting the second deprotected polynucleotide with a third composition comprising a diamine, under conditions sufficient to remove the nucleobase protecting group and produce a fully deprotected polynucleotide.

In particular embodiments of the method described above the 2'-protecting group is selected from tert-butyldimethylsilyl (TBDMS), triisopropylsilyloxymethyl (TOM) and 2'-O-bis(2-acetoxyethoxy)methyl (ACE).

A method of deprotecting a solid support bound polynucleotide comprising a nucleobase protecting group; and a ribonucleotide residue comprising a thionocarbamate protecting group is provided. In certain embodiments the method comprises:

(a) contacting said polynucleotide with a composition comprising a diamine, under conditions sufficient to remove the protecting groups and cleave the polynucleotide from the solid support, and produce a cleaved polynucleotide; wherein the cleaved polynucleotide is retained on the solid support;

(b) washing the solid support and cleaved polynucleotide;

(c) eluting the cleaved polynucleotide from the solid support.

In certain embodiments retention of the cleaved polynucleotide on the solid support allows for the cleaved polynucleotide to be easily separated from the composition and the deprotected protecting group products, for example by one or more wash steps. The composition may also be removed from the cleaved polynucleotide by a drying, evaporation, vacuum step, or the like.

A polynucleotide produced by the above method of deprotecting a solid support bound polynucleotide is provided.

A kit for deprotecting a polynucleotide comprising a 2' protected ribonucleotide residue is provided. In certain embodiments the kit comprises a composition comprising a diamine. In particular embodiments the kit comprises:

a composition comprising 1,2-diaminoethane, or derivatives thereof.

A protected nucleoside monomer is provided. In certain embodiments the protected nucleoside monomer is of the structure:

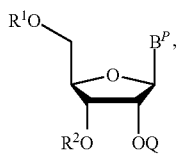

wherein:
B$^P$ is a protected or unprotected heterocycle; and
R$^1$ and R$^2$ are each a hydroxyl protecting group, wherein optionally R$^1$ and R$^2$ can be cyclically linked; and
Q is a thionocarbamate protecting group.

In certain embodiments the protected nucleoside monomer is selected from one of the structures:

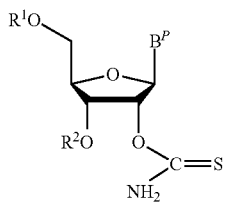 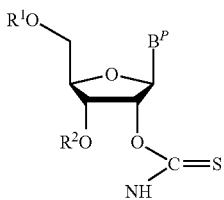

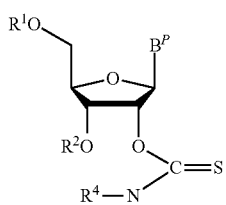 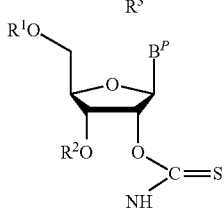

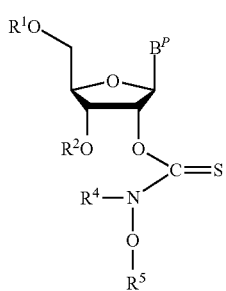

wherein:
B$^P$ is a protected or unprotected heterocycle; and
R$^1$ and R$^2$ are each a hydroxyl protecting group, wherein optionally R$^1$ and R$^2$ can be cyclically linked; and
R$_3$, R$_4$ and R$_5$ are independently selected from a hydrocarbyl, a substituted hydrocarbyl, an aryl, and a substituted aryl, and wherein optionally R$_4$ and R$_5$ can be cyclically linked.

In certain embodiments the protected nucleoside monomer is selected from one of the structures:

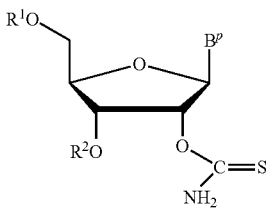

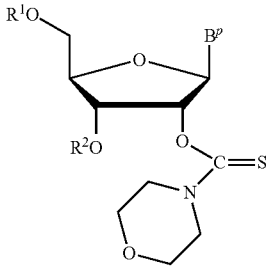

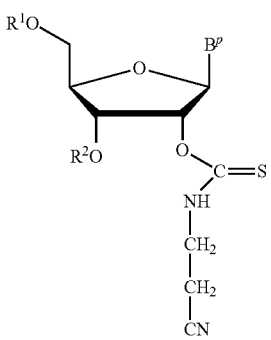

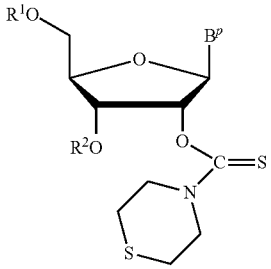

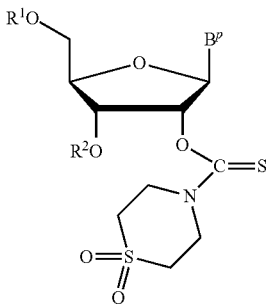

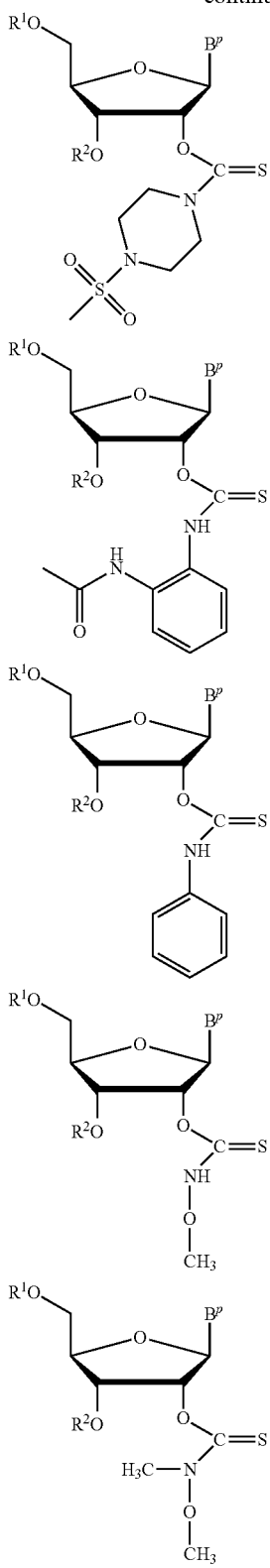

wherein:

B$^P$ is a protected or unprotected heterocycle; and

R$^1$ and R$^2$ are each a hydroxyl protecting group, wherein optionally R$^1$ and R$^2$ can be cyclically linked.

In particular embodiments of the protected nucleoside monomer, R$^1$ and R$^2$ are cyclically linked by a disiloxane bidentate protecting group.

DEFINITIONS

Figure 1:
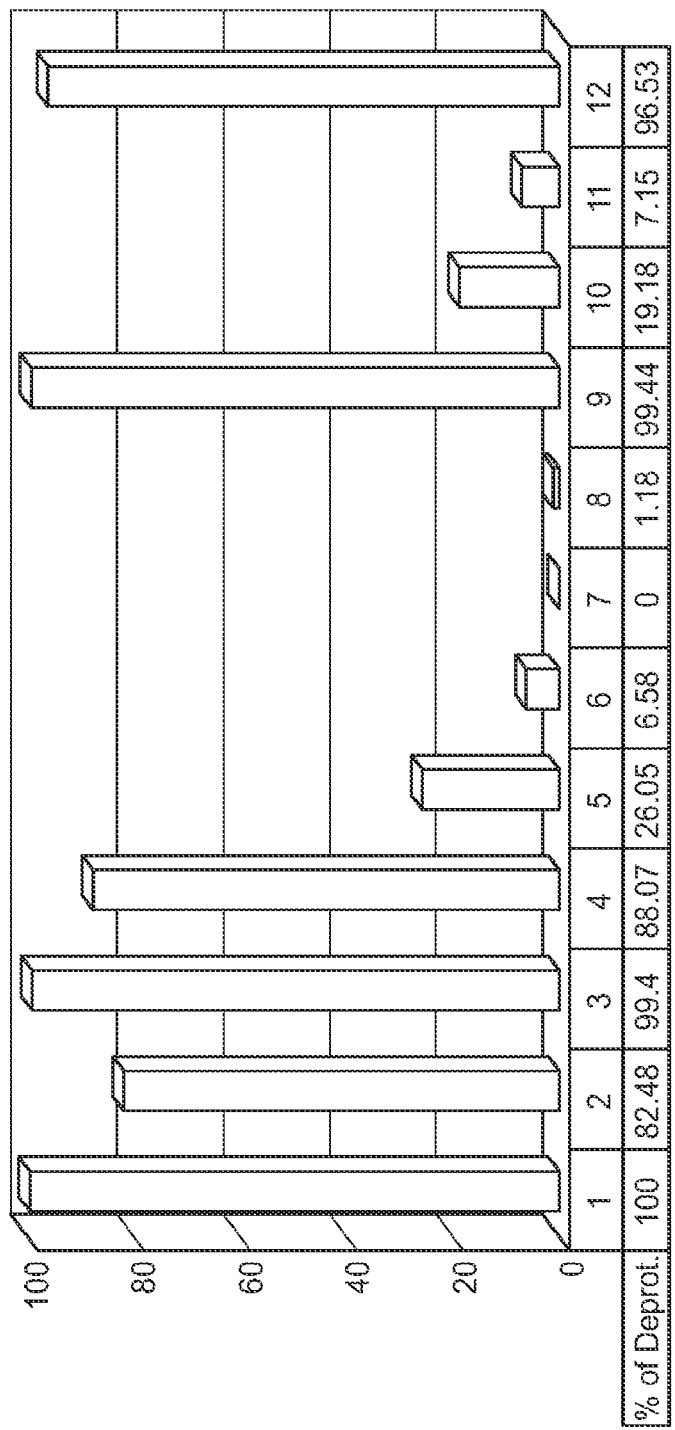
FIG. 1 is a graph showing the amount of deprotection of U(2'TC)T$_{15}$~succ~CPG with various diamine compositions (1-12), where U(2'TC) indicates a U residue protected with a 2'-thionocarbamate protecting group.

The terms used in the disclosure of this application are defined as follows unless otherwise indicated.

A "nucleotide" contains a phosphorus containing moiety (e.g., a phosphate, a phosphoramidite, or an H-phosphonate), a sugar moiety and a heterocyclic base moiety, or an analog of the same. A nucleotide may optionally also contain one or more other groups (e.g., protecting groups or activating groups) independently attached to any moiety(s) of a nucleotide.

A "ribonucleotide" is a nucleotide that contains a ribose sugar moiety, including modified ribose sugar moieties.

A "nucleotide monomer" is a free nucleotide which is not part of a polynucleotide. A nucleotide monomer may also contain such groups as may be necessary for an intended use of the nucleotide monomer. For example, a nucleotide monomer may comprise an activating group (e.g. a phosphoramidite or H-phosphonate group) and one or more protecting groups, if the nucleotide monomer is to be used as a building block for synthesis of a polynucleotide.

A nucleotide monomer may be reacted with a terminal nucleotide residue to produce a polynucleotide.

A "nucleotide residue" is a nucleotide that is a single residue of a polynucleotide. A nucleotide monomer once incorporated into a polynucleotide, becomes a nucleotide residue. A terminal nucleotide residue of a polynucleotide may be bound to a solid support indirectly via the other end of the polynucleotide of which it is a part, e.g., via a linker, or it may be bound to a solid support directly, e.g., when it is the first nucleotide residue of the oligonucleotide chain, as for example can be done in the synthesis of an array.

A "nucleoside" includes a sugar moiety and a heterocyclic base moiety, or an analog of the same. Unless otherwise indicated (e.g. in the case of a "nucleoside phosphoramidite") a nucleoside does not include a phosphorus containing moiety (e.g., a phosphate, a phosphoramidite, or an H-phosphonate). A nucleoside may optionally also contain one or more other groups (e.g. a hydroxyl protecting group, a bidentate diol protecting group, or a heterocyclic base protecting group) independently attached to any moiety(s) of a nucleoside.

A "nucleoside monomer" is a nucleoside which is not part of a polynucleotide. A nucleoside monomer may also contain such groups as may be necessary for an intended use of the nucleoside monomer. A nucleoside monomer may be free or attached to a solid support. For example, a nucleoside monomer having a heterocyclic base protecting group and one or more hydroxyl protecting groups may be a synthetic intermediate in the synthesis of a nucleotide monomer. For example, a nucleoside monomer may be attached to a solid support for the synthesis of a polynucleotide.

The terms "nucleoside" and "nucleotide" are intended to include those moieties that contain not only the known purine and pyrimidine bases, e.g. adenine (A), thymine (T), cytosine (C), guanine (G), or uracil (U), but also other heterocyclic bases or nucleobases that have been modified. Such modifications include methylated purines or pyrimidines, acylated purines or pyrimidines, alkylated riboses or other heterocycles. Such modifications include, e.g., diaminopurine and its derivatives, inosine and its derivatives, alkylated purines or pyrimidines, acylated purines or pyrimidines thiolated purines or pyrimidines, and the like, or the addition of a protecting group such as acetyl, difluoroacetyl, trifluoroacetyl, isobutyryl, benzoyl, 9-fluorenylmethoxycarbonyl, phenoxyacetyl, dimethylformamidine, dibutylformamidine, N,N-diphenyl carbamate, substituted thiourea or the like. The purine or pyrimidine base may also be an analog of the foregoing; suitable analogs will be known to those skilled in the art and are described in the pertinent texts and literature. Common analogs include, but are not limited to, 1-methyladenine, 2-methyladenine, N6-methyladenine, N6-isopentyladenine, 2-methylthio-N6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine and 2,6-diaminopurine.

In addition, the terms "nucleoside" and "nucleotide" include those moieties that contain not only conventional ribose and deoxyribose sugars and conventional stereoisomers, but other sugars as well, including L enantiomers and alpha anomers. Modified nucleosides or nucleotides also include modifications on the sugar moiety, e.g., wherein one or more of the hydroxyl groups are replaced with halogen atoms or aliphatic groups, or are functionalized as ethers, amines, or the like. "Analogues" refer to molecules having structural features that are recognized in the literature as being mimetics, derivatives, having analogous structures, or other like terms, and include, for example, polynucleotides or oligonucleotides incorporating non-natural (not usually occurring in nature) nucleotides, unnatural nucleotide mimetics such as 2'-modified nucleosides including but not limited to 2'-fluoro, 2'-O-alkyl, O-alkylamino, O-alkylalkoxy, protected O-alkylamino, O-alkylaminoalkyl, O-alkyl imidazole, and polyethers of the formula (O-alkyl)m such as linear and cyclic polyethylene glycols (PEGs), and (PEG)-containing groups, locked nucleic acids (LNA), peptide nucleic acids (PNA), oligomeric nucleoside phosphonates, and any polynucleotide that has added substituent groups, such as protecting groups or linking groups.

An "internucleotide bond" or "nucleotide bond" refers to a chemical linkage between two nucleoside moieties, such as the phosphodiester linkage in nucleic acids found in nature, or linkages well known from the art of synthesis of nucleic acids and nucleic acid analogues. An internucleotide bond may include a phospho or phosphite group, and may include linkages where one or more oxygen atoms of the phospho or phosphite group are either modified with a substituent or replaced with another atom, e.g., a sulfur atom, or the nitrogen atom of a mono- or di-alkyl amino group, such as phosphite, phosphonate, H-phosphonate, phosphoramidate, phosphorothioate, and/or phosphorodithioate linkages.

A "polynucleotide", "oligonucleotide" or a "nucleic acid" refers to a compound containing a plurality of nucleoside moiety subunits or nucleoside residues that are linked by internucleotide bonds. As such it also refers to a compound containing a plurality of nucleotide moiety subunits or nucleotide residues.

A "group" includes both substituted and unsubstituted forms. Substituents of interest include one or more lower alkyl, amino, imino, amido, alkylamino, arylamino, alkoxy, aryloxy, thio, alkylthio, arylthio, or aryl, or alkyl; aryl, alkoxy, thioalkyl, hydroxyl, amino, amido, sulfonyl, thio, mercapto, imino, halo, cyano, nitro, nitroso, azido, carboxy, sulfide, sulfone, sulfoxy, phosphoryl, silyl, silyloxy, and boronyl, or optionally substituted on one or more available carbon atoms with a nonhydrocarbyl substituent such as cyano, nitro, halogen, hydroxyl, sulfonic acid, sulfate, phosphonic acid, phosphate, phosphonate, or the like. Any substituents are chosen so as not to substantially adversely affect reaction yield (for example, not lower it by more than 20% (or 10%, or 5%, or 1%) of the yield otherwise obtained without a particular substituent or substituent combination). Further, substituents are chosen so as to be chemically compatible with the other groups present and to avoid side reactions known to those skilled in the art. For example, an alcohol would not be substituted with a lithium group, as the hydroxide of the alcohol and the lithium group are incompatible and would react with each other. For any group in this disclosure, each substituent may include up to 40, 35, 30, 25, 20, 18, 16, 14, 12, 11, 10, 9, 8, 7, 6, 5, 4 or 3 carbon atoms. Overall, the total number of carbon atoms in all the substituents for any group is, in certain embodiments, 80, 75, 70, 65, 60, 55, 50, 45, 40, 35, 30, 25, 20, 18, 16, 14, 12, 11, 10, 9, 8, 7, 6, 5, 4 or 3 or less.

The term "heterocycle", "heterocyclic", "heterocyclic group" or "heterocyclo" refers to fully saturated or partially or completely unsaturated cyclic groups having at least one heteroatom in at least one carbon atom-containing ring, including aromatic ("heteroaryl") or nonaromatic (for example, 3 to 13 member monocyclic, 7 to 17 member bicyclic, or 10 to 20 member tricyclic ring systems). Each ring of the heterocyclic group containing a heteroatom may have 1, 2, 3, or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system. The rings of multi-ring heterocycles may be fused, bridged and/or joined through one or more spiro unions. Nitrogen-containing bases are examples of heterocycles. Other examples include piperidinyl, morpholinyl and pyrrolidinyl.

The terms "substituted heterocycle", "substituted heterocyclic", "substituted heterocyclic group" and "substituted heterocyclo" refer to heterocycle, heterocyclic, and heterocyclo groups substituted with one or more groups preferably selected from alkyl, substituted alkyl, alkenyl, oxo, aryl, substituted aryl, heterocyclo, substituted heterocyclo, carbocyclo (optionally substituted), halo, hydroxy, alkoxy (optionally substituted), aryloxy (optionally substituted), alkanoyl (optionally substituted), aroyl (optionally substituted), alkylester (optionally substituted), arylester (optionally substituted), cyano, nitro, amido, amino, substituted amino, lactam, urea, urethane, sulfonyl, and the like, where optionally one or more pair of substituents together with the atoms to which they are bonded form a 3 to 7 member ring.

The phrase "protecting group" as used herein refers to a species which prevents a portion of a molecule from undergoing a specific chemical reaction, but which is removable from the molecule following completion of that reaction. A "protecting group" is used in the conventional chemical sense as a group which reversibly renders unreactive a functional group under certain conditions of a desired reaction, as taught, for example, in Greene, et al., "Protective Groups in Organic Synthesis," John Wiley and Sons, Second Edition, 1991. After the desired reaction, protecting groups may be removed to deprotect the protected functional group. All protecting groups should be removable (and hence, labile) under conditions which do not degrade a substantial proportion of the molecules being synthesized. In contrast to a protecting group, a "capping group" permanently binds to a segment of a molecule to prevent any further chemical transformation of that segment. It should be noted that the functionality protected by the protecting group may or may not be a part of what is referred to as the protecting group.

A "hydroxyl protecting group" or "O-protecting group" refers to a protecting group where the protected group is a hydroxyl. A "reactive-site hydroxyl" is the terminal 5'-hydroxyl during 3'-5' polynucleotide synthesis, or the 3'-hydroxyl during 5'-3' polynucleotide synthesis. A "free reactive-site hydroxyl" is a reactive-site hydroxyl that is available to react to form an internucleotide bond (e.g. with a phosphoramidite functional group) during polynucleotide synthesis.

A "thiocarbon protecting group" refers to a protecting group linked through a carbonyl which additionally has a sulfur linked to a group independently selected from hydrogen, hydrocarbyls, and substituted hydrocarbyls; or a thionocarbonyl moiety which additionally has an oxygen, sulfur or nitrogen linked to one or more groups independently selected from hydrogen, a hydrocarbyl, a substituted hydrocarbyl, an aryl, a substituted aryl, a heterocycle and a substituted heterocycle. In certain embodiments, when oxygen or sulfur is the link, the group is not an aryl, substituted aryl, heterocycle or substituted heterocycle.

A "thionocarbonyl" refers to a sulfur atom double bonded to a carbon atom: >C=S

A "thionocarbamate protecting group" refers to a protecting group that includes a thionocarbonyl with a nitrogen and an oxygen bonded to the thionocarbonyl carbon atom: —O—C(S)N—

A "thiourea protecting group" or "thionourea protecting group" refers to a protecting group that includes a thionocarbonyl with two nitrogens bonded to the thionocarbonyl carbon atom, (—N—C(S)—N—). For example, a thiourea protecting group may be used to protect the exocyclic N of a nucleobase, or a heterocyclic base. In some cases described herein the group —C(S)—NR$^4$R$^5$ (where R$^4$ and R$^5$ are independently selected from hydrogen, a hydrocarbyl, a substituted hydrocarbyl, an aryl, a substituted aryl, a heterocycle and a substituted heterocycle) may be utilized as a thiourea protecting group, in which case it encompasses the exocyclic amine of the nucleobase in its structure.

The term "deprotect" or deprotection" refers to the removal of at least one protecting groups from the oligonucleotide of interest.

The term "base-labile protecting group" refers to a protecting group that can be removed by treatment with an aqueous or non-aqueous base. As used herein, the term is meant to include cases in which the protecting group removal involves the base acting as a nucleophile, for example, certain compositions comprising an amine base.

The term "deprotecting simultaneously" refers to a process which aims at removing different protecting groups in the same process and performed substantially concurrently or concurrently. However, as used herein, this term does not imply that the deprotection of the different protecting groups occur at exactly the same time or with the same rate or same kinetics, but that the deprotections occur during the single step of contacting with a deprotection composition. In some embodiments the term "simultaneously" or "simultaneous" also refers to removing different protecting groups in the same process as cleaving a polynucleotide from a solid support, and is performed substantially concurrently or concurrently.

The term "diamine" as used herein refers to a reagent comprising two amino groups independently selected from a primary and a secondary amino group. Examples of diamines include, 1,2-diaminoethane, 1,4-diaminobutane, N-ethyl-1,2-diaminoethane, 2,2'-diaminodiethylamine, and the like.

The term "phosphoramidite group" refers to a group comprising the structure —P(OR$^{13}$)(NR$^{14}$R$^{15}$), wherein each of R$^{13}$, R$^{14}$, and R$^{15}$ is independently a hydrocarbyl, substituted hydrocarbyl, heterocycle, substituted heterocycle, aryl or substituted aryl. In some embodiments, R$^{13}$, R$^{14}$, and R$^{15}$ may be selected from lower alkyls, lower aryls, and substituted lower alkyls and lower aryls (preferably substituted with structures containing up to 18, 16, 14, 12, 11, 10, 9, 8, 7, 6, 5, 4, 3 or 2 carbons). In some embodiments, R$^{13}$ is 2-cyanoethyl or methyl, and either or both of R$^{14}$ and R$^{15}$ is isopropyl. R$^{14}$ and R$^{15}$ can optionally be cyclically connected.

The term "H-phosphonate" refers to a group comprising the structure —P—(O)(H)(OR$^{16}$), wherein R$^{16}$ is H, acyl, substituted acyl, hydrocarbyl, substituted hydrocarbyl, heterocycle, substituted heterocycle, aryl or substituted aryl. In some embodiments, R$^{16}$ may be selected from lower alkyls, lower aryls, and substituted lower alkyls and lower aryls (preferably substituted with structures containing up to 18, 16, 14, 12, 11, 10, 9, 8, 7, 6, 5, 4, 3 or 2 carbons). In some embodiments, R$^{16}$ is pivaloyl or adamantoyl.

The term "alkyl" as used herein, unless otherwise specified, refers to a saturated straight chain, branched or cyclic hydrocarbon group of 1 to 24, typically 1-12, carbon atoms, such as methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The term "lower alkyl" intends an alkyl group of one to six carbon atoms, and includes, for example, methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The term "cycloalkyl" refers to cyclic alkyl groups such as cyclopropyl, cyclobutyl, cyclopentyl, cyclohexyl, cycloheptyl and cyclooctyl.

Moreover, the term "alkyl" includes "modified alkyl", which references an alkyl group having from one to twenty-four carbon atoms, and further having additional groups, such as one or more linkages selected from ether-, thio-, amino-, phospho-, oxo-, ester-, and amido-, and/or being substituted with one or more additional groups including lower alkyl, aryl, alkoxy, thioalkyl, hydroxyl, amino, sulfonyl, thio, mercapto, imino, halo, cyano, nitro, nitroso, azide, carboxy, sulfide, sulfone, sulfoxy, phosphoryl, silyl, silyloxy, and boronyl. Similarly, the term "lower alkyl" includes "modified lower alkyl", which references a group having from one to eight carbon atoms and further having additional groups, such as one or more linkages selected from ether-, thio-, amino-, phospho-, keto-, ester-, and amido-, and/or being substituted with one or more groups including lower alkyl; aryl, alkoxy, thioalkyl, hydroxyl, amino, sulfonyl, thio, mercapto, imino, halo, cyano, nitro, nitroso, azide, carboxy, sulfide, sulfone, sulfoxy, phosphoryl, silyl, silyloxy, and boronyl. The term "alkoxy" as used herein refers to a substituent —O—R wherein R is alkyl as defined above. The term "lower alkoxy" refers to such a group wherein R is lower alkyl. The term "thioalkyl" as used herein refers to a substituent —S—R wherein R is alkyl as defined above.

The term "alkenyl" as used herein, unless otherwise specified, refers to a branched, unbranched or cyclic (e.g. in the case of C5 and C6) hydrocarbon group of 2 to 24, typically 2 to 12, carbon atoms containing at least one double bond, such as ethenyl, vinyl, allyl, octenyl, decenyl, and the like. The term "lower alkenyl" intends an alkenyl group of two to eight carbon atoms, and specifically includes vinyl and allyl. The term "cycloalkenyl" refers to cyclic alkenyl groups.

The term "alkynyl" as used herein, unless otherwise specified, refers to a branched or unbranched hydrocarbon group of 2 to 24, typically 2 to 12, carbon atoms containing at least one triple bond, such as acetylenyl, ethynyl, n-propynyl, isopropynyl, n-butynyl, isobutynyl, t-butynyl, octynyl, decynyl and the like. The term "lower alkynyl" intends an alkynyl group of two to eight carbon atoms, and includes, for example, acetylenyl and propynyl, and the term "cycloalkynyl" refers to cyclic alkynyl groups.

The term "hydrocarbyl" refers to alkyl, alkenyl or alkynyl. The term "substituted hydrocarbyl" refers to hydrocarbyl moieties having substituents replacing a hydrogen on one or more carbons of the hydrocarbon backbone. Such substituents may include, for example, a hydroxyl, a halogen, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclic, an aralkyl, or an aromatic or heteroaromatic moiety. It will be understood by those skilled in the art that the moieties substituted on the hydrocarbon chain may themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CN, and the like. Cycloalkyls may be further substituted with alkyls, alkenyls, alkoxys, alkylthios, aminoalkyls, carbonyl-substituted alkyls, —CN, and the like.

The term "alkoxy" means an alkyl group linked to oxygen and may be represented by the formula: R—O—, wherein R represents the alkyl group. An example is the methoxy group $CH_3O$—.

The term "aryl" refers to 5-, 6-, and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The term "aryl" also includes polycyclic ring systems having two or more cyclic rings in which two or more carbons are common to two adjoining rings (the rings are "fused rings") wherein at least one of the rings is aromatic (e.g., the other cyclic rings may be cycloalkyls, cycloalkenyls, cycloalkynyls, aryls, and/or heterocycles). A "lower aryl" contains up to 18 carbons, such as up to 14, 12, 10, 8 or 6 carbons.

The aromatic rings may be substituted at one or more ring positions with such substituents as described above for substituted hydrocarbyls, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclic, aromatic or heteroaromatic moieties, —$CF_3$, —CN, or the like.

The terms "halogen" and "halo" refer to a fluoro, chloro, bromo, or iodo moiety.

The terms "linkage" or "linker" as used herein refers to a first moiety bonded to two other moieties, wherein the two other moieties are linked via the first moiety. In some embodiments a "linkage" or "linker" may include an ether (—O—), a carbonyl (—C(O)—), an amino (—NH—), an amido (—N—C(O)—), a thio (—S—), a phospho (—O—P(X)(OR)—O— wherein X is O or S; and R is hydrogen, a hydrocarbyl, a substituted hydrocarbyl, an aryl, or a substituted aryl), an ester (—C(O)O—), a carbonate (—OC(O)O—), a carbamate (—OC(O)NH—), a thiono (—C(S)—). In some embodiments, the "linker" refers to a moiety that links two amino groups. In some embodiments, the "linkage" or "linker" refers to a moiety that links two nucleoside residues of a polynucleotide. In some embodiments, the "linker" refers to a moiety that links a moiety to a solid support, for example, a base-labile, fluoride-labile, peroxy-labile, acid-labile or photocleavable linker that connects a covalently bound nucleoside to a solid support.

"Functionalized" references a process whereby a material is modified to have a specific moiety bound to the material, e.g. a molecule or substrate is modified to have the specific moiety; the material (e.g. molecule or support) that has been so modified is referred to as a functionalized material (e.g. functionalized molecule or functionalized support).

The term "substituted" as used to describe chemical structures, groups, or moieties, refers to the structure, group, or moiety comprising one or more substituents. As used herein, in cases in which a first group is "substituted with" a second group, the second group is attached to the first group whereby a moiety of the first group (in some cases a hydrogen) is replaced by the second group.

"Substituent" references a group that replaces another group in a chemical structure. In some cases substituents include nonhydrogen atoms (e.g. halogens), functional groups (such as, but not limited to amino, amido, sulfhydryl, carbonyl, hydroxyl, alkoxy, carboxyl, silyl, silyloxy, phosphate and the like), hydrocarbyl groups, and hydrocarbyl groups substituted with one or more heteroatoms. Exemplary substituents include alkyl, lower alkyl, aryl, aralkyl, lower alkoxy, thioalkyl, hydroxyl, thio, mercapto, amino, imino, halo, cyano, nitro, nitroso, azide, carboxy, sulfide, sulfone, sulfoxy, phosphoryl, silyl, silyloxy, boronyl, and modified lower alkyl.

The term "hydrogen substituent", "hydrogen", "H" or "hydrogen group" as used in some embodiments described herein refers to a hydrogen moiety bound to another moiety or group of a chemical structure. It will be understood that in certain embodiments, a compound comprising a hydrogen substituent bound to any suitable group (for example a phosphate group or a carboxylate group) may, under suitable conditions, form a salt. As such, these salts may readily exchange with other ions, so that, for example, a compound comprising a phosphate group and a hydrogen substituent, such as a nucleotide or nucleic acid, may be present as a sodium, potassium or ammonium salt, especially in an aqueous buffer. As such, the term "hydrogen substituent", "hydrogen", or "hydrogen group" also refers to ionic species and various salt species.

Hyphens, or dashes are used at various points throughout this specification to indicate attachment, e.g. where two named groups are immediately adjacent to a dash in the text. This indicates that the two named groups are attached to each other. Similarly, a series of named groups with dashes between each of the named groups in the text indicate the named groups are attached to each other in the order shown. Also, a single named group adjacent a dash in the text indicates that the named group is typically attached to some other, unnamed group. In some embodiments, the attachment indicated by a dash may be, e.g., a covalent bond between the adjacent named groups. At various points throughout the specification, a group may be set forth in the text with or without an adjacent dash, (e.g. amido or amido-, further e.g. alkyl or alkyl-, yet further Lnk, Lnk- or -Lnk-) where the context indicates the group is intended to be (or has the potential to be) bound to another group; in such cases, the identity of the group is denoted by the group name (whether or not there is an adjacent dash in the text). Note that where context indicates, a single group may be attached to more than one other group (e.g., where a linkage is intended, such as linking groups).

Dashed lines (e.g., ------) are used throughout the specification adjacent to named groups to indicate attachment to some other, unnamed group.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present, and, thus, the description includes structures wherein a non-hydrogen substituent is present and structures wherein a non-hydrogen substituent is not present. At various points herein, a moiety may be described as being present zero or more times: this is equivalent to the moiety being optional and includes embodiments in which the moiety is present and embodiments in which the moiety is not present. If the optional moiety is not present (is present in the structure zero times), adjacent groups described as linked by the optional moiety are linked to each other directly. Similarly, a moiety may be described as being either (1) a group linking two adjacent groups, or (2) a bond linking the two adjacent groups: this is equivalent to the moiety being optional and includes embodiments in which the moiety is present and embodiments in which the moiety is not present. If the optional moiety is not present (is present in the structure zero times), adjacent groups described as linked by the optional moiety are linked to each other directly.

"Bound" may be used herein to indicate direct or indirect attachment. In the context of chemical structures, "bound" (or "bonded") may refer to the existence of a chemical bond directly joining two moieties or indirectly joining two moieties (e.g. via a linking group or any other intervening portion of the molecule). The chemical bond may be a covalent bond, an ionic bond, a coordination complex, hydrogen bonding, van der Waals interactions, or hydrophobic stacking, or may exhibit characteristics of multiple types of chemical bonds. In certain instances, "bound" includes embodiments where the attachment is direct and also embodiments where the attachment is indirect. In certain instances, "free," as used in the context of a moiety that is free, indicates that the moiety is available to react with or be contacted by other components of the solution in which the moiety is a part. In certain instances, "free," as used in the context of a moiety that is free, indicates that the moiety is no longer covalently bound to a solid support.

The term "assessing" includes any form of measurement, and includes determining if an element is present or not. The terms "determining", "measuring", "evaluating", "assessing" and "assaying" are used interchangeably and may include quantitative and/or qualitative determinations. Assessing may be relative or absolute. "Assessing the presence of" includes determining the amount of something present and/or determining whether it is present or absent.

"Isolated" or "purified" generally refers to isolation of a substance (compound, polynucleotide, protein, polypeptide, polypeptide, chromosome, etc.) such that the substance comprises a substantial portion of the sample in which it resides (excluding solvents), i.e. greater than the substance is typically found in its natural or un-isolated state. Typically, a substantial portion of the sample comprises at least about 1%, at least about 5%, at least about 10%, at least about 20%, at least about 30%, at least about 50%, preferably at least about 80%, or more preferably at least about 90% of the sample (excluding solvents). For example, a sample of isolated RNA will typically comprise at least about 5% total RNA, where percent is calculated in this context as mass (e.g. in micrograms) of total RNA in the sample divided by mass (e.g. in micrograms) of the sum of (total RNA+other constituents in the sample (excluding solvent)). Techniques for purifying polynucleotides and polypeptides of interest are well known in the art and include, for example, gel electrophoresis, ion-exchange chromatography, reverse-phase chromatography, reverse phase-ion pairing chromatography, affinity chromatography, flow sorting, and sedimentation according to density. In typical embodiments, one or more of the nucleotide composition(s) is in isolated form; more typically, all three are obtained in isolated form prior to use in the present methods.

The term "pre-determined" refers to an element whose identity is known prior to its use. For example, a "pre-determined sequence" is a sequence whose identity is known prior to the use or synthesis of the polynucleotide having the sequence. An element may be known by name, sequence, molecular weight, its function, or any other attribute or identifier.

"Upstream" as used herein refers to the 5' direction along a polynucleotide, e.g. an RNA molecule. "Downstream" refers to the 3' direction along the polynucleotide.

The term "RNA", or "ribonucleic acid" refers to a polynucleotide or oligonucleotide which comprises at least one ribonucleotide residue.

DETAILED DESCRIPTION

The disclosures of prior U.S. application Ser. No. 12/118,655 filed May 9, 2008, which in turns claims the benefit under 35 U.S.C. § 119(e) of prior U.S. provisional application Ser. No. 60/928,722 filed May 10, 2007, are both incorporated herein by reference.

Aspects of this disclosure relate to the use of compositions comprising diamines, e.g., 1,2-diaminoethane, substituted versions of 1,2-diaminoethane, and solvent solutions comprising 1,2-diaminoethane or substituted versions of 1,2-diaminoethane for the deprotection of synthetic RNA molecules and polynucleotides comprising a ribonucleotide residue under conditions that do not lead to significant cleavage or isomerization of the internucleotide bond. Also described are methods for on-column deprotection of RNA molecules and polynucleotides that comprise a ribonucleotide residue and the automated deprotection of RNA molecules. One aspect of this disclosure is a method for deprotecting a polynucleotide comprised of one or more ribonucleotide moieties, synthesized on solid support, the method comprising the steps of; (1) providing a solid support having said synthesized polynucleotide attached thereto, and (2) simultaneously or after having removed the 2'-protecting groups of said polynucleotide, incubating the solid support with a composition comprising a diamine; for example 1,2-diaminoethane or a substituted 1,2-diaminoethane; and optionally comprising another amine or mixtures thereof, and optionally comprising an organic solvent or mixtures thereof; and optionally comprising up to 20% by volume of an aqueous solution; under conditions suitable to deprotect and cleave the polynucleotide from the solid support; and (3) removing the composition in a manner such that the polynucleotides are retained on the support, and (4) optionally washing the support with an organic solvent, and (5) optionally washing the solid support and recovering the polynucleotides by elution with water, an aqueous buffer, or a chromatographic mobile phase. In some cases, the removing and washing steps described herein, that involve a solid support bound or cleaved polynucleotide, may be performed through the use of an inert gas, or a vacuum, or the like, and may also include steps of drying or evaporation. In some cases, the removing and wash steps may be repeated one or more times. In some cases a wash step may include contacting a solid support or cleaved polynucleotide with a wash solution for a period of time before removing the wash solution from the solid support or cleaved polynucleotide.

In particular embodiments described herein, a diamine composition used in the instant deprotection method may be made up of at least 10% (e.g., at least 20%, at least 30%, at least 40%, at least 50%, at least 60%, at least 70%, at least 80%, at least 90%, at least 95%, at least 98%, at least 99%, up to 100% (i.e., neat diamine)) diamine by volume of the composition, where a diamine can be a single diamine or a mixture thereof. If a diamine composition contains less than 100% diamine, then the non-diamine portion of the composition may be a solvent, for example, toluene, 2-methyl-THF (Me-THF), THF, acetonitrile (MeCN), dichloromethane (DCM), 1,4-dioxane, morpholine or an mixture thereof; where such a composition contains at least 90%, at least 80%, at least 70%, at least 60%, at least 50%, at least 40%, at least 30%, at least 20%, at least 10%, at least 5%, at least 2%, at least 1%, or <1% solvent, by volume. The composition may optionally comprise an additional amine, deprotection or scavenger reagent, or mixtures thereof (for example diethylamine or triethylamine); optional components may be present at an amount not exceeding 90%, e.g., less than about 90%, less than about 80%, less than about 70%, less than about 60%, less than about 50%, less than about 40%, less than about 30%, less than about 20%, less than about 10%, less than about 5%, less than about 2%, less than about 1%, or <1% by volume. In particular embodiments, the composition may also optionally comprise up to 20% (e.g., up to 10%, up to 5%, up to 2%, up to 1%, or <1%) water, by volume.

In certain embodiments the diamine composition disclosed herein may comprise two or more diamines, for example, 1,2-diaminoethane and 1,3-diaminopropane.

In some embodiments a deprotection composition described herein includes a diamine comprising two amino groups independently selected from a primary amino and a secondary amino group, and separated by a linker; wherein the linker is a chain of about 2 to 12 atoms in length, for example 2 to 6 atoms, or 2 atoms in length; and wherein the linker may optionally comprise a heteroatom, for example, from about 1 to 4 heteroatoms selected from O, N and S. In certain embodiments the linker may optionally be substituted or branched at one or more atoms, for example with a hydrocarbyl, substituted hydrocarbyl, aryl, or substituted aryl group. In particular embodiments the diamine linker may optionally be substituted or branched at one or more atoms, for example with an alkyl or substituted alkyl group. In particular embodiments the diamine comprises two primary amino groups. In particular embodiments the diamine comprises a primary amino group and a secondary amino group. In particular embodiments the diamine comprises two secondary amino groups.

In particular embodiments, a diamine reagent is selected from 1,2-diaminoethane, 1,2-diaminopropane, 1,3-diaminopropane, 1,4-diaminobutane, 2,2'-diaminodiethylamine.

In certain embodiments a diamine reagent described herein may be a polymer of a diamine wherein the linker comprises about 2 to 6, or 2 to 3 atoms, for example a polymer of 1,2-diaminoethane having the structure:

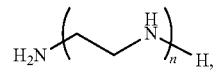

wherein n is an integer equal to 2 or greater, for example n is between about 2 and 10.

In certain embodiments a substituted derivative of 1,2-diaminoethane may have the structure of Formula (VII), wherein $R^2$, $R^3$, $R^4$ are independently selected from: H, a hydrocarbyl, a substituted hydrocarbyl, an aryl, and a substituted aryl; and wherein $Z^1$ and $Z^2$ are each independently selected from H, hydrocarbyl, substituted hydrocarbyl, aryl, substituted aryls, alkyl-substituted amine, and aminoalkyl-substituted amine. In particular embodiments a substituted derivative of 1,2-diaminoethane may have the structure of Formula (VII), wherein $R^2$, $R^3$, $R^4$ are independently selected from H, an lower alkyl, a branched lower alkyl, or substituted versions thereof; and wherein $Z^1$ and $Z^2$ are each H.

$$Z^1-NH-CR^3R^4-CR^1R^2-NH-Z^2 \qquad \text{VII}$$

In certain embodiments a substituted derivative of 1,2-diaminoethane may have a structure of Formula (VIII), wherein $R^1$ and $R^2$, are independently selected from H, a hydrocarbyl, a substituted hydrocarbyl, an aryl, and a substituted aryl; and wherein Z is selected from H, a hydrocarbyl, a substituted hydrocarbyl, an aryl, a substituted aryl, an alkyl-substituted amine, and an aminoalkyl-substituted amine. In particular embodiments a substituted derivative of 1,2-diaminoethane may have the structure of Formula (VIII), wherein and $R^2$ are independently selected from H, an lower alkyl, a branched lower alkyl, or substituted versions thereof; and wherein Z is H.

In some embodiments, 1,2-diaminoethane derivatives are selected from the group consisting of 1,2-Propanediamine, 1,2-Ethanediamine, N1-methyl-1,2-Ethanediamine, N1-ethyl-1,2-Ethanediamine, N1-propyl-1,2-Ethanediamine, N1-(2-amino ethyl)-1,2-Ethanediamine, Ethanol, 2-[(2-aminoethyl)amino]-, 1,2-Ethanediamine, N1,N2-bis (2-aminoethyl)-, 1,2-Ethanediamine, N1-(2-aminoethyl)-N2-[2-[(2-aminoethyl)amino]ethyl]-, 2-Propanol, 1-[(2-aminoethyl)amino]-, 1,2-Ethanediamine, N1-1-naphthalenyl-, 1,2-Propanediamine, 2-methyl-, Ethanol, 2-[[2-[(2-aminoethyl)amino]ethyl]amino]-, 1,2-Ethanediamine, N1-[3-(dimethoxymethylsilyl)propyl]-, 1,2-Ethanediamine, N1-[3-(methoxydimethylsilyl)propyl]-, 1,2-Ethanediamine, N1-(2-phenylethyl)-, 1,2-Ethanediamine, N1-(phenylmethyl)-, 1,2-Butylenediamine; 1,2-Diaminobutane; 1,2-Ethanediamine, 1-ethyl-, 1,2-Ethanediamine, N1-[3-(triethoxysilyl)propyl]-, 1,2-Ethanediamine, N1-[2-(1-piperidinyl)ethyl]-, 1,2-Ethanediamine, N1-[2-(4-morpholinyl) ethyl]-, 1,2-Ethanediamine, N-2-thiazolyl-), 1,2-Ethanediamine, 1-phenyl-, Propanenitrile, 3-[[2-[(2-aminoethyl)amino]ethyl]amino]-, 1,2-Ethanediamine, N-(2-furanylmethyl)-1,2-Ethanediamine, N1-(4-pyridinylmethyl)-, 1,2-Ethanediamine, N-[(tetrahydro-2-furanyl)methyl]-, 1,2-Ethanediamine, N1-(1-methylethyl)-, 1,2-Ethanediamine, N-[(trimethylsilyl)methyl]-, 1,2-Ethanediamine, N-(2-aminoethyl)-N'-phenyl-1,2-Ethanediamine, N1-(2-aminoethyl)-N2-[2-[(phenylmethyl)amino] ethyl]-, Propanenitrile, 3-[(2-aminoethyl)amino]-, 1,2-Ethanediamine, N1-[3-(dimethoxymethylsilyl)-2-methylpropyl]-, 1,2-Ethanediamine, N1-[2-(1-piperazinyl) ethyl]-, 1,3-Propanediamine, N3-(2-aminoethyl)-N1,N1-dimethyl-, 1,2-Ethanediamine, N2-(2-aminoethyl)-N1,N1-dimethyl-, 1,2-Ethanediamine, N2-(2-aminoethyl)-N1,N1-diethyl-, Ethylenediamine, N-[2-methyl-3-(trimethylsilyl) propyl]-, 1,2-Ethanediamine, N1-[3-(methoxydimethylsilyl)-2-methylpropyl]-, 1,2-Ethanediamine, N1-(2-aminoethyl)-N2-[2-(1-piperazinyl) ethyl]-, 1,2-Ethanediamine, N-1H-benzimidazol-2-yl-, 1,2-Ethanediamine, N1-(2-aminoethyl)-N2-[3-(trimethoxysilyl) propyl]-, Carbamic acid, N-[2-[(2-aminoethyl)amino] ethyl]-, 2-Propanol, 1-[[2-[(2-aminoethyl)amino]ethyl] amino]-, Propanenitrile, 2-[[2-[(2-aminoethyl)amino]ethyl] amino]-, 1,2-Propanediamine, N1-(2-amino-1-methylethyl)-, 1-Propanol, 3-[(2-aminoethyl)amino]-, 1,2-Ethanediamine, N1-methyl-1-phenyl-, Propanenitrile, 3-[[2-[[2-[(2-aminoethyl)amino]ethyl]amino]ethyl]amino]-, Tetradecanamide, N-[2-[(2-aminoethyl)amino]ethyl]-, 1,2-Ethanediamine, N-(4,5-dihydro-1H-imidazol-2-yl)-2-Propanol, 1-[[2-[(2-aminoethyl)amino]ethyl]amino]-3-phenoxy-, 1,2-Ethanediamine, N-[2-(4-pyridinyl)ethyl]-, Glycine, N-[2-[(2-aminoethyl)amino]ethyl-N-dodecyl-, 1,2-Ethanediamine, N1-(2-aminoethyl)-N2-(2-ethylhexyl)-, 1,2-Ethanediamine, N1-[1-(1-piperazinyl)ethyl]-, 1,2-Propanediamine, N2-(2-aminoethyl)-, Benzenamine, N-[1-(aminomethyl)cyclohexyl]-, 4-Piperidinemethanamine, 4-amino-1-(phenylmethyl)-, 1,2-Butanediamine, 2,3-dimethyl-, 1,2-Butanediamine, 3,3-dimethyl-, 1,2-Ethanediamine, N1-(2-aminoethyl)-N2-(1-methylethyl)-, Valine, N-(2-aminoethyl)-, Ethanone, 1-[2-[(2-aminoethyl)amino]-1-cyclopenten-1-yl]-, 1,2-Ethanediamine, N1-(1,4-dioxaspiro[4.4]non-2-ylmethyl)-, 1,2-Ethanediamine, N1-(2-piperazinylmethyl)-, 1,2-Ethanediamine, N1-[3-(1-piperazinyl) propyl]-, 1,2-Ethanediamine, N1-(1-methyl-4-piperidinyl)-, 1,2-Ethanediamine, N1-[2-(1H-pyrazol-1-yl)ethyl]-, 1-Piperidinecarboxylic acid, 4-amino-4-(aminomethyl)-, 1,1-dimethylethyl ester.

In particular embodiments, 1,2-diaminoethane derivatives described herein are selected from the group consisting of 1,2-diaminoethane, 1,2-diaminopropane, N-(2-aminoethyl)-1,2-ethanediamine and N-ethyl-1,2-ethanediamine.

In certain embodiments, a polynucleotide is bound on a solid support via a linker that is stable (i.e., orthogonal) to treatment with a diamine reagent composition disclosed herein, for example, a photocleavable, a peroxyanion-sensitive or a fluoride-labile linker, such that the polynucleotide may be deprotected but remains uncleaved.

Some aspects of this disclosure include deprotection of base-labile 2'-hydroxyl protecting group moieties and the nucleobase exocyclic amine protecting group moieties in a single step. Other aspects include the simultaneous deprotection of base-labile 2'-hydroxyl protecting group moieties, the nucleobase exocyclic amine protecting group moieties, and the phosphorus protecting group moiety. Additional aspects are simultaneous deprotection of base-labile 2'-hydroxyl protecting group moieties, the nucleobase exocyclic amine protecting group moieties, the phosphorus protecting group moiety, and cleavage of a solid support linker. Another aspect is cleavage of a solid support linker simultaneously with cleavage of the 2'-hydroxyl protecting group under conditions that retain a polynucleotide (for example, a RNA) product on the column. In certain embodiments, the 2'-hydroxyl protecting group is not an ester protecting group, e.g., where a ribonucleotide residue is protected at the 2' hydroxyl position by an ester (i.e., the 2'-hydroxyl is acylated). Also described are polynucleotides comprising a 2'-protected nucleotide residue that are protected at the 2' site with thionocarbamate protecting groups that can be removed simultaneously with the nucleobase exocyclic amine moieties. In certain embodiments a 2'-thionocarbamate protecting group can be removed simultaneously with cleavage of the solid support linking group or simultaneously with cleavage of the solid support linking group and cleavage of a protecting group on a nucleobase exocyclic amine moiety. In particular embodiments, a 2'-thionocarbamate protected nucleotide residue can be deprotected and cleaved as described above, such that the cleaved polynucleotide is retained on the solid support; and wherein the cleaved polynucleotide may be optionally washed to separate reagents and cleaved protecting groups from the cleaved polynucleotide product; and wherein the cleaved polynucleotide may be eluted from the solid support.

Particular embodiments include nucleic acids comprising a 2'-thionocarbamate protecting group as well as methods of synthesizing nucleic acids comprising a thionocarbamate protecting group, and the deprotecting of synthetic polynucleotides, for example RNA.

Before describing some embodiments in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed herein. The upper and lower limits of these smaller ranges may independently be included in the smaller ranges and are also encompassed within certain embodiments, subject to any specifically excluded limit in the stated range. Where the stated range includes one or both of the limits, ranges excluding either or both of those included limits are also included in certain embodiments.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art. Although any methods and materials similar or equivalent to those described herein can also be used in the practice or testing of the particular embodiments, some illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It should be noted that, as is conventional in drawing some chemical structures, some of the hydrogens are omitted from the drawn structures for clarity purposes, but should be understood to be present, e.g. where necessary to completely fill out the valence bonding of a carbon in a drawn structure.

As will be apparent to those of skill in the art upon reading this disclosure, particular embodiments described and illustrated herein have discrete components and features which may be readily separated from or combined with the features of any other particular embodiments without departing from the scope or spirit of the present disclosure. Any recited method can be carried out in the order of events recited or in any other order which is logically possible.

Monomers Protected with 2'-Thionocarbamate Protecting Groups

As disclosed above, certain embodiments include 2'-thionocarbamate protecting groups and monomers comprising a thionocarbamate protecting group protecting a 2'-hydroxyl of the monomer. By thionocarbamate protecting group is meant a hydroxyl protecting group which includes a sulfur atom double bonded to a carbon atom, and a nitrogen atom bonded to the same carbon atom, such as is present in the thionocarbamate protecting groups of particular embodiments, discussed in greater detail below.

In certain embodiments, a monomer described herein comprises a 2'-thionocarbamate protecting group, e.g., as found in compounds by the structure shown in Formula Ia, where $B^P$ is a protected or unprotected heterocycle, and each of $R^1$ or $R^2$ is independently selected from hydrogen, a protecting group, and a phosphoramidite group or H-phosphonate group; and wherein Y is $NH_2$, a secondary amine (—NH—Z), a tertiary amine (—NZ—Z"), a secondary hydroxyl amine (—NH—O—Z), or a tertiary hydroxyl amine (—NZ—O—Z"), and wherein Z and Z" are independently selected from hydrocarbyls, substituted hydrocarbyls, aryls, substituted aryls, and wherein Z or Z" can be cyclically linked.

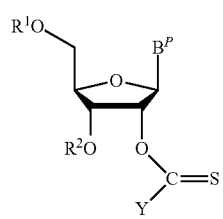

Ia

In some cases, thionocarbamate protecting groups described herein include primary, secondary, and tertiary thionocarbamates. Some embodiments of these compounds include those represented by the following formulas Ic and Id and Ie and If and Ig below; wherein $R^1$, $R^2$ and $B^P$ are selected as described above; and wherein $R_3$ is selected from hydrocarbyls, substituted hydrocarbyls, aryls, substituted aryls and $R_4$ and $R_5$ are independently selected from hydrocarbyls, substituted hydrocarbyls, aryls, substituted aryls, and wherein optionally $R_4$ and $R_5$ can be cyclically linked.

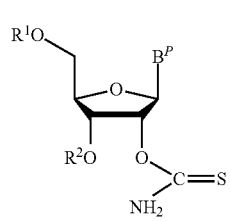

Ic

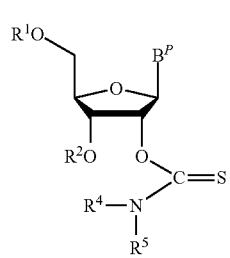

Id

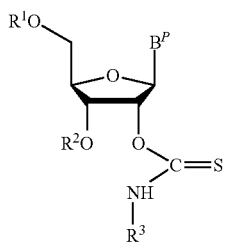
Ie
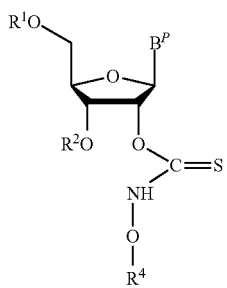
If
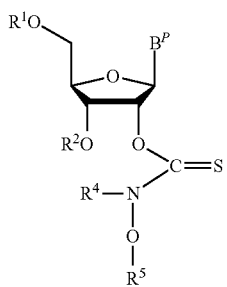
Ig
Some compounds described herein include those described by the following structures:
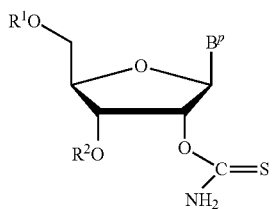
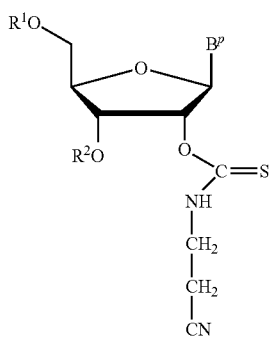
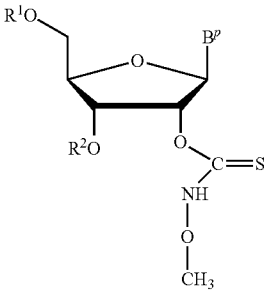
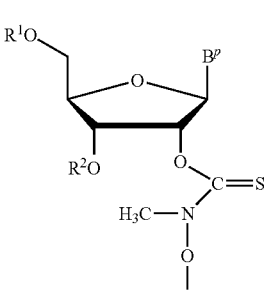
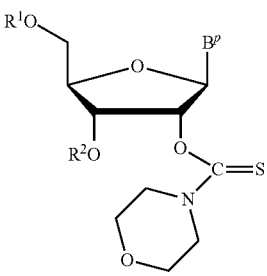
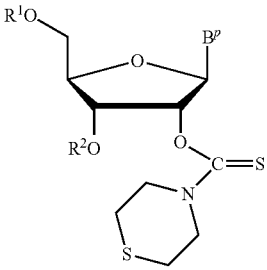
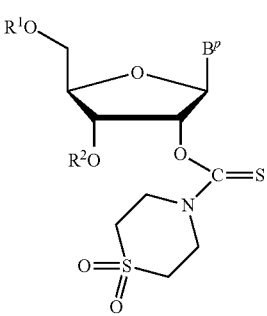

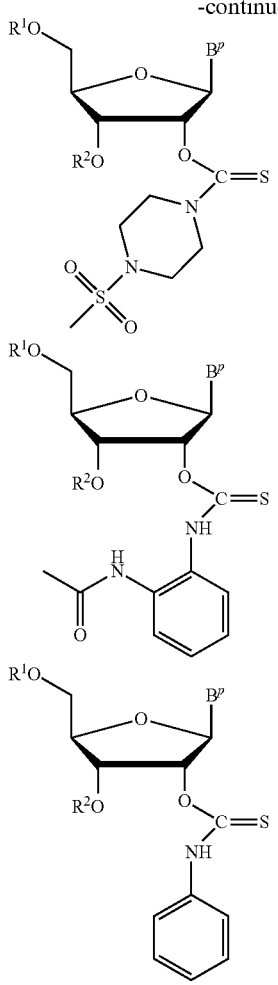

With respect to the above structures and formulas, the $B^P$ group is a protected or non-protected heterocycle. The heterocycle may be selected from the naturally occurring purine and pyrimidine bases, e.g., adenine (A), thymine (T), cytosine (C), guanine (G), or uracil (U), or modified purine and pyrimidine bases, and analogs thereof, e.g., such as are recited herein. Some embodiments of purine or pyrimidine analogs include those described in U.S. patent application Ser. No. 10/324,409 entitled "Method of Producing Nucleic Acid Molecules with Reduced Secondary Structure", filed on Dec. 18, 2002; and also those described in U.S. patent application Ser. No. 09/358,141, now abandoned, entitled "Method of Producing Nucleic Acid Molecules with Reduced Secondary Structure", filed on Jul. 20, 1999.

In some embodiments, the heterocycle is selected from 1-methyladenine, 2-methyladenine, $N^6$-methyladenine, $N^6$-isopentyladenine, 2-methylthio-$N^6$-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine and 2,6-diaminopurine.

In some embodiments, the heterocycle may have a protecting group, for example, a protecting group for use in polynucleotide synthesis. In certain embodiments, a heterocycle protecting group is selected from acetyl, difluoroacetyl, trifluoroacetyl, isobutyryl, benzoyl, 9-fluorenylmethoxycarbonyl, phenoxyacetyl, 4-tert-butylphenoxyacetyl, N,N-dimethylformamidine, N,N-dibutylforamidine, N,N-dimethylacetamidine, substituted thiourea and N,N-diphenyl carbamate is attached to the heterocycle through the exocyclic amine of the heterocycle, for example, $N^4C$, $N^6A$, $N^2G$.

In some embodiments, the heterocycle may have a thiourea-type protecting group, linked through the exocyclic amine $N^2$ (G), $N^4$(C) and $N^6$ (A) of the heterocycle such as —NC(S)—NHR$^a$ or —NC(S)NR$^a$R$^b$ wherein R$^a$ and R$^b$ are independently selected from a hydrocarbyl, a substituted hydrocarbyl, an aryl and a substituted aryl; as for example, a N,N-diphenyl thiourea or phenyl thiourea protecting group.

Synthesis of 2'-Thionocarbamate Protected Monomers

In some embodiments a nucleoside monomer comprising a thionocarbamate protecting group may be produced using any convenient protocol. In certain embodiments, a protected nucleoside monomer is produced using a protocol in which a nucleoside monomer having the structure shown in Formula (IIIa) is contacted with a compound having the structure: Q-LG, where Q is a thionocarbamate protecting group, e.g., as described above; and wherein LG may be any suitable leaving group, for example, an imidazole group; under conditions sufficient to produce a 2'-protected nucleoside monomer of the structure of Formula (IIIb). Leaving or activating groups include, but are not limited to: imidazole, chloro, p-nitrophenoxy, pentafluorophenoxy, O-succinimidyl, trichloromethyl, bromo, and iodo.

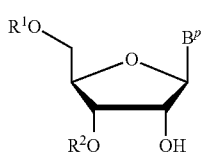

IIIa

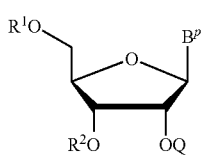

IIIb

With respect to structures of formulas IIIa and IIIb above, $B^P$ is a protected or unprotected heterocycle; and $R^1$ and $R^2$ are each a hydroxyl protecting group, wherein optionally $R^1$ and $R^2$ may be cyclically linked to form a bidentate protecting group, such as for example but not limited to a 1,3-tetraisopropyldisiloxane (TIPS) group.

In certain embodiments, as illustrated below, synthesis of monomers may employ a reagent, such as a Markiewicz TIPS reagent, to localize protecting groups to the 2'-OH site of the composition under synthesis, i.e., to provide regioselectivity. A regiospecific introduction on the 2'-hydroxyl protecting group is performed through the protection of the 5' and 3'-hydroxyl groups, e.g., through the use of a Markiewicz disilyloxane protecting group (Markiewicz W. T., *J. Chem. Research (S)*, 1979, 24-25) as shown in the structure of formula (IV) below.

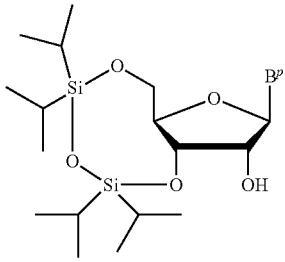

IV

In some embodiments, as shown in the following scheme; wherein $R^i$ is a thionocarbamate protecting group, and wherein $R^{iii}$ is an exocyclic amino heterocycle protecting group; a 1,3-tetraisopropyl disiloxane (TIPS) may be used as a bidentate protecting group to block the 5' and 3'-hydroxyls simultaneously, allowing the 2'-hydroxyl to be regioselectively protected, for example. Other bidentate protecting groups may also be employed. The 1,3-tetraisopropyl disiloxane group may be subsequently removed using a solution of fluoride ions.

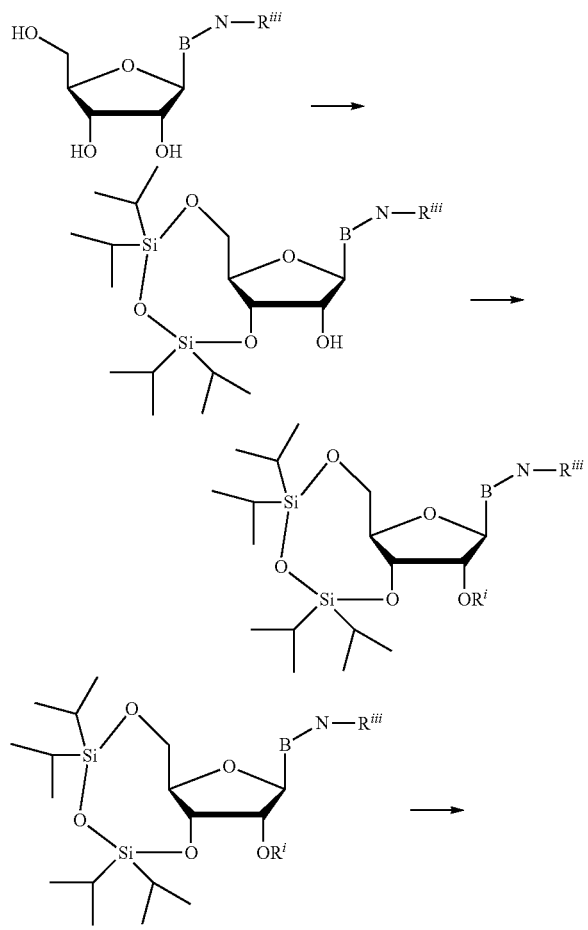

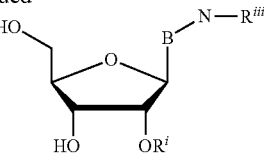

In certain embodiments, a nucleobase for nucleoside monomers described herein, may be protected using any suitable approach, for example by the Jones Procedure (originally described by Ti et al. *J. Am. Chem. Soc.*: 104, 1316-1319 (1982)). The Jones Procedure uses the transient silylation of unprotected nucleosides by trimethylsilyl chloride to allow carbonyl halides, activated carbonyl groups or carbonyl anhydrides to react regiospecifically with the exocyclic amine of the nucleobase by adding a large excess of trimethylsilyl chloride to a solution of the nucleoside in pyridine and dichloromethane. This results in trimethylsilylation of all of the hydroxyl groups of the sugar residue along with the exocyclic amine groups and potentially of the imino on the hetero bases. When silylated, the exocyclic amine groups retain their reactivity toward carbonyl halides, activated carbonyl groups or carbonyl anhydrides, while the hydroxyl groups of the sugar residue are protected from reaction with the same reagents. This results in regiospecific protection of the exocyclic amines. In certain procedures, trimethylsilyl groups are removed from the hydroxyl moieties by an aqueous workup in the presence of sodium bicarbonate. In particular embodiments, this procedure may be modified to support a non-aqueous workup by the addition of toluene sulfonic acid in a polar solvent. In certain embodiments for nucleoside monomers synthesized using the Markiewicz protecting group TIPS, it is possible to react the unprotected nucleoside with the TIPS group prior to performing the Jones reaction. Under these conditions the TIPS protected nucleoside is more soluble in organic solvents and as a result of the 5' and 3' hydroxyls being pre-protected, it is possible to use a smaller excess of trimethylsilyl chloride. After workup, the product from these reactions can be an N-protected-3', 5'-tetraisopropyldisiloxane nucleoside. This compound may then be connected to the 2'-protecting group.

Monomers may be synthesized from a nucleoside in which the nucleobase is already protected, for example by an acetyl (Ac), difluoroacetyl, trifluoroacetyl, isobutyryl (iBu), benzoyl (Bz), 9-fluorenylmethoxycarbonyl (Fmoc), phenoxyacetyl (Pac), 4-tert-butylphenoxy acetyl (Tac), isopropylphenoxyacetyl (iPrPac), N,N-dimethylformamidine, N,N-dibutylformamidine, N,N-dimethylacetamidine, N,N-diphenyl carbamate, or a thiourea protecting group or the like.

Some embodiments involve the synthesis of 2'-thionocarbamates, wherein a disiloxane protected nucleoside of formula (IV) can be reacted with 1,1'-thiocarbonyldiimidazole in acetonitrile in the presence of a catalytic amount of 4-(dimethyl)aminopyridine (DMAP). The reaction described above may result in a quantitative, for example at least 95%, at least 98%, at least 99%, at least 99.5% or at least 99.9% conversion of the protected nucleoside to the imidazole thionocarbamate having a structure of Formula V and may give a crystalline product.

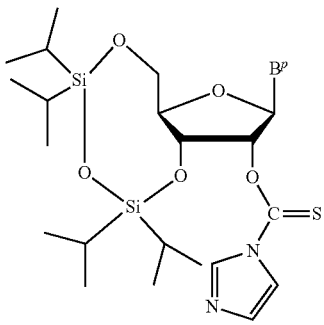

V

Disclosed herein is the reaction of a compound of Formula V with 1.1 equivalents of ammonia, a primary, or a secondary amine in acetonitrile with a catalytic amount of 4-(dimethyl)aminopyridine; wherein the reaction may result in a quantitative or near quantitative conversion, for example at least 95%, at least 98% or at least 99% conversion to the 2'-thionocarbamate derivative. In the case of aniline or other weak nucleophiles, one equivalent of 4-(dimethyl)aminopyridine may be used to achieve complete conversion to the corresponding thionocarbamate derivative. In the case of weak nucleophiles that are sterically constrained, such as dicyanoethylamine, the reaction may employ refluxing conditions in acetonitrile, overnight, with one equivalent of 4-(dimethyl)aminopyridine and the resulting product may be isolated in 70% yield.

Also disclosed herein is the protection of 5'(or 3')-hydroxyl, followed by 3'(or 5') phosphitylation. The 3',5'-tetraisopropyldisiloxane-2'-thionocarbamate protected nucleoside may be converted to active RNA synthesis monomers by first removing the 3',5'-tetraisopropyldisiloxane protecting group with 15 eq. to 40 eq. of HF/pyridine to produce the 2'-thionocarbamate-ribonucleoside intermediate. This intermediate may then be reacted with dimethoxytrityl chloride (DMTrCl) with 5 eq. to 10 eq. of collidine or N-methylimidazole (NMI) to produce a 5'-O-dimethoxytrityl(DMT)-2'-thionocarbamate-ribonucleoside derivative; that product may then be reacted with a phosphytilating reagent selected from: NC—CH$_2$—CH$_2$—O—P(Cl)—N(iPr)$_2$ or [N,N-(diisopropyl)amino]methoxychlorophosphine to produce a 5'-O-DMT-2'-thionocarbamate-ribonucleoside-3'-O-methyl(-or 2-cyanoethyl) phosphoramidite.

In some embodiments, wherein 5' to 3' oligonucleotide synthesis is desired, a modification of the method described above may be used to prepare a 3'-O-DMT-2'-thionocarbamate-ribonucleoside-5'-O-methyl(-or 2-cyanoethyl) phosphoramidite (for example by the following steps: a. protection with TIPS; b. 2'-thionocarbamate formation; c. removal of TIPS; d. phosphitylation of 5'OH; e. tritylation of 3'OH; or a. protection with TIPS; b. 2'-thionocarbamate formation; c. removal of TIPS d. protection of 5'-OH with TBDMS; e. tritylation of 3'-OH; f removal of TBDMS; g. 5'-OH phosphitylation.

The following 2'-thionocarbamate-uridine-3'-phosphoramidites were synthesized according to the above described procedure and incorporated into a U$_{2'C(S)R}$T$_{15}$ oligonucleotide. These 2'-C(S)R protecting groups were subsequentally evaluated for their ability to be deprotected by treatment of the oligonucleotide with 1,2-diaminoethane, for 2 hours at room temperature (Table 1).

TABLE 1

| 2'-protecting group | Structure | Lability with 1,2-diaminoethane |
|---|---|---|
| 1,1-dioxo-1λ$^6$-thiomorpholine-4-carbothioate | (structure) | ++++ |
| N-sulfonylpiperizine carbothioate | (structure) | ++++ |
| primary thionocarbamate | (structure) | +++ |

TABLE 1-continued

| 2'-protecting group | Structure | Lability with 1,2-diaminoethane |
|---|---|---|
| 2-acetamidoanilinecarbothioate | (structure) | +++ |
| anilinecarbothioate | (structure) | +++ |
| morpholinecarbothioate | (structure) | ++ |
| di(cyanoethyl)aminocarbothioate | (structure) | ++ |
| thiomorpholinecarbothioate | (structure) | + |
| cyanoethylaminocarbothioate | (structure) | + |
| trifluoromethylethylaminocarbothioate | (structure) | + |
| phenoxyethylaminocarbothioate | (structure) | + |

TABLE 1-continued

| 2'-protecting group | Structure | Lability with 1,2-diaminoethane |
|---|---|---|
| methoxyethylaminocarbothioate | —O–C(=S)–NH–CH₂CH₂–O–CH₃ | + |
| methylaminocarbothioate | —O–C(=S)–NH–CH₃ | + |
| dimethylaminocarbothioate | —O–C(=S)–N(CH₃)₂ | + |

Nucleic Acid Synthesis Using Thionocarbamate Protecting Groups

In some embodiments, solid phase synthesis of oligoribonucleotides follows the same cycle as DNA synthesis. A solid support with an attached nucleoside is subjected to removal of the protecting group on the 5'-hydroxyl. The incoming phosphoramidite is coupled to the growing chain in the presence of an activator. Any unreacted 5'-hydroxyl is capped and the phosphite triester is then oxidized to provide the desired phosphotriester linkage. The process is then repeated until an oligomer of the desired length results. The actual reagents used may vary depending on the 5'- and 2'-protecting groups. Other ancillary reagents may also differ.

In some embodiments the 2'-thionocarbamate nucleotide monomers described herein can be used to synthesize nucleic acids that comprise one or more ribonucleotide residues. The synthesis may be performed in either direction: from 3' to 5' or from 5' to 3'. For example, in the 3' to 5' direction, a first nucleoside monomer with a 5'-OH is coupled, in the presence of an activator (for example, tetrazole or S-ethylthio-tetrazole), with a nucleotide monomer having a 3'-phosphoramidite and a 5'-protecting group (typically DMT). The first nucleoside monomer is optionally bound to a solid support, for example through a succinimidyl linker on the 3'-hydroxy. Alternatively, the synthesis can be performed in solution. After the coupling step, in which the 5'-OH and the 3'-phosphoramidite condense to form a phosphite triester linkage and result in a dinucleotide, the unreacted 5'-hydroxyls of the first nucleoside monomer may be optionally capped with acetic anhydride solution either prior to and/or after oxidation. During oxidation, the phosphite triester linkages are oxidized either with a solution containing iodine or with a sulfurization agent, when a phosphorothioate linkage is desired. The 5'-DMT protecting group is then removed (deprotection) with an anhydrous acid solution; for example, 3% of trichloroacetic acid (TCA) in methylene chloride or 5%-10% dichloroacetic acid (DCA) in toluene. The newly formed dinucleotide is then ready for coupling with another nucleotide monomer having a 3'-phosphoramidite and a 5'-DMT protecting group. These steps may be repeated until the nucleic acid reaches the desired length and/or sequence.

In some embodiments, the 2'-thionocarbamate nucleotide monomers having a 3'-H-phosphonate as in the structure of formula VI can be used to synthesize nucleic acids, that comprise one or more ribonucleotide residues; where $R^1$ is a hydroxyl protecting group, $B^p$ is a heterocycle or protected heterocycle, and PG is a thionocarbamate protecting group.

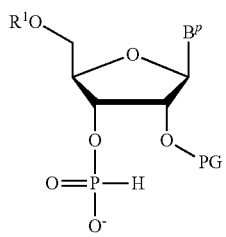

VI

For example, in the 3' to 5' direction, a first nucleoside monomer with a 5'-OH is coupled, in the presence of an activator (for example, adamantane carbonyl chloride) with a nucleotide monomer having a 3'-H-phosphonate and a 5'-protecting group (typically DMT). The first nucleoside monomer is optionally bound to a solid support, for example through a succinimidyl linker on the 3'-hydroxy. Alternatively, the synthesis can be performed in solution. After the coupling step, in which the 5'-OH and the 3'-H-phosphonate condense to form a H-phosphonate linkage and result in a dinucleotide, the unreacted 5'-hydroxyl groups of the first nucleoside monomer are capped with a capping reagent (such as, but not limited to, isopropyl phosphite in the presence of adamantane carbonyl chloride). The 5'-DMT protecting group is then removed (deprotection) with an anhydrous acid solution; for example, 3% of trichloroacetic acid (TCA) in methylene chloride, or 5%-10% dichloroacetic acid (DCA) in toluene. The newly formed dinucleotide is then ready for coupling with another nucleotide monomer having a 3'-H-phosphonate and a 5'-DMT protecting group. These steps may be repeated until the nucleic acid reaches the desired length and/or sequence. The fully protected oligonucleotide comprising at least one ribonucleotide is then reacted with an oxidizing solution comprising iodine and N-methylmorpholine to oxidize all at once all the H-phosphonate linkages into phosphodiester linkages or with a solution comprising a sufurization reagent to produce all at once phosphorothioate linkages.

In some embodiments, thionocarbamate protections on the 2'-hydroxyl enable the synthesis of long sequences of RNA because of the ease and efficiency of removing these protecting groups. The nucleic acids synthesized by some embodiments of the methods disclosed herein may be as long as 20, 25, 30, 35, 40, 45, 50, 55, 60, 65, 70, 75, 80, 85, 90, 95, 100, 105, 110, 115, 120, 125, 130, 135, 140, 145, 150, 200 or 500 nucleotides in length or longer. Furthermore, a nucleic acid synthesized according to some embodiments can be combined with another nucleic acid to form longer nucleic acids. For example, a nucleic acid of 70 bases can be coupled with another nucleic acid of 70 bases by chemical ligation. As another example, two nucleic acids can be ligated with an RNA ligase wherein the 2'-protecting groups may be removed before ligation.

The synthetic methods described herein may be conducted on a solid support having a surface to which chemical entities may bind. In some embodiments, multiple oligonucleotides being synthesized are attached, directly or indirectly, to the same solid support and may form part of an array. An "array" is a collection of separate molecules of known monomeric sequence each arranged in a spatially defined and a physically addressable manner, such that the location of each sequence is known. The number of molecules, or "features," that can be contained on an array will largely be determined by the surface area of the substrate, the size of a feature and the spacing between features, wherein the array surface may or may not comprise a local background region represented by non-feature area. Arrays can have densities of up to several hundred thousand or more features per cm$^2$, such as 2,500 to 200,000 features/cm$^2$. The features may or may not be covalently bonded to the substrate. An "array," or "chemical array' used interchangeably includes any one-dimensional, two-dimensional or substantially two-dimensional (as well as a three-dimensional) arrangement of addressable regions bearing a particular chemical moiety or moieties (such as ligands, e.g., biopolymers such as polynucleotide or oligonucleotide sequences (nucleic acids), polypeptides (e.g., proteins), carbohydrates, lipids, etc.) associated with that region. An array is "addressable" when it has multiple regions of different moieties (e.g., different polynucleotide sequences) such that a region (i.e., a "feature" or "spot" or "well" of the array) at a particular predetermined location (i.e., an "address") on the array will detect a particular target or class of targets (although a feature may incidentally detect non-targets of that feature). Array features are typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "probe" may be the one which is to be evaluated by the other (thus, either one could be an unknown mixture of analytes, e.g., polynucleotides, to be evaluated by binding with the other).

An array of polynucleotides, as described herein, may include a two or three-dimensional array of beads. In certain cases, the beads are linked to an oligonucleotide that has two portions, a first portion that binds to a target, and a second portion that contains a nucleotide sequence that identifies the oligonucleotide. In other cases, the bead may provide an optical address for the oligonucleotide, thereby allowing the identity of the oligonucleotide to be determined.

In one embodiment, the array may be in the form of a 3-dimensional multiwell array such as the Illumina BeadChip. One embodiment of BeadChip technology is the attachment of oligonucleotides to silica beads. The beads are then randomly deposited into wells on a substrate (for example, a glass slide). The resultant array is decoded to determine which oligonucleotide-bead combination is in which well. The decoded arrays may be used for a number of applications, including gene expression analysis and genotyping. Gene expression analysis may be performed using, for example, a 50-200 oligonucleotide that has two segments. For example, a 50-150 base segment at one end of the oligonucleotide may be designed to hybridize to a labeled target sequence. The other end of the oligonucleotide may serve as the address. The address is a unique sequence to allow unambiguous identification of the oligonucleotide after it has been deposited on the array. Bead Arrays may have, for example, 1,000 to 1,000,000 or more unique oligonucleotides. Each oligonucleotide may be synthesized in a large batch using standard technologies. The oligonucleotides may then be attached to the surface of a silica bead, for example a 1-5-micron bead. Each bead may have only one type of oligonucleotide attached to it, but have hundreds of thousands of copies of the oligonucleotide. Standard lithographic techniques may be used to create a honeycomb pattern of wells on the surface, for example a glass slide. Each well may hold a bead. The beads for a given array may be mixed in equal amounts and deposited on the slide surface, to occupy the wells in a random distribution. Each bead may be represented by, for example, about 20 instances within the array. The identity of each bead may be determined by decoding using the address sequence. A unique array layout file may then associated with each array and used to decode the data during scanning of the array.

In some embodiments, oligonucleotides being synthesized may be attached to a solid support (for example: beads, membrane, 96-well plate, array substrate, filter paper and the like) directly or indirectly. Suitable solid supports may have a variety of forms and compositions and derive from naturally occurring materials, naturally occurring materials that have been synthetically modified, or synthetic materials. Examples of suitable support materials include, but are not limited to, CPG, silicas, teflons, glasses, polysaccharides such as cellulose, nitrocellulose, agarose (e.g., Sepharose® from Pharmacia) and dextran (e.g., Sephadex® and Sephacyl®, also from Pharmacia), polyacrylamides, polystyrenes, polyvinyl alcohols, copolymers of hydroxyethyl methacrylate and methyl methacrylate, and the like. The initial monomer of the oligonucleotide to be synthesized on the solid support, e.g. CPG, bead, or array substrate surface, can be bound to a linking moiety (for example, a succinyl linker, or a hydroquinone —O,O'-diacidic acid called a "Q-linker", an oxalyl linker, and the like) which is in turn bound to a surface hydrophilic group, e.g., a surface amine or a hydroxyl present on a silica substrate. In some embodiments, a universal linker is used (for example, Unylinker which is a succinyl derivative of 8,9-Dihydroxy-4-phenyl-10-oxa-4-aza-tricyclo[5.2.1.02,6]decane-3,5-dione, or other Glenn Research universal supports). In some embodiments, an initial nucleotide monomer is reacted directly with a reactive site, e.g. a surface amine or hydroxyl present on the substrate. In some embodiments wherein the initial nucleotide monomer is reacted directly with the reactive sites on the surface, the oligonucleotide remains covalently attached to the surface post-oligonucleotide synthesis and deprotection, after all of the protecting groups are removed. In some embodiments, a nucleotide monomer is reacted with a non-nucleoside hydroxyl or amine that is not part of a nucleoside or nucleotide. Alternatively, in some embodiments, an oligonucleotide comprising a ribonucleotide residue can be synthesized first and then attached to a solid substrate post-synthesis by any suitable method. Thus, particular embodiments can be used to prepare an array of oligonucleotides and/or oligonucleotides comprising a ribonucleotide residue wherein the oligonucleotides and/or oligonucleotides comprising a ribonucleotide residue are either synthesized on the array, or attached to the array substrate post-synthesis.

With the efficiency and ease of some methods described herein, oligonucleotide, comprising at least one ribonucleotide, synthesis can be performed in small or large scales. The quantity of oligonucleotide made in one complete run of a particular method (in one container) can thus be less than a microgram, or in micrograms, tens of micrograms, hundreds of micrograms, grams, tens of grams, hundreds of grams, or even kilograms.

As such, some embodiments described herein include methods of synthesizing nucleic acids that comprise the steps of providing a nucleotide residue or a nucleoside monomer having an unprotected hydroxyl group; and a nucleotide monomer with a 2'-thionocarbamate protecting group; and contacting the nucleotide residue or nucleoside monomer with the 2'-thionocarbamate protected nucleotide monomer under conditions sufficient to covalently bond the 2'-thionocarbamate protected nucleotide monomer to the nucleotide residue or nucleoside monomer to produce a nucleic acid. Some embodiments herein describe a single monomer addition step of the synthesis protocol, where the above process may be reiterated with additional monomers as desired to produce a polymer of desired length and sequence. Optional capping steps may be performed, for example, either prior to and/or after an oxidation step, where unreacted hydroxyls of the first nucleotide residue or nucleoside monomer may be capped, for example with acetic anhydride solution. These additional monomers may be 2'-thionocarbamate protected monomers or protected 2'-deoxy-monomers or non natural protected monomers, i.e. modified monomers (for example: 2'-fluoro 2'-O-methyl, 2'-methyloxyethyl (2'-MOE), 2'-Locked Nucleic Acid (2'-LNA) etc.; where the modification can be anywhere on the nucleotide structure including the base, as described in the definition of modified nucleotides). Such incorporation of modified nucleotides provides a variety of modified polynucleotides.

In some embodiments where phosphorothioate linkages are desired in polynucleotides, for example, RNA or a polynucleotide comprising a ribonucleotide residue, sulfurization solutions can be used in lieu of the oxidation solutions used to form a phosphodiester internucleotide bond, in the oxidation steps of the synthetic methods described herein. The term "oxidation" or "oxidized" may be applied in both cases of producing a phosphate or a phosphorothioate linkage, where the oxidation state of the phosphorus changes. A number of sulfur transfer reagents have been used to synthesize oligonucleotides containing phosphorothioate linkages that include for example, elemental sulfur, dibenzoyl tetrasulfide, 3-H-1,2-benzidithiol-3-one 1,1-dioxide (also known as Beaucage reagent), tetraethylthiuram disulfide (TETD), bis(O,O-diisopropoxy phosphinothioyl) disulfide (known as Stec reagent) and phenyl acetyl disulfide (also known as PADS). The introduction of phosphorothioate moieties into oligonucleotides, assembled by solid-phase synthesis, can be achieved using, for example, an H-phosphonate approach or a phosphoramidite approach. The H-phosphonate approach involves a post-synthesis process, carried out after the desired sequence has been assembled, to convert all of the internucleotide linkages to phosphorothioates. Alternatively, the phosphoramidite method allows the sulfurization to take place independently at each cycle in the oxidation step giving a choice to synthesize a normal phosphodiester internucleotide linkage, or to introduce a phosphorothioate at a specific position in the sequence. An advantage of using phosphoroamidite chemistry, therefore, is the capability to control the state of each linkage in a site specific manner.

RNA Deprotection

Today, RNA deprotection is performed in a specific manner and the steps involved in deprotection of the different protecting groups attached to different moieties (phosphates, nucleobases and 2'-hydroxyl) of a fully protected synthetic RNA follow a specific order. This may be a two-step process that entails cleavage of the oligomer from the support and deprotection of the base and phosphate blocking groups (in one step), followed by removal of the 2'-protecting groups. Occasionally, a different order of reactions or separate deprotection of the phosphate groups is required (when the phosphate is for example protected with a methyl group and not a cyanoethyl group). Because of the instability of the RNA internucleotide linkage at basic pH as discussed below, and because of the basic conditions required to remove the phosphate protecting groups, the nucleobase protecting groups and to cleave the oligoribonucleotide from the support, the 2'-protecting group is removed at last as reported in known prior art.

RNA may undergo cleavage and degradation under basic conditions, via a transesterification reaction involving the 2'-hydroxyl group. [Journal of Organic Chemistry, 1991. 56(18): p. 5396-5401; Journal of the American Chemical Society, 1999. 121(23): p. 5364-5372; Chemical Reviews, 1998. 98(3): p. 961-990.]. The pKa of a 2'-hydroxyl of RNA in aqueous solution can vary depending on salt concentration and base sequence, but is typically around 13. [Journal of the American Chemical Society, 2001. 123(12): p. 2893-2894; J Org Chem, 2003. 68(5): p. 1906-10.] The pKa of (protonated) ammonia is about 9.2, which means that a concentrated aqueous ammonium hydroxide solution sometimes used for removing protecting groups from synthetically prepared oligonucleotides has a pH of greater than 12. At these high pH's, a significant amount of the 2'-hydroxyl is deprotonated, and a base catalyzed transesterification reaction may result in backbone cleavage (Scheme 2). The reaction described above is generally believed to proceed through an intermediate or transition state as shown in Scheme 2.

Scheme 2

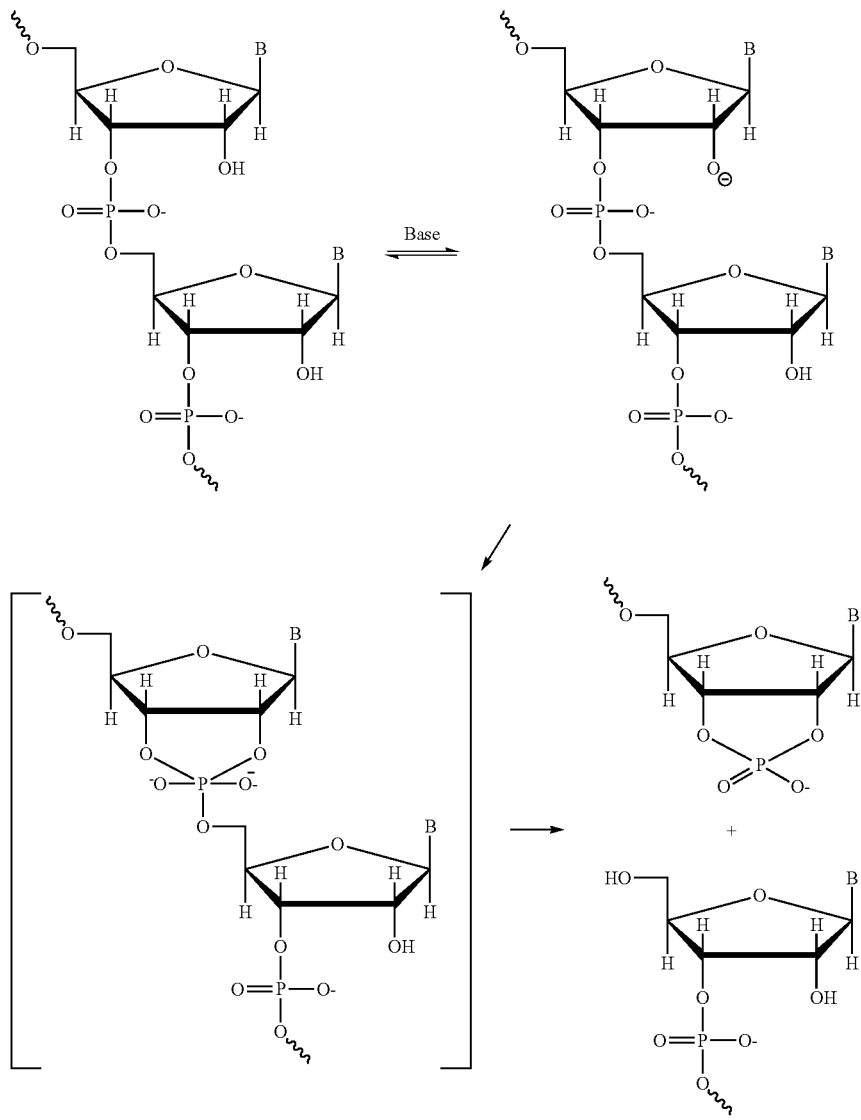

Stronger bases such as methylamine (pKa 10.6) or triethylamine (pKa 10.6) may, under typical aqueous conditions, promote RNA backbone cleavage even more readily than ammonia. Oligonucleotide synthesis sometimes uses protecting groups on the heterobases that are removed with a composition including an amine base, such as ammonia or methylamine. In the case of RNA, the 2'-hydroxyl protection needs to be intact during the above procedure to avoid the base catalyzed backbone cleavage.

However, the pKa's previously described for amine bases and the 2'-hydroxyls are for aqueous conditions. The ionization constants of weak acids and bases can be substantially altered in the presence of organic solvents [J Biochem Biophys Methods, 1999. 38(2): p. 123-37.]. Acidities of organic molecules in dipolar aprotic solvents, particularly in dimethylsulfoxide, have been widely studied. Acetic acid, which has a pKa of 4.7 in water, is a much weaker acid in DMSO, with a pKa of 12.3. Methanol, which has a pKa in water of about 15, has a pKa of ~28 in DMSO. For a neutral compound ionizing to a charged anionic species (such as a hydroxyl group ionizing to an alkoxy anion), decreasing the dielectric of a solvent in general results in a decrease in the acid equilibrium constant (increase in pKa) for the following equilibrium:

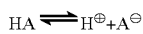

Thus the pKa of phenol is about 10 in water (dielectric constant=78), while in DMSO (dielectric constant=47) the pKa is about 16, and in acetonitrile (dielectric constant=36) the pKa is approximately 27[J. Phys. Chem., 1965. 69(9): p. 3193-3196; J. Am. Chem. Soc., 1968. 90(1): p. 23-28; Journal of Organic Chemistry, 2006. 71(7): p. 2829-2838], a change of 16 orders of magnitude. Hence in acetonitrile phenol is a very weak acid (the corresponding anion is a very strong base). It should be recognized that the dielectric strength of a solvent is not the only variable that can affect the pKa of a compound. Solvent basicity, polarity, hydrogen bonding, and other specific and non-specific interactions can affect the solvation capability of a solvent and can have a significant effect on the pKa of dissolved solutes.

For a charged compound dissociating to a neutral compound, such as the dissociation of a protonated amine,

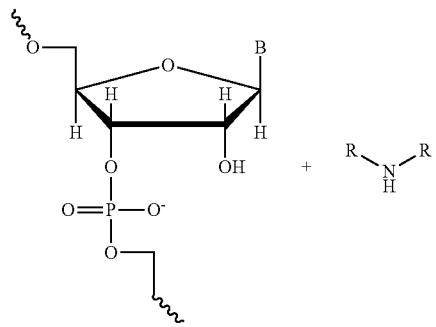

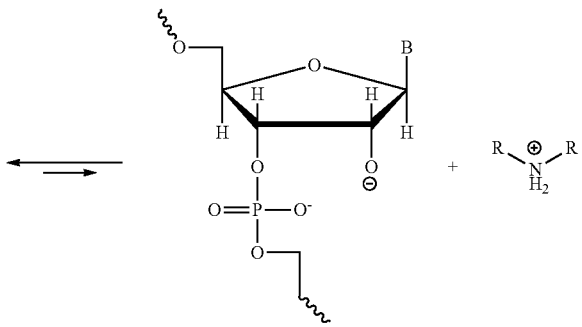

over 10 orders of magnitude, suggesting that degradation of RNA may not occur at an appreciable rate.

decreasing the dielectric of a solvent in general may result in relatively small changes in pKa.

Thus the pKa of (protonated) triethylamine in water is about 11, while in DMSO the pKa is about 9, and in acetonitrile the pKa is about 18. In acetonitrile, triethylamine is a somewhat stronger base than in water (delta pKa going from water to acetonitrile is ~7) while in DMSO it is actually a weaker base.

An evaluation is described herein whether RNA having an appropriate base-labile 2'-protecting group can be 2'-deprotected using amines in organic solvent, in gas-phase or neat. The base catalyzed mechanism for the degradation of RNA depends on the ability of the base to deprotonate the hydroxyl to a sufficient extent such that the cyclization and cleavage reaction can occur at a significant rate. In the case of aqueous solutions of amine bases deprotonating the 2'-hydroxyl, there is a difference of about 3 or 4 pKa units, which is close enough so that concentrated solutions of amine bases can significantly deprotonate the hydroxyl resulting in internucleotide bond cleavage. However, when organic solvents are used, the pKa of the 2'-hydroxyl is increased significantly more than that of the amine base. This trend can also be observed in the use of gas-phase amines or neat liquid amines. This suggests that ordinary amines such as ammonia or methylamine, which in water are strong enough bases to deprotonate the 2'-hydroxyl and cause substantial RNA degradation, may cause significantly less degradation when used in solvents such as acetonitrile or toluene, or when used in gas phase or as neat liquids. In fact, it has been reported that amine bases in acetonitrile should not be strong enough to appreciably deprotonate phenol. Even though ammonia becomes a stronger base in acetonitrile (pKa of conjugate acid increases from 9.2 to 16.5 when going from water to acetonitrile, a delta pKa of ~7) [J. Am. Chem. Soc., 1968. 90(1): p. 23-28.], phenol becomes a relatively much weaker acid, with the pKa increasing from about 10 to 27 (delta pKa ~17). The acid base pair of phenol and ammonia, which in water have a pKa difference of less than one pKa unit, in acetonitrile have a pKa difference of about 10 pKa units. The actual pKa in acetonitrile of an aliphatic hydroxyl such as the 2'-hydroxyl of RNA is increased to a point where it is difficult to measure (calculation gives a pKa of about 35). In gas-phase, neat amines, or in acetonitrile and many other organic solvents, the solvent mediated equilibrium between amine bases and aliphatic alcohols are in favor of the two neutral species by Exposing RNA to non-aqueous solutions of amine bases may thus be a practical method of performing deprotection of RNA of both the exocyclic amine protecting groups as well as the 2'-hydroxyl protecting group that are base-labile. The nucleophilicity of the amine bases, and hence the deprotection rate may be enhanced under these conditions. The deprotection of the exocyclic amines and the 2'-hydroxyl may be performed simultaneously or sequentially. So long as the solutions do not contain enough water to significantly change the favorable pKa differential of the amines and hydroxyls, with the appropriate choice of protecting groups and amine the degradation of the RNA will be slow relative to the rate of deprotection. Under these conditions it may also be possible to cleave a solid support linker, thus performing deprotection of the RNA oligonucleotide and cleavage from the solid support simultaneously. Under some of these conditions the cleaved and deprotected oligonucleotide will be retained on the solid support, since typical RNA molecules are not soluble in many organic solvents or neat amines. By retaining the oligonucleotide on the solid support it is possible to flush the deprotection reagents from the column, wash with anhydrous solvent to remove the excess of the amine solution and residual deprotection products, and then isolate the desired oligonucleotide product by eluting it from the support with water, an aqueous buffer, a mixture of water or an aqueous buffer and an organic solvent, a chromatographic mobile phase, a mixture of an aqueous buffer and a chromatographic mobile phase, or any solvent system which will solubilize the oligonucleotide and remove it from the solid support. In this embodiment the deprotection and isolation of the desired RNA product may be performed in a completely automated fashion on a commercial DNA/RNA synthesizer.

Retaining a DNA or RNA oligonucleotide on a solid support during deprotection by the use of a gas-phase amine (Kempe U.S. Pat. No. 5,514,789), anhydrous neat amine or an anhydrous amine dissolved in an organic solvent was described by Kempe in the U.S. Pat. No. 5,750,672. However, in all cases, Kempe describes the need to deprotect the 2'-hydroxyls of RNA in a subsequent step after the amine treatment due to the well known cleavage of RNA in the presence of basic amines.

Described herein is the screening of a number of amines for their ability to deprotect RNA oligonucleotides containing a base labile 2'-protecting group while simultaneously deprotecting the heterobase protecting groups. The amine reagents may be, for example, in gas-phase, neat, or in solutions of organic solvents. In some cases, the time required to achieve complete deprotection may result in some cleavage of the RNA internucleotide bond, presumably by the base catalyzed route shown in Scheme 2. As disclosed herein, 1,2-diaminoethane, is particularly effective in both removing a 2'-hydroxyl thionocarbamate protecting group, as well as removing the standard exocyclic amine base protecting groups and cleaving the succinate linker that links the synthetic oligonucleotide to the resin. This may occur quickly, and with little or no RNA backbone fragmentation or formation of undesirable, stable transcarbamoylation products obtained from the partial deprotection of the thionocarbamate groups. The effect of water content in neat 1,2-diaminoethane and organic solvent solutions of 1,2-diaminoethane is discussed herein. For example, neat diamine or solvent solutions of diamine do not need to be anhydrous, and that in certain embodiments, up to 20% water content can be tolerated before RNA cleavage occurs at unacceptable levels. In certain embodiments it may be advantageous to keep the water content below the level whereby the RNA product is dissolved in the deprotection solution. In certain cases the amount of water is dependent upon the solvent properties of the deprotection composition comprising for example, 1, 2-diaminoethane, other 1,2-diaminoethane derivatives or other diamines and optionally one or more solvents. With polar solvents like acetonitrile, the diamine composition can tolerate lower amounts of water compared to using non-polar solvents like toluene. A diamine composition may contain less than 20% water. The deprotection may be done under conditions that comprise less than 20% water, e.g. less than 15%, less than 10%, less than 5%, or less than 1%. For example, contained with a deprotection solution comprising a diamine and less than 20% water, e.g. less than 15%, less than 10%, less than 5%, or less than 1%. In certain embodiments, a diamine composition comprising <20% of water, may also comprise other amines, scavengers, reagents, solvents and mixtures thereof as described herein.

There are many variations by which a synthetic RNA protected with 2'-thionocarbamate protecting groups or base-labile protecting groups can be deprotected.

Some embodiments described herein feature two variations of the process in which an oligonucleotide comprising one or more ribonucleotide residues protected with 2'thionocarbamate groups is deprotected.

In a particular embodiment is a first variation: In this variation, the deprotection process is accomplished in a two step process, 1) removal of the phosphate protecting groups, 2) removal of the nucleobase protecting groups, removal of the 2'-thionoprotecting groups and cleavage of the linker, for example, a succinate linker that releases the oligonucleotide from the solid support.

1) Phosphate deprotection: when the beta-cyanoethyl group (CNE) is employed as the phosphate protecting group, the phosphate deprotection is accomplished by exposing the oligonucleotide comprising one or more protected ribonucleotide residues to a solution of non nucleophilic amine such as for example, but not limited to diethylamine (DEA) for an hour at room temperature. Alternatively, the CNE protecting group can be removed with t-butylamine or DBU. Alternatively, the phosphate deprotection can be also carried out with gaseous ammonia or methylamine or solutions of non aqueous ammonia or methylamine in anhydrous solvents at room temperature for a short period of time, not exceeding an hour. When methyl is used as the phosphate protecting group, the oligonucleotide is reacted with a reagent, for example, thiophenol or disodium 2-carbamoyl-2-cyanoethylene-1, 1-dithiolate in DMF for 30 minutes at room temperature.

2) Concurrent deprotection of exocyclic amine on the nucleobases (for example, $N^6$-benzoyl-A, $N^6$-isobutyryl-A, $N^4$-acetyl-C or $N^4$-isobutyryl-C, $N^2$-isobutyryl-G) and 2'-hydroxyl protected with a thionocarbamate, for example, a 2'-O-(1,1-dioxo-1$\lambda^6$-thiomorpholine-4-carbothioate) and cleavage of the oligonucleotide from the support. For example, subsequent to the phosphate deprotection, the partially protected oliogonucleotide comprising one or more ribonucleotide residues protected with a 2'-thionocarbamate is reacted with neat 1,2-diaminoethane for 2 hours at room temperature resulting in the removal of the nucleobase protecting groups (for example, acetyl, isobutyryl and benzoyl), removal of the 2'-protecting group, and the cleavage of a fully deprotected oligoucleotide from the support. Because of its insolubility in 1,2-diaminoethane, the fully deprotected oligonucleotide remains adsorbed onto the column. Optionally, a wash with an organic solvent, such as acetonitrile is performed to flush out short sequences and organic residues obtained from the deprotection reaction. Subsequently, the oligonucleotide is eluted from the column or solid support, for example with water, aqueous buffer or mobile phase for chromatography.

In particular embodiments of the deprotection methods described above, the oligonucleotide can be reacted with a deprotection composition comprising a 1,2 diaminoethane or derivatives thereof, such as but not limited to, neat 1,2 diaminoethane or a solution (with water content not exceeding 20% v/v) of 1,2-diaminoethane in an organic solvent or mixtures of solvents, for example acetonitrile, THF, 2-methyl-THF or toluene. In particular embodiments, the oligonucleotides can be treated with a composition comprising 1,2-diaminoethane or a derivative thereof, and an amine, a base or mixtures thereof.

Some embodiments herein describe a RNA synthesis process that enables a streamlined post-synthesis deprotection and purification of the oligonucleotide. Synthesis of RNA or a polynucleotide comprising one or more ribonucleotide residues by the process described above can be fully automated.

In a particular embodiment is a second variation: This second variation features a single step process that yields a cleaved and fully deprotected oligonucleotide comprising one or more ribonucleotide residues. The oligonucleotide may comprise one or more ribonucleotide residues with a 2'-thionocarbamate protecting group (for example a 2'-O-(1,1-dioxo-1$\lambda^6$-thiomorpholine-4-carbothioate), protected with beta-cyanoethyl on the phosphate and standard protecting groups on the nucleobase (for example, acetyl or isobutyryl for C, benzoyl for A and isobutyryl for G); and attached to the solid support through a linker, for example a succinate linker; and is incubated in a diamine composition, for example, neat 1,2-diaminoethane for 2 hours at room temperature. As described above, the solid support may then be washed with an organic solvent such as acetonitrile and subsequently the oligonucleotide may be eluted from the column, for example with water, an aqueous buffer or a mobile phase used for chromatography.

In particular embodiments of the deprotection methods described above, the oligonucleotide can be reacted with a deprotection composition comprising a 1,2 diaminoethane or derivatives thereof, as described herein.

In some embodiments treatment of an oligonucleotide with a diamine deprotection composition, for example, a 1,2-diaminoethane, or 1,2-diaminopropane deprotection composition can lead to the formation of a small amount of ammonium complexes with the deprotected RNA, resulting in a higher mass product as observed by mass spectrometry analysis. It is possible to reverse this complex formation to the expected product by using well known protocols, including but not limited to ammonium exchange with a sodium bromide, sodium chloride, sodium acetate or a sodium phosphate buffer, at room temperature or at approximately 30-70° C. for up to several hours, followed by ethanol precipitation or isolation by ion-exchange chromatography, reverse phase chromatography, gel filtration, or membrane separation techniques. It is understood that the salt exchange step described above can be performed at any time post-oligonucleotide deprotection, directly after 1,2-diaminoethane deprotection before eluting the oligonucleotide off of the solid support; or after eluting the oligonucleotide from the solid support.

Deprotection of RNA having non base-labile 2'-protecting groups (TBDMS, TOM and ACE). In the past, deprotection of oligoribonucleotides was a two step process in which the base and phosphate groups were removed and the oligomer was cleaved from the support in a similar procedure to that used for the deprotection of DNA. The initial step was accomplished in 1-4 hours at 55° C. with 3/1 NH$_4$OH/EtOH. More recently, faster deprotection protocols, entailing the use of aqueous methylamine have been reported for RNA (Usman et al., U.S. Pat. No. 5,804,683; Wincott et al., 1995, supra; Reddy et al., 1995, *Tetrahedron Lett.*, 36, 8929-8932). Incubation times have been reduced to 10 min at 65° C. When compared with other RNA deprotection methods, treatment with this reagent gave greater full length product than the standard protocol using 3/1 NH$_4$OH/EtOH (Wincott et al., 1995, supra). The only requirement is that acetyl be used as the N-protecting group for cytidine because of a well-documented transamination reaction (Reddy et al., 1994, *Tetrahedron Lett.*, 35, 4311-4314).

The second step was then to remove the 2'-protecting groups and the reagents used to accomplish this deprotection depended on the 2'-protected group used, for example, t-butyldimethylsilyl (TBDMS, Ogilvie et al. 1979), triisopropylsilyloxymethyl (TOM, Pitsch et al. 1998) and bis(2-acetoxyethoxy)methyl (ACE, Scaringe et al.). TBDMS and TOM both contain silyl moieties which are cleaved in the presence of fluoride ions; and ACE, which is an orthoester protecting group removed in acidic conditions. In all cases, the 2'-protecting group is removed last to avoid the internucleotide cleavage that would occur if the 2'-protecting group was removed prior to treatment with strong amine base solution.

In the past, 2'-TBDMS removal was accomplished with 1 M tetrabutyl ammonium fluoride (TBAF) in THF at room temperature over 24 hours (Usman et al., 1987, J. Am. Chem. Soc., 109, 7845-7854; Scaringe et al., 1990, Nucleic Acids Research, 18, 5433-5341). Some reports have been published regarding the use of neat triethylamine trihydrofluoride (TEA.3HF) (Duplaa et al., U.S. Pat. No. 5,552,539; Gasparutto et al., 1992, Nucleic Acids Research, 20, 5159-5166; Westman et al., 1994, Nucleic Acids Research, 22, 2430-2431) as a desilylating reagent. Also, a mixture of TEA.3HF in combination with N-methylpyrrolidinone (NMP) (Usman and Wincott, U.S. Pat. No. 5,831,071; Wincott et al., 1995, supra) or DMF (Sproat et al., 1995, supra) has also been described in which deprotection can be achieved in 30-90 min at 65° C. or 4-8 h at room temperature. TOM deprotection can use 1 M TBAF in THF and the hemiacetal cleavage occurs with the addition of 1M tris buffer. ACE deprotection may occur after incubation with a buffer comprising acetic acid and tetramethylethylenediamine (TEMED). In some embodiments described herein is a method for deprotecting oligonucleotides containing non-base labile 2'-protecting groups such as but not limited to, TBDMS, TOM and ACE. Such a method is an improvement over past methods, in that it enables the isolation of a "clean", fully deprotected RNA, rid of any residual cleaved protecting groups, excess reagents and salts as it has been done previously with DNA. In some embodiments the method features the deprotection of such oligonucleotides wherein the 2'-protecting groups are removed prior to the removal of the nucleobase protecting groups. In a particular embodiment, the method entails a three step process where the oligonucleotide remains attached or associated with the solid support.

First step; the beta-cyanoethyl phosphate protecting groups are removed with a non-nucleophilic or hindered amine such as, but not limited to diethylamine or t-butylamine at room temperature for an hour. Alternatively a suitable base such as DBU for example, can be used leaving the oligonucleotide still attached to the solid support. Alternatively, if methyl groups are used instead of beta-cyanoethyl as phosphate protecting groups, the removal of the methyl groups is achieved using thiophenol or disodium 2-carbamoyl-2-cyanoethylene-1, 1-dithiolate in DMF for 30 minutes at room temperature. Following the phosphate deprotection, the solid support is washed with any suitable solvent to remove cleaved protecting groups and reagents.

Second step: Removal of the 2'-protecting groups. If a 2'-silyl protecting group such as 2'-TBDMS or 2'-TOM is used, the deprotection may be performed using TBAF (or TBAF and tris buffer for TOM) or HF/TEA; and wherein the oligonucleotide still attached to the support is optionally washed with a solvent to remove cleaved protecting groups and excess reagents (including salts).

Third step: Deprotection of nucleobases (N$^6$-benzoyl-A or N$^6$-isobutyryl-A, N$^4$-acetyl-C or N$^4$-isobutyryl-C, N$^2$-isobutyryl-G) and cleavage of oligonucleotide from support. The final step of this method may be accomplished by exposing the nucleobase-protected oligonucleotide to neat 1,2 diaminoethane for 2 hours at room temperature, resulting in the deprotection of protecting groups as well as cleavage of the linker (for example a succinate linker) to the solid support. The fully deprotected oligonucleotide comprised of one or more ribonucleotide residues may be washed with a solvent, for example acetonitrile, wherein the polynucleotide remains insoluble and adsorbed to the solid support, and optionally the oligonucleotide is then eluted with for example, water, buffer or mobile phase used in chromatography. Alternatively, the nucleobase protecting groups are phenoxyacetyl or t-butylphenoxyacetyl or dimethylformamidine, dimethylacetamidine and the like.

In particular embodiments of the method the oligonucleotide can be reacted with a deprotection composition comprising a diamine, a 1,2-diaminoethane or derivatives thereof, as described above. As noted above, a 1,2-diaminoethane deprotection composition can lead to the formation of a small amount of ammonium complexes with the deprotected RNA resulting in higher mass product (as shown by mass spectrometry analysis). It is possible to reverse this complex formation as described above, wherein salt exchange step can be performed at any time post-oligonucleotide deprotection.

In particular embodiments of a solid support bound oligonucleotide comprising a ribonucleotide residue deprotection method, provided that the oligonucleotide is attached to the solid support with a fluoride-labile linker or a photocleavable linker, the cyanoethyl phosphate protecting groups and the nucleobase protecting groups are removed with an amine reagent, for example, 1,2-diaminoethane or diamine reagent, resulting in a partially deprotected oligonucleotide. Subsequently, the 2'-protecting groups are removed with a suitable 2'-deprotecting reagent (for example TEA/3HF or TBAF to remove TBDMS or TOM, and thus the fluoride-labile linker; or an acid solution to remove ACE), and/or if the oligonucleotide is linked to the solid support through a photocleavable linker, exposing the fully deprotected oligonucleotide to a light source to cleave the photocleavable linker and release the deprotected oligonucleotide.

In some embodiments, after deprotecting the phosphate groups, the 2'-protecting groups are removed in an additional step with a solution comprising a diamine, for example 1,2-diaminoethane or substituted versions thereof as discussed herein, prior to exposing the partially deprotected RNA to another deprotecting reagent to further deprotect the RNA.

In particular embodiments a RNA oligonucleotide can be synthesized on a solid support with fluoride-labile 2'-protecting groups such as, but not limited to, tertiary-butyldimethylsilyl (TBDMS), triisopropylsilyloxymethyl (TOM), or (2-cyanoethyoxy)methyl (CEM) (Shiba et al. Nucleic Acids Symposium Series 50(1), pp 11, 2006). The phosphorus protecting group may then be removed using a thionucleophile reagent such as thiophenol or a non-nucleophilic or hindered amine reagent, such as diethylamine in acetonitrile. The 2'-silyl protecting group may then be removed from the oligonucleotide by reacting the support bound oligonucleotide with tetrabutylammonium fluoride, in THF, followed by washing with acetonitrile to remove the fluoride ion and retain the oligonucleotide on the support. The exocyclic amine protecting groups and solid support linker may then be deprotected and cleaved, respectively, with neat 1,2-diaminoethane for 2 hours at room temperature. The 1,2-diaminoethane is washed from the solid support with anhydrous acetonitrile. The RNA oligonucleotide may then be recovered from the solid support using water, an aqueous buffer or chromatographic mobile phase.

In certain embodiments an RNA oligonucleotide can be synthesized on a solid support with 2'-acid labile protecting groups such as, but not limited, to bis(2-acetoxy-ethoxy) methyl (ACE). The phosphorus protecting groups may then be removed using a thionucleophile reagent such as a 1 M solution of disodium 2-carbamoyl-2-cyanoethylene-1, 1-dithiolate in DMF (1 mL) for 30 minutes. The 2'-protecting group may then be removed from the oligonucleotide by reacting the support bound oligonucleotide with an aqueous acidic buffer at pH 3.8, followed by washing with acetonitrile. The exocyclic amine protection and solid support linker may then be deprotected and cleaved, respectively, with neat 1,2-diaminoethane for 2 hours at room temperature. The 1,2-diaminoethane may be washed from the solid support with anhydrous acetonitrile. The RNA oligonucleotide may then be recovered from the solid support using an aqueous buffer or chromatographic mobile phase.

In certain embodiments a mixed sequence 20mer RNA molecule may be synthesized on a solid support using 2'-O-(1,1-dioxo-1$\lambda^6$-thiomorpholine-4-carbothioate) protected nucleoside phosphoramidites. Cyanoethyl protecting groups used on the phosphate internucleotide bond may be removed using neat diethylamine. The diethylamine solution may be washed from the solid support with acetonitrile and the support dried with a stream of argon. The 2'-O-(1,1-dioxo-1$\lambda^6$-thiomorpholine-4-carbothioate) protecting group, exocyclic amine protection and solid support linker may then be deprotected or cleaved with neat 1, 2-diaminoethane for 2 hours at room temperature. The 1, 2-diaminoethane may be washed from the solid support with anhydrous acetonitrile. The RNA oligonucleotide may then be recovered from the solid support using an aqueous buffer or chromatographic mobile phase.

In some embodiments a mixed sequence 20mer RNA molecule may be synthesized on a solid support using 2'-O-(1,1-dioxo-1$\lambda^6$-thiomorpholine-4-carbothioate) protected nucleoside phosphoramidites. The 2'-O-(1,1-dioxo-1$\lambda^6$-thiomorpholine-4-carbothioate) protecting groups, exocyclic amine protections, cyanoethyl protecting groups on the internucleotide phosphates, and the solid support linker may then be deprotected or cleaved with neat 1,2-diaminoethane for 2 hours at room temperature. The 1,2-diaminoethane may be washed from the solid support with anhydrous acetonitrile. The RNA oligonucleotide may then be recovered from the solid support using an aqueous buffer or chromatographic mobile phase.

In some embodiments of the deprotection methods described herein, the polynucleotide may be attached to a solid support via a linker that is orthogonal to one or more of the protecting groups used, i.e. it remains intact during treatment with one or more of a phosphate, nucleobase or 2'-deprotection reagents. The orthogonal linker may be optionally cleaved either before or after one of the deprotection steps of a method described herein. Exemplary orthogonal linkers include but are not limited to, a photocleavable linker or a fluoride cleavable linker.

1,2-Diaminoethane Reagents and Compositions Useful for the Deprotection of a Polynucleotide Comprising One or More Ribonucleotide Residues.

Described herein is the evaluation of a variety of diamines for their effectiveness at cleaving a 2'-thionocarbamate protecting group, for example a 2'-O-(1,1-dioxo-1$\lambda^6$-thiomorpholine-4-carbothioate). The graph of FIG. 1 summarizes the effectiveness of a set of diamines reagents, including: (1) neat 1,2-diaminoethane, (2) neat 1,2-diaminopropane, (3) neat 1,3-diaminopropane, (4) neat 1,4-diaminobutane, (5) neat 1,3-diamino-2,2-dimethylpropane, (6) neat 1,2-diamino-2-methylpropane, (7) neat N,N-diisopropyl-1,2-diaminoethane, (8) neat N,N-diethyl-1,2-diaminoethane, (9) 1M 1,3-diamino-2-propanol in 1,3-diaminopropane, (10) 1M 1,3-diamino-2-propanol in 4,7,10-trioxa-1,13-diaminotridecane, (11) neat 4,7,10-trioxa-1,13-diaminotridecane, and (12) neat N-(2-aminoethyl)-1,2-diaminoethane (DET); at cleaving the 2'-thionocarbamate group: 2'-O-(1,1-dioxo-1$\lambda^6$-thiomorpholine-4-carbothioate) (TC), of a 16-mer oligonucleotide U(2'-TC)T$_{15}$~succ~CPG after treatment for 2 hours at room temperature.

Figure 4A:
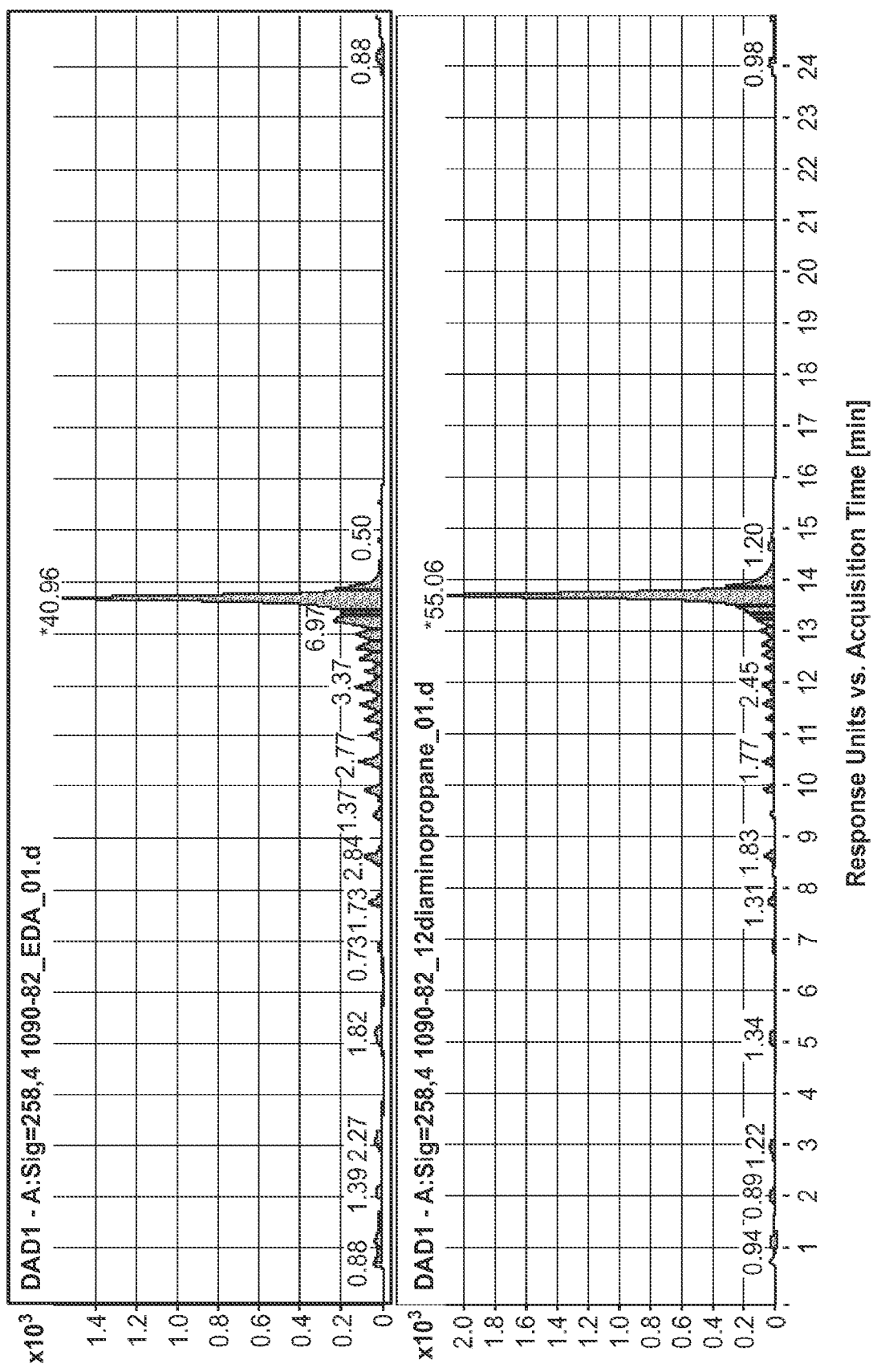
FIGS. 4A and 4B are HPLC chromatograms showing deprotection of a 21mer oligonucleotide with five diamine compositions (1, 2, 3, 4 and 12) after a 24 hours deprotection reaction.
Figure 4B:
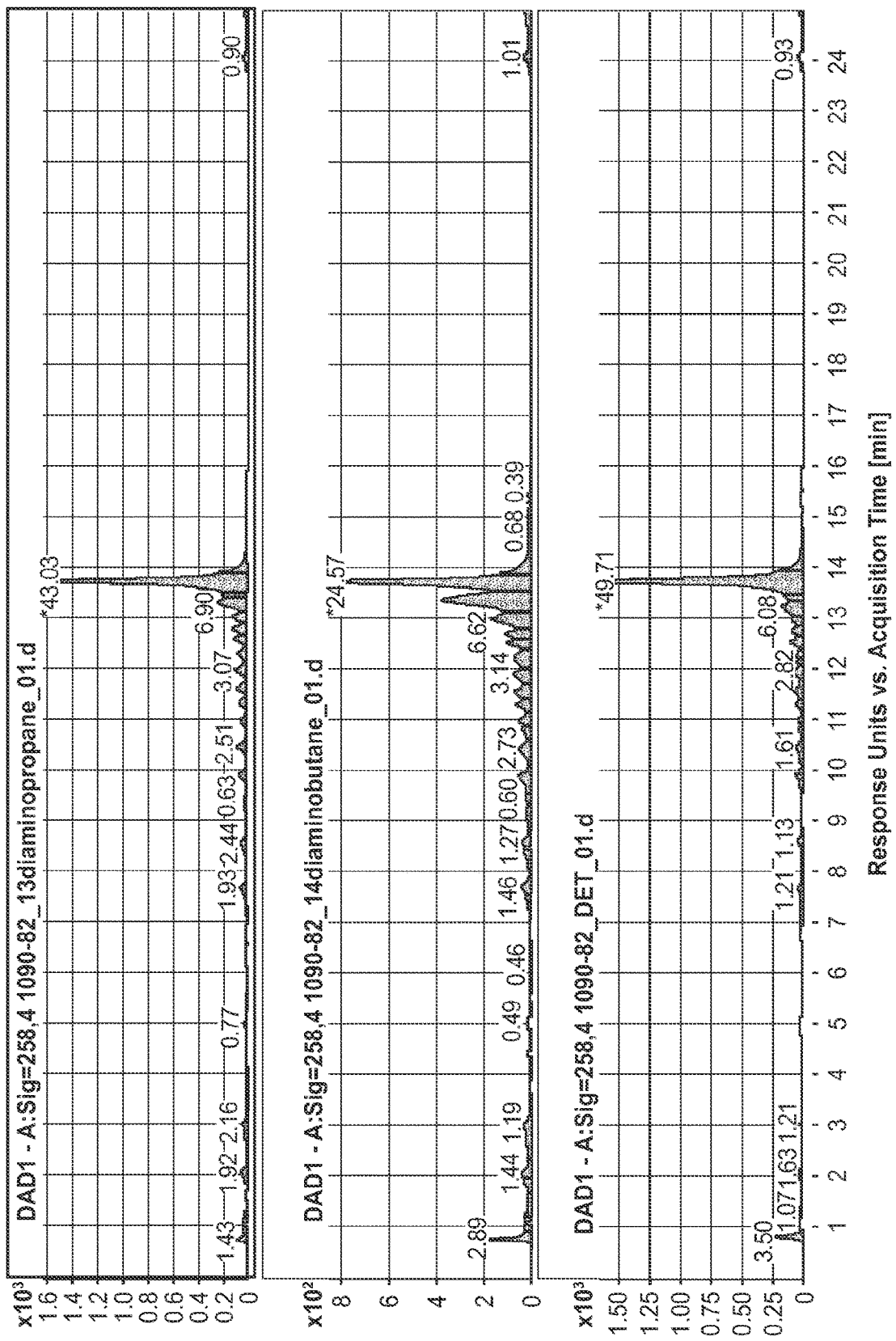

In the evaluation shown in FIG. 1 it is worth noting that 1,3-diamino-2 propanol is a solid compound unlike the other diamines which are liquid, so was dissolved in two different solvents 1,3-diaminopropane or 4,7, 10-trioxa-1,13-tridecanediamine for purposes of evaluation and to control for the effect of the solvent. In FIG. 1 diamine reagents are evaluated by the % deprotection that occurs. Further evaluation is described herein of the diamine reagents 1, 2, 3, 4 and 12, described above, and their ability to deprotect a synthetic RNA that contains 2'-thionocarbamate protecting groups and a mixed oligoribonucleotide sequence; by looking at the ratio of deprotection (including deprotection of nucleobase protecting groups) versus degradation of the oligonucleotide at the internucleotide linkages. The deprotection of a 21-mer oligoribonucleotide (5'-GUG UCA GUA CAG AUG AGG CCT-3'-CPG) (SEQ ID NO. 1) with 2'-O-(1,1-dioxo-1$\lambda^6$-thiomorpholine-4-carbothioate) protecting groups and standard exocyclic amine protecting groups (N²-acetyl-cytidine, N⁶-benzoyl-adenosine, N²-isobutyryl-guanosine); where the deprotection reactions were carried out at room temperature, was analyzed by HPLC and mass spectrometry (data not shown) after 2 and 24 hours. A 1,2-diaminoethane (1) deprotection resulted in complete deprotection of the 21 mer oligoribonucleotide in 2 hours, while the other diamines (3, 12, 2 and 4) showed incomplete deprotection products with higher retention times by analysis of HPLC chromatograms (data not shown). After 24 hours of deprotection time, the reactions were analyzed again by HPLC/MS (FIGS. 4A and 4B). All deprotection HPLC profiles corresponding to the different amines used (1, 2, 3, 4, and 12; respectively 1,2-diaminoethane, 1,2-diaminopropane, 1,3-diaminoproane, 1,4 diaminobutane and N-(2-aminoethyl)-1,2-diaminoethane) show complete deprotection of the above 21-mer oligoribonucleotide.

Based upon the percentage of full length deprotected RNA product obtained from these 24 hour reactions, the amines were evaluated for their effectiveness. At 24 hours, the 1,2-diaminoethane deprotection showed an increase in RNA degradation products as compared to the 2 hours deprotection reaction. The other diamines evaluated show complete deprotection of the 21-mer oligoribinucleotide, however with different degree of RNA degradation. A deprotection reaction may be optimized by adjusting the experimental conditions (time, temperature, etc.) such that the full RNA deprotection is achieved while the RNA degradation is minimized.

The evaluations of amine compositions described above indicate that 1,2-diaminoethane is a suitable diamine for use in the deprotection of a oligoribonucleotide. Less suitable are 1,2-diaminopropane, N-(2-aminoethyl)-1,2-diaminoethane), 1,3-diaminoproane, and 1,4-diaminobutane.

Solvent Effect on 1,2-Diaminoethane Deprotection

Figure 2:
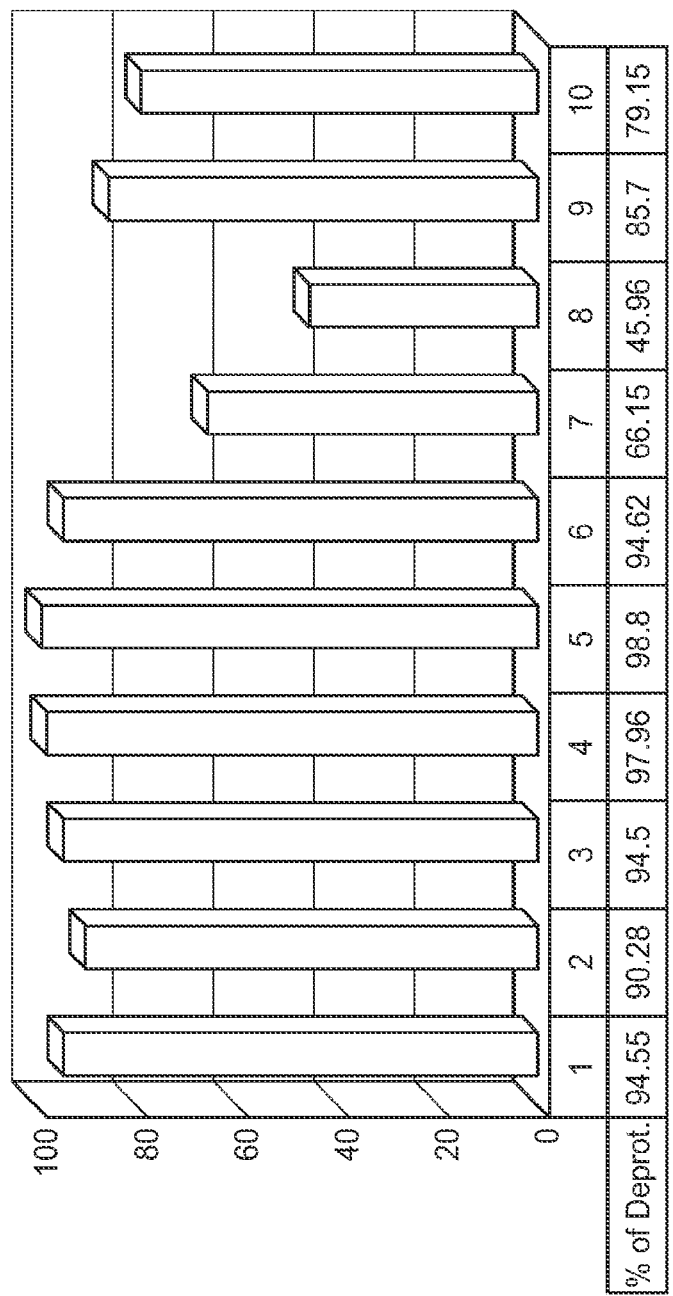
FIG. 2 is a graph showing deprotection of U(2'TC) T$_{15}$~succ~CPG reacted with 50% v/v 1,2-diaminoethane in solvents 1-10 for 2 hours at room temperature, where U(2'TC) indicates a U residue protected with a 2'-thionocarbamate protecting group.
Figure 3:
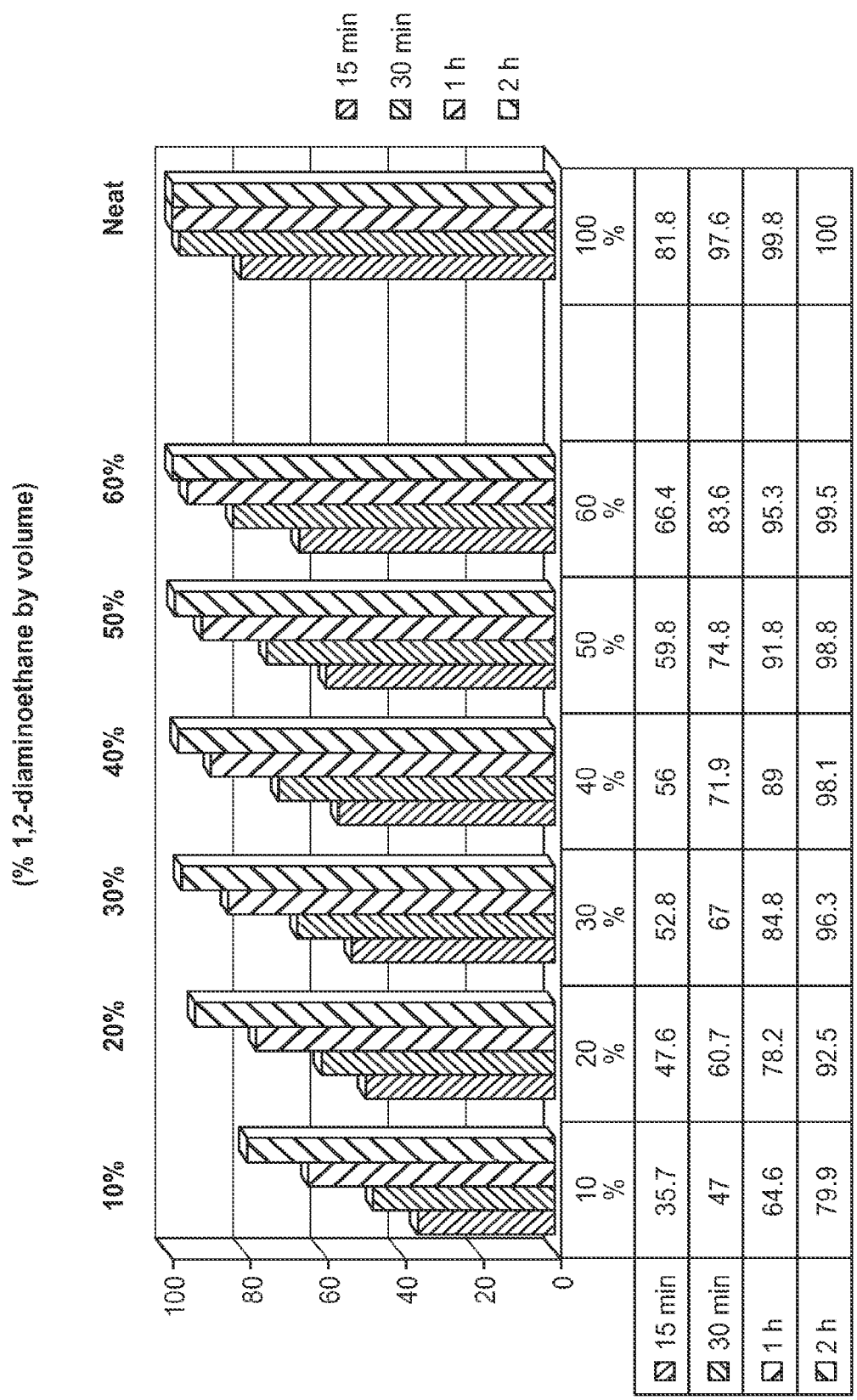
FIG. 3 is a graph showing deprotection of U(2'TC) T$_{15}$~succ~CPG with solutions of 1,2-diaminoethane (10% to 100%) in toluene, where U(2'TC) indicates a U residue protected with a 2'-thionocarbamate protecting group.

In some embodiments, a composition comprising a diamine, for example 1,2-diaminoethane in a solvent can be used effectively to deprotect RNA or a polynucleotide comprising a ribonucleotide residue. Described below is the evaluation of the effect of a solvent on the rate of deprotection using various concentrations of 1,2-diaminoethane in different solvent solutions. Synthesis of a 16-mer oligonucleotide with only a uridine at the 5'-end, 5'-U(2'TC)T$_{15}$-3' was performed using 5'-O-(4,4'-dimethoxytrityl)-3'-O-methyl-N,N-diisopropyl-phosphoramidite-2'-O-(1,1-dioxo-1λ⁶-thiomorpholine-4-carbothioate)-uridine on a dT CPG solid support. This olionucleotide was deprotected for 2 hours using solvents 1-10 (FIG. 2) {MeCN (1), 1,4-dioxane (2), THF (3), 2-methyl-THF (4), toluene (5), DCM (6), iPrOH (7), hexafluoroisopropanol (HFiP, 8), morpholine (9), MeOH (10)} of 1,2-diaminoethane (50% v/v approximately 7.5 M) and the deprotection products were analyzed by HPLC (data not shown). Treatment of the oligonucleotide above with neat 1,2-diaminoethane showed essentially complete deprotection of the 2'-O-(1,1-dioxo-1λ⁶-thiomorpholine-4-carbothioate) protecting group after 1 hour (FIG. 3). In particular embodiments the solvent may be an organic solvent such as toluene, 2-methyl-THF, THF, acetonitrile (MeCN), 1,4-dioxane, or mixtures thereof.

In solvents 1-6 and 9, the dilution of 1,2-diaminoethane did not affect drastically the rate of the 2'-protecting group removal, with at least 80% of uridine deprotection achieved, indicating that the 2'-O-(1,1-dioxo-1λ⁶-thiomorpholine-4-carbothioate) protecting group was removed at a similar rate as when a neat solution of 1,2 diaminoethane was used. The protic solvents such as, isopropanol (7), HFiP (8) and MeOH (10) affected the rate of the uridine 2'-deprotection more significantly. In the case of MeOH, the solution dissolved the deprotected oligonucleotide UT15 and thus only ~40% of the deprotected product remained adsorbed onto the column and was recovered.

While it was found that a fifty percent dilution of 1,2-diaminoethane in various solvents (for example 1, 2, 3, 4, 5, 6, 9) was effective at deprotecting U(2'TC)T$_{15}$, it is noteworthy to point out that all the toluene solutions of 1,2-diaminoethane with a concentration ranging from 10% to 100% were very effective at cleaving 2'-O-(1,1-dioxo-1λ⁶-thiomorpholine-4-carbothioate) in 2 hours, as shown in the FIG. 3.

Furthermore, a similar evaluation of the deprotection of 5'-U(2'TC)$_{15}$T-3' shows that toluene solutions of 1,2-diaminoethane are comparably effective to neat 1,2-diaminoethane under similar conditions (2 hours at room temperature, data not shown). In certain embodiments, a deprotection time of up to 24 hrs, with solvents other than toluene do achieve the complete deprotection of a mixed oligonucleotide sequence, for example, by the use of 50% 1,2-diaminoethane in isopropanol (v/v) to deprotect a 21-mer oligoribonucleotide (5'-GUG UCA GUA CAG AUG AGG CCT-3'-CPG) (SEQ ID NO. 1) synthesized with 2'-O-(1,1-dioxo-1λ⁶-thiomorpholine-4-carbothioate) protecting groups and standard exocyclic amine protecting groups (N²-acetyl-cytidine, N⁶-benzoyl-adenosine, N²-isobutyryl-guanosine) (data not shown).

Nucleic Acid Products

Some embodiments described herein include the nucleic acid products of the methods. A nucleic acid product, for example, an RNA, of the methods described herein may be of various sizes, ranging in certain embodiments from 2 to 500 or more monomeric units in length, e.g., such as 2 to 200 or more, 2 to 100 or more or 2 to 50 or more monomeric units in length. In certain embodiments, the size of a product nucleic acids ranges from 2 to 25 monomeric units in length, e.g., 15 to 25 monomeric units in length, such as 17 to 23 monomeric units in length, including 19, 20, 21, or 22 monomeric units in length.

In certain embodiments described herein, a nucleic acid product has the structure of Formula (IX), where B$^P$ is a protected or unprotected nitrogen-containing base, as defined herein; X is O or S; and Q is a thionocarbamate protecting group, e.g., as described herein, and R$^{12}$ is selected from the group consisting of hydrogen, hydrocarbyls, substituted hydrocarbyls, aryls, and substituted aryls; and m is an integer greater than 1.

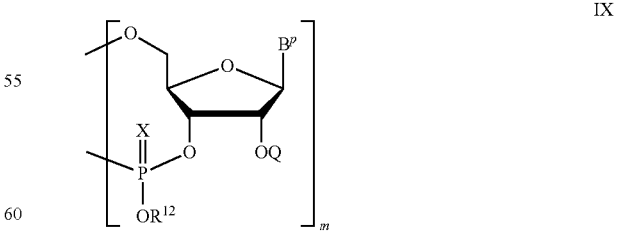

IX

In some embodiments, a nucleic acid described herein comprises the structure of Formula (X) below, wherein the variables B$^P$, X and R$^{12}$ are defined as for the structure of Formula (IX) above, and Y is defined as for the structure of Formula (Ia) above.

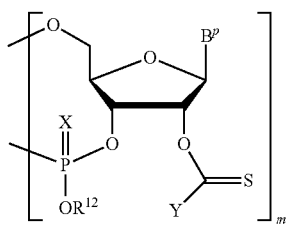

Particular embodiments described herein include a nucleic acid comprising the structure of Formula (XI), where $B^P$ is a protected or unprotected nitrogen-containing base, as defined herein; X is O or S; and $R^{100}$, $R^{101}$, $R^{102}$, $R^{103}$, $R^{104}$ are each independently selected from hydrogen, a hydrocarbyl, a substituted hydrocarbyl, an aryl and a substituted aryl; and $R^{12}$ is selected from the group consisting of hydrogen, a hydrocarbyl, a substituted hydrocarbyl, an aryl and a substituted aryl; and m is an integer greater than 1.

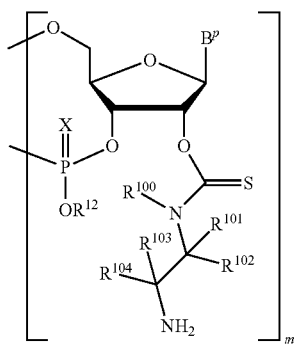

Particular embodiments described herein include a nucleic acids that comprises the structure of Formula (XII), wherein $B^P$ is a protected or unprotected nitrogen-containing base, as defined herein; X is O or S; and $R^{100}$, $R^{101}$, $R^{101}$, $R^{103}$, $R^{104}$, $R^{105}$, $R^{106}$, and $R^{107}$ are each independently selected from hydrogen, a hydrocarbyl, a substituted hydrocarbyl, an aryl and a substituted aryl; and $R^{12}$ is selected from the group consisting of hydrogen, a hydrocarbyl, a substituted hydrocarbyl, an aryl and a substituted aryl; and m is an integer greater than 1.

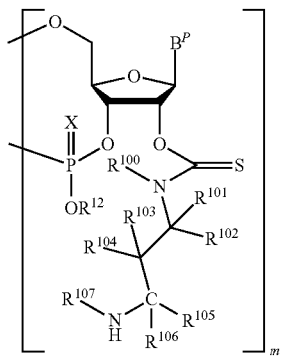

Certain embodiments described herein include a nucleic acid that comprises one of the following structures:

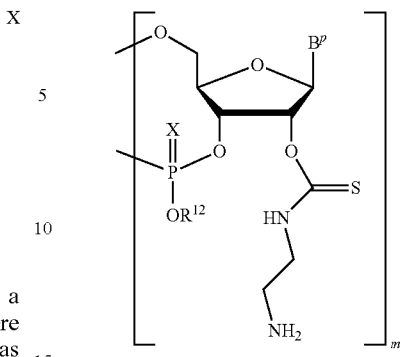

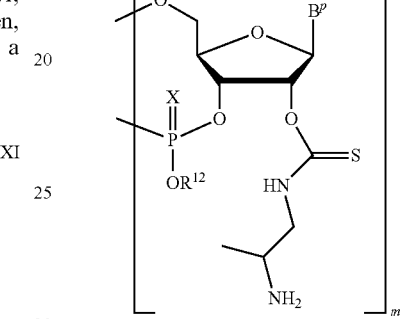

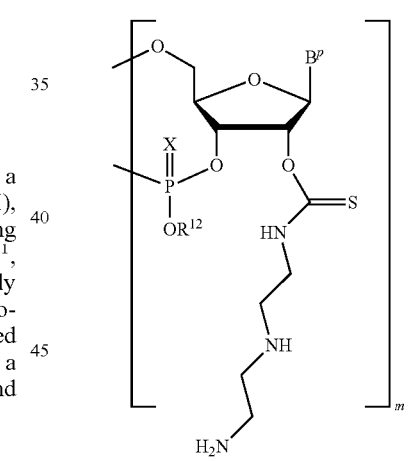

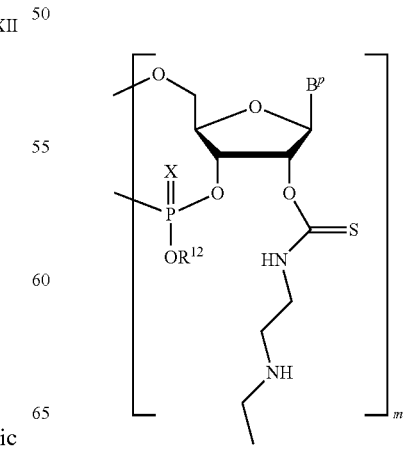

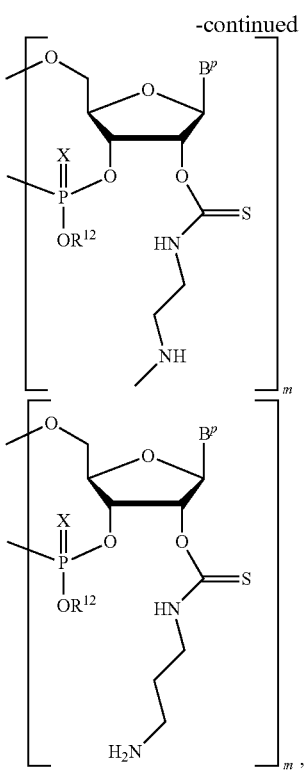

wherein $R^{12}$, X and $B^P$ are described as above.

Transcarbamoylation

In some embodiments when treated with a composition comprising an amine reagent, a nucleic acid of the structure (IX) or (X) as described herein, can undergo reaction leading to a deprotected product, or reaction leading to a transcarbamoylated product. An exemplary reaction with an amine $RNH_2$ is shown in Scheme 100, wherein the RNA 2'-hydroxyl protecting group is a 2'-O-(1,1-dioxo-1$\lambda^6$-thiomorpholine-4-carbothioate).

Scheme 100

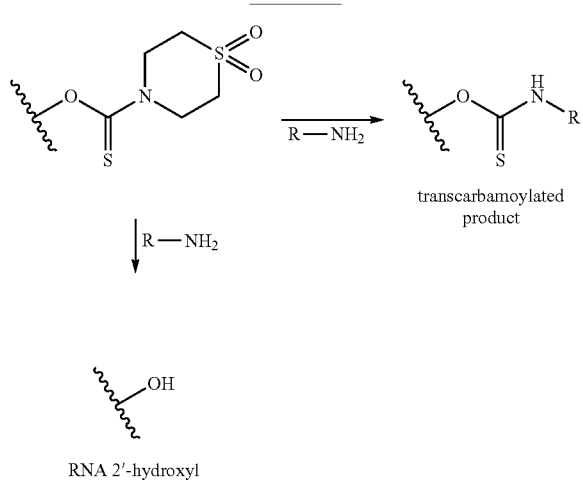

RNA 2'-hydroxyl

The reaction described above is presumed to proceed through the tetrahedral intermediate below, although other mechanisms and intermediates have not been ruled out.

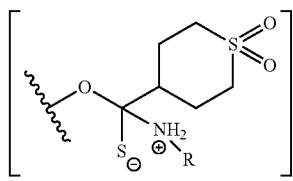

In some embodiments, the reaction with an amine described above leads to relatively stable carbamate products. Primary aliphatic amines, such as butylamine, may result in a slow reaction leading to a mixture of products. In a exemplary reaction the product observed after 2 hours of treating the synthesized 2'-O-(1,1-dioxo-1$\lambda^6$-thiomorpholine-4-carbothioate) protected $U_{15}T$ on solid support with butylamine, was the fully protected thionocarbamate-protected RNA, with some amounts of the products that correspond to having one and two protecting groups removed. A small amount of oligonucleotide containing the transcarbomoylated residue below was also observed.

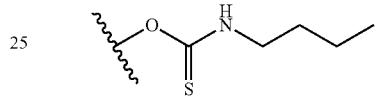

In some embodiments a transcarbamoylated product can undergo further reaction, and give the desired deprotected product. For example, when 2'-O-(1,1-dioxo-1$\lambda^6$-thiomorpholine-4-carbothioate) protected U15T on solid support is treated with gas phase ammonia for 16 hr, the final product obtained is the fully deprotected $U_{15}T$, with a small amount of oligonucleotide comprising transcarbamoylated primary thionocarbamate residues, e.g., as shown below, and an amount of product comprising backbone fragmentation products.

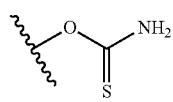

Extracted mass spectrum ion chromatograms of the reaction mixture showed the relative amounts of $U_{15}T$, mono-transcarbomoylated product, and cyclic phosphate products arising from backbone fragmentation. Plotting all of the $U_{15}T$ primary thionocarbamates on the same acquisition time scale, compared to the amount of $U_{15}T$ product formed (counts), showed that the only major transcarbamoylated product is the $U_{15}T$ comprising a single primary thionocarbamate. If a gas phase ammonia reaction is stopped after 3.5 hours, the product distribution is much different. Extracted ion chromatograms of the same ions plotted on the same acquisition time scale show that relative to the amount of $U_{15}T$ formed, the reaction contains a large percentage of a homologous series of primary thionocarbamates. The initial primary thionocarbamate product formed after 3.5 hours is capable of further reaction, and after 16 hours is transformed into the desired product. A possible mechanism for this reaction is an addition-elimination reaction involving the reversible addition of another ammonia molecule eventually followed by the irreversible loss of the alkoxide, leading to the desired product, although other mechanisms have not been ruled out.

Reaction with 1,2-diaminoethane Compounds

Compounds containing a 1,2-diamino functionality, e.g., such as 1,2-diaminoethane react with 2'-O-(1,1-dioxo-1λ$^6$-thiomorpholine-4-carbothioate) protected RNA to give the desired fully deprotected product (below)

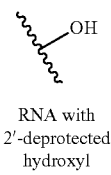
RNA with 2'-deprotected hydroxyl

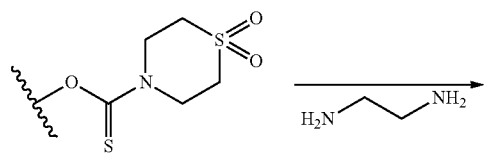

This reaction can proceed through multiple pathways. Some of these are illustrated in Scheme 101. The reaction pathway can go directly to the desired alcohol, or the 1,2-diaminoethane thionocarbamate (1,2-diaminoethane-N-carbothioate) can be formed. The diaminoethane thionocarbamate can go on to deprotected product via loss of a cyclic thiourea, or diaminoethane or another nucleophile can add to the diaminoethane thionocarbamate to give reversible formation of an intermediate which can go on to the deprotected product.

Scheme 101

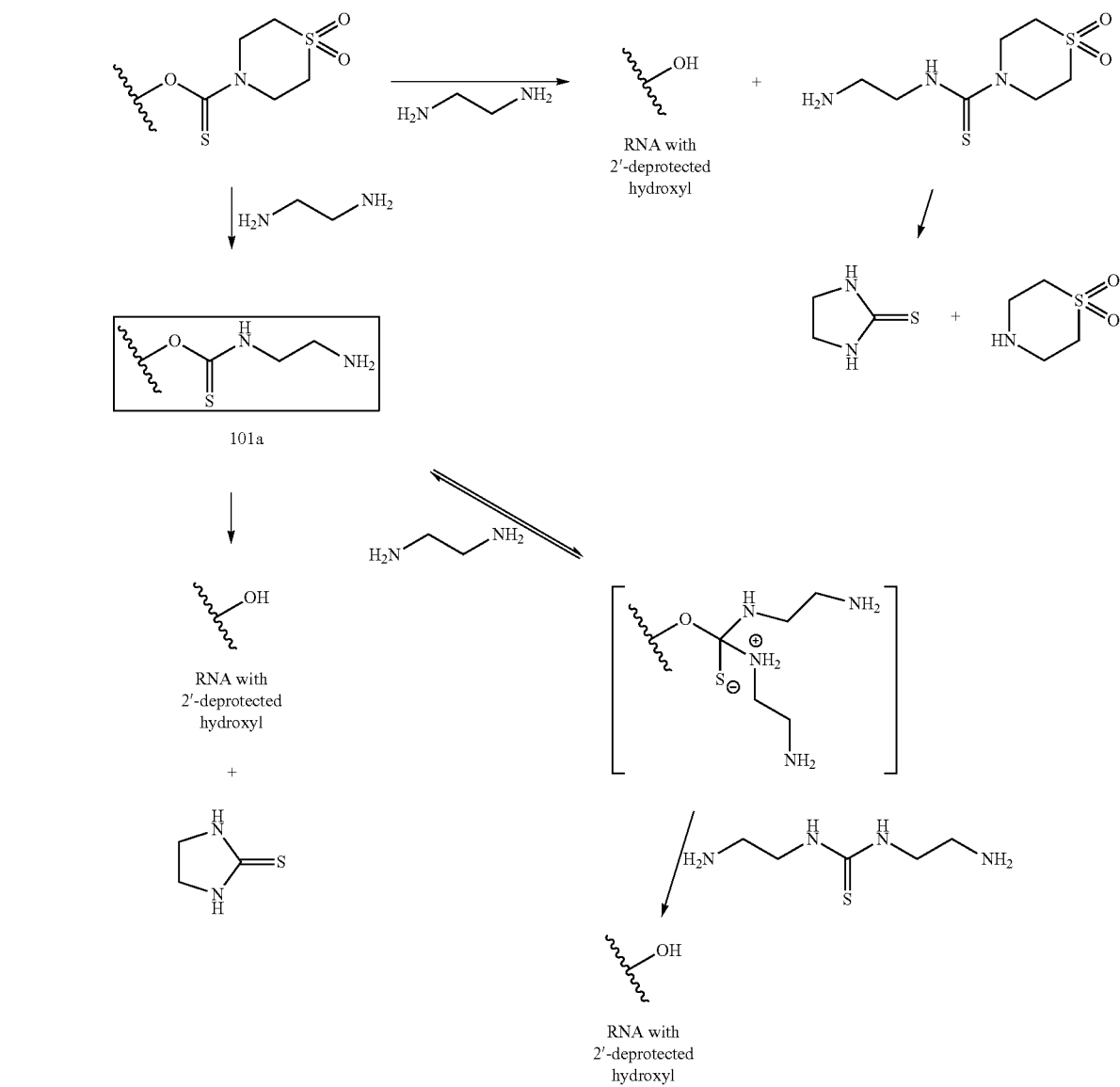

In certain embodiments, it is observed that during the treatment of 1,2-diaminoethane or substituted versions thereof to a 2'-O-(1,1-dioxo-1$\lambda^6$-thiomorpholine-4-carbothioate) protected RNA, a portion of the deprotected product (shown in Scheme 101 for the 1,2-diaminoethane example) derives from the diaminoethane thionocarbamate 101a. This compound, as characterized by HPLC-MS, converts quickly to the desired deprotected 2'-hydroxyl upon further treatment with 1,2-diaminoethane. Conversion of the diaminoethane thionocarbamate 101a also occurs, generally at a slower rate, when the compound is dissolved in water. In particular embodiments, a 2'-O-(1,1-dioxo-1$\lambda^6$-thiomorpholine-4-carbothioate) protected $U_{15}T$ on resin is treated with 1,2-diaminoethane for two hours, the deprotection reaction proceeds to completion; wherein analysis of the reaction mixture using HPLC-high resolution mass spectrometry indicates that less than 0.5% of the transcarbamoylated diaminoethane thionocarbamate product is present.

In certain cases when a dried down aliquot of a 45 minute 1,2-diaminoethane reaction is redissolved in 1,2-diaminoethane, the transcarbamoylated product 101a is rapidly converted to desired 2'-hydroxyl deprotected $U_{15}T$ product. (Exemplary details: an aliquot of the reaction mixture was dried down to a residue under vacuum, was redissolved in 1,2-diaminoethane, allowed to stand for 90 minutes, dried down to a residue under vacuum again, then dissolved in water and subjected to HPLC-MS analysis. A control aliquot was dried down to a residue under vacuum and subjected to the same conditions as the first aliquot, except that no 1,2-diaminoethane was added. After treatment with 1,2-diaminoethane for 90 minutes, there was no amount of transcarbamoylated products 101a observed in the HPLC analysis. The control aliquot, which was not treated with 1,2-diaminoethane, showed about 14% of the mono-thionocarbamate product, and about 1.4% of the bis-thionocarbamate product).

In certain cases the 1,2-diaminoethane transcarbamoylated products 101a are converted to the desired 2'-hydroxyl deprotected $U_{15}T$ when treated with 1,2-diaminopropane, as similarly described above. HPLC-MS analysis show that about 2% of 1,2-diaminoethane thionocarbamate was present, compared to a level of about 14% in the control. No transcarbamoylated product due to exchange with 1,2-diaminopropane is observed.

Substituted 1,2-diamines for the Deprotection of 2'-O-(1,1-dioxo-1$\lambda^6$-thiomorpholine-4-carbothioate) Protected RNA In certain embodiments a 2'-O-(1,1-dioxo-1$\lambda^6$-thiomorpholine-4-carbothioate) protected $U_{15}T$ on resin is treated with a composition comprising 1,2-diaminopropane for 6 hours. HPLC-MS analysis of the reaction mixture indicates a mono-1,2-diaminopropanethionocarbamate transcarbamoylated product is present at about 10% yield. Extended treatment of a 2'-O-(1,1-dioxo-1$\lambda^6$-thiomorpholine-4-carbothioate) protected $U_{15}T$ on resin for 2.5 days results in conversion of the reaction mixture to the completely deprotected $U_{15}T$ by HPLC-MS analysis, although such an extended reaction time may result in an increase in backbone fragmentation products.

In particular embodiments a 2'-O-(1,1-dioxo-1$\lambda^6$-thiomorpholine-4-carbothioate) protected U15T on resin is treated with N-(2-aminoethyl)-1,2-ethanediamine; wherein HPLC-MS analysis is performed on the reaction mixture after 6 hours, indicating about 12% yield of the N-(2-aminoethyl)-1,2-ethanediamine thionocarbamate. After standing in water for 3 days at room temperature in the HPLC injection vial, reanalyzing the sample by HPLC-MS, indicates that the N-(2-aminoethyl)-1,2-ethanediamine thionocarbamate initially formed is converted to the desired deprotected $U_{15}T$. Ion exchange chromatography of the material before and after standing for 3 days in water also indicates the conversion of the N-(2-aminoethyl)-1,2-ethanediamine thionocarbamate into the desired $U_{15}T$ product.

In particular embodiments when 2'-O-(1,1-dioxo-1$\lambda^6$-thiomorpholine-4-carbothioate) protected $U_{15}T$ on resin is treated with N-(2-aminoethyl)-1,2-ethanediamine for 2 hours, the deprotection reaction does not go to completion, and later eluting peaks are visible in the HPLC-MS analysis. However, a significant amount of completely deprotected $U_{15}T$ and a small amount of N-(2-aminoethyl)-1,2-ethanediamine thionocarbamate is formed as well. After standing in water for 3 days at room temperature in the HPLC injection vial, reanalyzing the sample by HPLC-MS indicates that the N-(2-aminoethyl)-1,2-ethanediamine thionocarbamate transcarbamoylated product initially formed is converted to the desired deprotected $U_{15}T$. The profile of the rest of the total ion chromatogram does not change, indicating that the remaining 2'-O-(1,1-dioxo-1$\lambda^6$-thiomorpholine-4-carbothioate) protected 2'-hydroxyl comprising residues are stable to these conditions.

Applications

The product nucleic acids produced in accordance with methods described herein find use in a variety of applications, including research, diagnostic and therapeutic applications. For example, the product nucleic acids find use in research applications, e.g., as probes, primers, etc. With respect to diagnostic applications, the product nucleic acids may also find use as probes, primers, or other agents employed in diagnostic protocols. With respect to therapeutic applications, the product nucleic acids find use as any DNA, RNA or other nucleic acid therapeutic, such as antisense nucleic acids, in gene therapy applications, interfering RNA (i.e., iRNA or RNAi) applications, etc.

Depending on the application for which the nucleic acids are synthesized, the nucleic acids may or may not be modified in some manner following their synthesis. As such, in certain embodiments the product nucleic acids are not further modified following synthesis. In yet other embodiments, the nucleic acids are modified in some manner following their synthesis.

A variety of different modifications may be made to the product nucleic acids as desired. For example, where the product nucleic acids are interfering ribonucleic acids (iRNA), a variety of post-synthesis modifications may be desirable. The iRNA agent can be further modified so as to be attached to a ligand that is selected to improve stability, distribution or cellular uptake of the agent, e.g., cholesterol. The following post-synthesis modifications are described for convenience primarily in terms of iRNA embodiments. However, such modifications are readily adapted to DNA embodiments and the following description encompasses such embodiments as well.

The following modifications may be made before or after cleavage of the nucleic acid from the support, as desired.

Unmodified RNA refers to a molecule in which the components of the nucleic acid, namely sugars, bases, and phosphate moieties, are the same or essentially the same as that which occur in nature, e.g., as occur naturally in the human body. The art has referred to rare or unusual, but naturally occurring, RNAs as modified RNAs, see, e.g., Limbach et al., (1994) Nucleic Acids Res. 22: 2183-2196. Such rare or unusual RNAs, often termed modified RNAs (apparently because these are typically the result of a post-transcriptional modification) are within the term unmodified RNA, as used herein. Modified RNA as used herein refers to a molecule in which one or more of the components of the nucleic acid, namely sugars, bases, and phosphate moieties, are different from that which occurs in nature, e.g., different from that which occurs in the human body. While they are referred to as modified "RNAs," they will of course, because of the modification, include molecules which are not RNAs. Nucleoside surrogates are molecules in which the ribophosphate backbone is replaced with a non-ribophosphate construct that allows the bases to the presented in the correct spatial relationship such that hybridization is substantially similar to what is seen with a ribophosphate backbone, e.g., non-charged mimics of the ribophosphate backbone. Examples of each of the above are discussed herein.

Modifications described herein can be incorporated into any double-stranded RNA and RNA-like molecule described herein, e.g., an iRNA agent. It may be desirable to modify one or both of the antisense and sense strands of an iRNA agent. As nucleic acids are polymers of subunits or monomers, many of the modifications described below occur at a position which is repeated within a nucleic acid, e.g., a modification of a base, or a phosphate moiety, or the non-linking 0 of a phosphate moiety. In some cases the modification will occur at all of the subject positions in the nucleic acid but in many, and in fact in most, cases it will not. By way of example, a modification may only occur at a 3' or 5' terminal position, may only occur in a terminal region, e.g. at a position on a terminal nucleotide or in the last 2, 3, 4, 5, or 10 nucleotides of a strand. A modification may occur in a double strand region, a single strand region, or in both. For example, a phosphorothioate modification at a non-linking O position may only occur at one or both termini, may only occur in a terminal regions, e.g., at a position on a terminal nucleotide or in the last 2, 3, 4, 5, or 10 nucleotides of a strand, or may occur in double strand and single strand regions, particularly at termini. Similarly, a modification may occur on the sense strand, antisense strand, or both. In some cases, the sense and antisense strand will have the same modifications or the same class of modifications, but in other cases the sense and antisense strand will have different modifications, e.g., in some cases it may be desirable to modify only one strand, e.g. the sense strand.

Two prime objectives for the introduction of modifications into iRNA agents is their stabilization towards degradation in biological environments and the improvement of pharmacological properties, e.g., pharmacodynamic properties, which are further discussed below. Other suitable modifications to a sugar, base, or backbone of an iRNA agent are described in PCT Application No. PCT/US2004/01193, filed Jan. 16, 2004. An iRNA agent can include a non-naturally occurring base, such as the bases described in PCT Application No. PCT/US2004/011822, filed Apr. 16, 2004. An iRNA agent can include a non-naturally occurring sugar, such as a non-carbohydrate cyclic carrier molecule. Exemplary features of non-naturally occurring sugars for use in iRNA agents are described in PCT Application No. PCT/US2004/11829 filed Apr. 16, 2003.

An iRNA agent can include an internucleotide linkage (e.g., the chiral phosphorothioate linkage) useful for increasing nuclease resistance. In addition, or in the alternative, an iRNA agent can include a ribose mimic for increased nuclease resistance. Exemplary internucleotide linkages and ribose mimics for increased nuclease resistance are described in PCT Application No. PCT/US2004/07070 filed on Mar. 8, 2004.

An iRNA agent can include ligand-conjugated monomer subunits and monomers for oligonucleotide synthesis. Exemplary monomers are described in U.S. application Ser. No. 10/916,185, filed on Aug. 10, 2004. An iRNA agent can have a structure, such as is described in PCT Application No. PCT/US2004/07070 filed on Mar. 8, 2004. An iRNA agent can be complexed with an amphipathic moiety. Exemplary amphipathic moieties for use with iRNA agents are described in PCT Application No. PCT/US2004/07070 filed on Mar. 8, 2004.

In another embodiment, the iRNA agent can be complexed to a delivery agent that features a modular complex. The complex can include a carrier agent linked to one or more of (such as two or more, including all three of): (a) a condensing agent (e.g., an agent capable of attracting, e.g., binding, a nucleic acid, e.g., through ionic or electrostatic interactions); (b) a fusogenic agent (e.g., an agent capable of fusing and/or being transported through a cell membrane); and (c) a targeting group, e.g., a cell or tissue targeting agent, e.g., a lectin, glycoprotein, lipid or protein, e.g., an antibody, that binds to a specified cell type. iRNA agents complexed to a delivery agent are described in PCT Application No. PCT/US2004/07070 filed on Mar. 8, 2004.

An iRNA agent can have non-canonical pairings, such as between the sense and antisense sequences of the iRNA duplex. Exemplary features of non-canonical iRNA agents are described in PCT Application No. PCT/US2004/07070 filed on Mar. 8, 2004.

An iRNA agent can have enhanced resistance to nucleases. For increased nuclease resistance and/or binding affinity to the target, an iRNA agent, e.g., the sense and/or antisense strands of the iRNA agent, can include, for example, 2'-modified ribose units and/or phosphorothioate linkages. For example, the 2' hydroxyl group (OH) can be modified or replaced with a number of different "oxy" or "deoxy" substituents.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEGs), $O(CH_2CH_2O)_nCH_2CH_2OR$; "locked" nucleic acids (LNA) in which the 2' hydroxyl is connected, e.g., by a methylene bridge, to the 4' carbon of the same ribose sugar; O-AMINE and aminoalkoxy, $O(CH_2)_n$AMINE, (e.g., AMINE=$NH_2$; alkylamino, dialkylamino, heterocyclyl amino, arylamino, diaryl amino, heteroaryl amino, or diheteroaryl amino, ethylene diamine, polyamino). It is noteworthy that oligonucleotides containing only the methoxyethyl group (MOE), ($OCH_2CH_2OCH_3$, a PEG derivative), exhibit nuclease stabilities comparable to those modified with the robust phosphorothioate modification.

"Deoxy" modifications include hydrogen (i.e. deoxyribose sugars, which are of particular relevance to the overhang portions of partially ds RNA); halo (e.g., fluoro); amino (e.g. $NH_2$; alkylamino, dialkylamino, heterocyclyl, arylamino, diaryl amino, heteroaryl amino, diheteroaryl amino, or amino acid); —$NH(CH_2CH_2NH)_nCH_2CH_2$-AMINE (AMINE=$NH_2$; alkylamino, dialkylamino, heterocyclyl amino, arylamino, diaryl amino, heteroaryl amino, or diheteroaryl amino), —NHC(O)R(R=alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino functionality. Examples of other modifications include the use of nucleosides other than D-ribonucleosides that are found in natural RNA. Examples of other nucleosides include L-ribonucleoside, D and L-arabino-nucleoside, D and L xylo-nucleoside, D and L lyxo-nucleoside, D and L gluco-nucleoside, D and L-pyrano-nucleosides, acyclic nucleosides, and alpha nucleosides wherein the heterocycle is in an alpha anomeric configuration as opposed to the typical beta anomeric configuration and the like.

One way to increase resistance is to identify cleavage sites and modify such sites to inhibit cleavage, as described in U.S. Application No. 60/559,917, filed on May 4, 2004. For example, the dinucleotides 5'-UA-3',5'-UG-3',5'-CA-3',5'-UU-3', or 5'-CC-3' can serve as cleavage sites. Enhanced nuclease resistance can therefore be achieved by modifying the 5' nucleotide, resulting, for example, in at least one 5'-uridine-adenine-3' (5'-UA-3') dinucleotide wherein the uridine is a 2'-modified nucleotide; at least one 5'-uridine-guanine-3' (5'-UG-3') dinucleotide, wherein the 5'-uridine is a 2'-modified nucleotide; at least one 5'-cytidine-adenine-3' (5'-CA-3') dinucleotide, wherein the 5'-cytidine is a 2'-modified nucleotide; at least one 5'-uridine-uridine-3' (5'-UU-3') dinucleotide, wherein the 5'-uridine is a 2'-modified nucleotide; or at least one 5'-cytidine-cytidine-3' (5'-CC-3') dinucleotide, wherein the 5'-cytidine is a 2'-modified nucleotide. The iRNA agent can include at least 2, at least 3, at least 4 or at least 5 of such dinucleotides. In certain embodiments, all the pyrimidines of an iRNA agent carry a 2'-modification, and the iRNA agent therefore has enhanced resistance to endonucleases.

To maximize nuclease resistance, the 2' modifications can be used in combination with one or more phosphate linker modifications (e.g., phosphorothioate). The so-called "chimeric" oligonucleotides are those that contain two or more different modifications.

The inclusion of furanose sugars in the oligonucleotide backbone can also decrease endonucleolytic cleavage. An iRNA agent can be further modified by including a 3' cationic group, or by inverting the nucleoside at the 3'-terminus with a 3'-3' linkage. In another alternative, the 3'-terminus can be blocked with an aminoalkyl group, e.g., a 3'C5-aminoalkyl dT. Other 3' conjugates can inhibit 3'-5' exonucleolytic cleavage. While not being bound by theory, a 3' conjugate, such as naproxen or ibuprofen, may inhibit exonucleolytic cleavage by sterically blocking the exonuclease from binding to the 3'-end of the oligonucleotide. Even small alkyl chains, aryl groups, or heterocyclic conjugates or modified sugars (D-ribose, deoxyribose, glucose etc.) can block 3'-5'-exonucleases.

Similarly, 5' conjugates can inhibit 5'-3' exonucleolytic cleavage. While not being bound by theory, a 5' conjugate, such as naproxen or ibuprofen, may inhibit exonucleolytic cleavage by sterically blocking the exonuclease from binding to the 5'-end of the oligonucleotide. Even small alkyl chains, aryl groups, or heterocyclic conjugates or modified sugars (D-ribose, deoxyribose, glucose etc.) can block 3'-5'-exonucleases.

An iRNA agent can have increased resistance to nucleases when a duplexed iRNA agent includes a single-stranded nucleotide overhang on at least one end. In some embodiments, the nucleotide overhang includes 1 to 4 unpaired nucleotides, in other embodiments 2 to 3 unpaired nucleotides. In one embodiment, the unpaired nucleotide of the single-stranded overhang that is directly adjacent to the terminal nucleotide pair contains a purine base, and the terminal nucleotide pair is a G-C pair, or at least two of the last four complementary nucleotide pairs are G-C pairs. In further embodiments, the nucleotide overhang may have 1 or 2 unpaired nucleotides, and in an exemplary embodiment the nucleotide overhang is 5'-GC-3'. In certain embodiments, the nucleotide overhang is on the 3'-end of the antisense strand. In one embodiment, the iRNA agent includes the motif 5'-CGC-3' on the 3'-end of the antisense strand, such that a 2-nucleotide overhang 5'-GC-3' is formed.

Thus, an iRNA agent can include modifications so as to inhibit degradation, e.g., by nucleases, e.g., endonucleases or exonucleases, found in the body of a subject. These monomers are referred to herein as NRMs, or Nuclease Resistance promoting Monomers, the corresponding modifications as NRM modifications. In many cases these modifications will modulate other properties of the iRNA agent as well, e.g., the ability to interact with a protein, e.g., a transport protein, e.g., serum albumin, or a member of the RISC, or the ability of the first and second sequences to form a duplex with one another or to form a duplex with another sequence, e.g., a target molecule.

One or more different NRM modifications can be introduced into an iRNA agent or into a sequence of an iRNA agent. An NRM modification can be used more than once in a sequence or in an iRNA agent.

NRM modifications include some which can be placed only at the terminus and others which can go at any position. Some NRM modifications that can inhibit hybridization may be used only in terminal regions, and not at the cleavage site or in the cleavage region of a sequence which targets a subject sequence or gene, particularly on the antisense strand. They can be used anywhere in a sense strand, provided that sufficient hybridization between the two strands of the ds iRNA agent is maintained. In some embodiments it is desirable to put the NRM at the cleavage site or in the cleavage region of a sense strand, as it can minimize off-target silencing.

In certain embodiments, the NRM modifications will be distributed differently depending on whether they are comprised on a sense or antisense strand. If on an antisense strand, modifications which interfere with or inhibit endonuclease cleavage should not be inserted in the region which is subject to RISC mediated cleavage, e.g., the cleavage site or the cleavage region (As described in Elbashir et al., 2001, Genes and Dev. 15: 188, hereby incorporated by reference). Cleavage of the target occurs about in the middle of a 20 or 21 nucleotide antisense strand, or about 10 or 11 nucleotides upstream of the first nucleotide on the target mRNA which is complementary to the antisense strand. As used herein cleavage site refers to the nucleotides on either side of the site of cleavage, on the target mRNA or on the iRNA agent strand which hybridizes to it. Cleavage region means the nucleotides within 1, 2, or 3 nucleotides of the cleavage site, in either direction.

Such modifications can be introduced into the terminal regions, e.g., at the terminal position or with 2, 3, 4, or 5 positions of the terminus, of a sequence which targets or a sequence which does not target a sequence in the subject.

The properties of an iRNA agent, including its pharmacological properties, can be influenced and tailored, for example, by the introduction of ligands, e.g. tethered ligands. A wide variety of entities, e.g., ligands, can be tethered to an iRNA agent, e.g., to the carrier of a ligand-conjugated monomer subunit. Examples are described below in the context of a ligand-conjugated monomer subunit but that is only preferred, entities can be coupled at other points to an iRNA agent.

Of interest are ligands, which are coupled, e.g., covalently, either directly or indirectly via an intervening tether, to the carrier. In certain embodiments, the ligand is attached to the carrier via an intervening tether. The ligand or tethered ligand may be present on the ligand-conjugated monomer when the ligand-conjugated monomer is incorporated into the growing strand. In some embodiments, the ligand may be incorporated into a "precursor" ligand-conjugated monomer subunit after a "precursor" ligand-conjugated monomer subunit has been incorporated into the growing strand. For example, a monomer having, e.g., an amino-terminated tether, e.g., TAP-(CH$_2$)$_n$NH$_2$ may be incorporated into a growing sense or antisense strand. In a subsequent operation, i.e., after incorporation of the precursor monomer subunit into the strand, a ligand having an electrophilic group, e.g., a pentafluorophenyl ester or aldehyde group, can subsequently be attached to the precursor ligand-conjugated monomer by coupling the electrophilic group of the ligand with the terminal nucleophilic group of the precursor ligand-conjugated monomer subunit tether.

In certain embodiments, a ligand alters the distribution, targeting or lifetime of an iRNA agent into which it is incorporated. In preferred embodiments a ligand provides an enhanced affinity for a selected target, e.g., molecule, cell or cell type, compartment, e.g., a cellular or organ compartment, tissue, organ or region of the body, as, e.g., compared to a species absent such a ligand.

Ligands of interest can improve transport, hybridization, and specificity properties and may also improve nuclease resistance of the resultant natural or modified oligoribonucleotide, or a polymeric molecule comprising any combination of monomers described herein and/or natural or modified ribonucleotides. Ligands in general can include therapeutic modifiers, e.g., for enhancing uptake; diagnostic compounds or reporter groups e.g., for monitoring distribution; cross-linking agents; nuclease-resistance conferring moieties; and natural or unusual nucleobases. General examples include lipophilic moleculeses, lipids, lectins, steroids (e.g., uvaol, hecigenin, diosgenin), terpenes (e.g., triterpenes, e.g., sarsasapogenin, Friedelin, epifriedelanol derivatized lithocholic acid), vitamins, carbohydrates (e.g., a dextran, pullulan, chitin, chitosan, inulin, cyclodextrin or hyaluronic acid), proteins, protein binding agents, integrin targeting molecules, polycationics, peptides, polyamines, and peptide mimics.

The ligand may be a naturally occurring or recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly (2-ethylacrylic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic moieties, e.g., cationic lipid, cationic porphyrin, quaternary salt of a polyamine, or an alpha helical peptide.

Ligands can also include targeting groups, e.g., a cell or tissue targeting agent, e.g., a thyrotropin, melanotropin, surfactant protein A, Mucin carbohydrate, a glycosylated polyaminoacid, transferrin, bisphosphonate, polyglutamate, polyaspartate, or an RGD peptide or RGD peptide mimetic.

Ligands can be proteins, e.g., glycoproteins, lipoproteins, e.g. low density lipoprotein (LDL), or albumins, e.g. human serum albumin (HSA), or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as cofactors, multivalent lactose, multivalent galactose, N-acetyl-galactosamine, N-acetylglucosamine, multivalent mannose, or multivalent fucose. The ligand can be, for example, a lipopolysaccharide, an activator of p38 MAP kinase, or an activator of NF-κB.

The ligand can be a substance, e.g., a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

In one aspect, the ligand is a lipid or lipid-based molecule. Such a lipid or lipid-based molecule binds a serum protein, e.g., human serum albumin (HSA). An HSA binding ligand allows for distribution of the conjugate to a target tissue, e.g., liver tissue, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney. Also of interest are the lipid modifications described in WO/2005/023994; the disclosure of which is herein incorporated by reference.

In another aspect, the ligand is a moiety, e.g., a vitamin or nutrient, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include the B vitamins, e.g., folic acid, B12, riboflavin, biotin, pyridoxal or other vitamins or nutrients taken up by cancer cells.

In another aspect, the ligand is a cell-permeation agent, a helical cell-permeation agent. In some embodiments, the agent is amphipathic. An exemplary agent is a peptide such as tat or antennapedia. If the agent is a peptide, it can be modified, including a peptidylmimetic, invertomers, non-peptide or pseudo-peptide linkages, and use of D-amino acids. The helical agent may be an alpha-helical agent, which may have a lipophilic and a lipophobic phase.

In certain embodiments, iRNA agents are 5'-phosphorylated or include a phosphoryl analog at the 5'-terminus. 5'-phosphate modifications of the antisense strand include those which are compatible with RISC mediated gene silencing. Suitable modifications include: 5'-monophosphate ((HO)$_2$(O)P—O-5'); 5'-diphosphate ((HO)$_2$(O)P—O—P(HO)(O)—O-5'); 5'-triphosphate ((HO)$_2$(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure. Other suitable 5'-phosphate modifications will be known to the skilled person.

The sense strand can be modified in order to inactivate the sense strand and prevent formation of an active RISC, thereby potentially reducing off-target effects. This can be accomplished by a modification which prevents 5'-phosphorylation of the sense strand, e.g., by modification with a 5'-O-methyl ribonucleotide (see Nykanen et al., (2001) ATP requirements and small interfering RNA structure in the RNA interference pathway. Cell 107, 309-321.) Other modifications which prevent phosphorylation can also be used, e.g., simply substituting the 5'-OH by H rather than 0-Me. Alternatively, a large bulky group may be added to the 5'-phosphate turning it into a phosphodiester linkage.

Where desired, the nucleic acid, e.g., iRNA, DNA, etc, agents described herein can be formulated for administration to a subject, such as parenterally, e.g. via injection, orally, topically, to the eye, etc. As such, the nucleic acid can be combined with a pharmaceutically acceptable vehicle to provide a pharmaceutical composition. For ease of exposition, the formulations, compositions, and methods in this section are discussed largely with regard to unmodified iRNA agents. It should be understood, however, that these formulations, compositions, and methods can be practiced with other iRNA agents, e.g., modified iRNA agents, and such practice is within certain embodiments.

A formulated iRNA agent composition can assume a variety of states. In some examples, the composition is at least partially crystalline, uniformly crystalline, and/or anhydrous (e.g., less than 80, 50, 30, 20, or 10% water). In another example, the iRNA agent is in an aqueous phase, e.g., in a solution that includes water, this form being the preferred form for administration via inhalation. The aqueous phase or the crystalline compositions can be incorporated into a delivery vehicle, e.g., a liposome (particularly for the aqueous phase), or a particle (e.g., a microparticle as can be appropriate for a crystalline composition). Generally, the iRNA agent composition is formulated in a manner that is compatible with the intended method of administration.

An iRNA agent preparation can be formulated in combination with another agent, e.g., another therapeutic agent or an agent that stabilizes an iRNA agent, e.g., a protein that complexes with the iRNA agent to form an iRNP. Still other agents include chelators, e.g., EDTA (e.g., to remove divalent cations such as Mg24), salts, RNAse inhibitors (e.g., a broad specificity RNAse inhibitor such as RNAsin) and so forth.

In one embodiment, the iRNA agent preparation includes another iRNA agent, e.g., a second iRNA agent that can mediate RNAi with respect to a second gene. Still other preparations can include at least three, five, ten, twenty, fifty, or a hundred or more different iRNA species. In some embodiments, the agents are directed to the same gene but different target sequences.

The nucleic acids can be formulated into pharmaceutical compositions by combination with appropriate, pharmaceutically acceptable vehicles, i.e., carriers or diluents, and may be formulated into preparations in solid, semi solid, liquid or gaseous forms, such as tablets, capsules, powders, granules, ointments, solutions, suppositories, injections, inhalants and aerosols. As such, administration of the agents can be achieved in various ways, including oral, buccal, rectal, parenteral, intraperitoneal, intradermal, transdermal, intracheal, etc., administration.

In pharmaceutical dosage forms, the agents may be administered alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds described herein can be formulated into pressurized acceptable propellants such as dichlorodifluoromethane, propane, nitrogen and the like.

Furthermore, the agents can be made into suppositories by mixing with a variety of bases such as emulsifying bases or water soluble bases. The compounds described herein can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds described herein calculated in an amount sufficient to produce the desired effect in association with a pharmaceutically acceptable diluent, carrier or vehicle. The specifications for the novel unit dosage forms of particular embodiments depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Nucleic acids may also be introduced into tissues or host cells by other routes, including microinjection, or fusion of vesicles. Jet injection may also be used for intra-muscular administration, as described by Furth et al. (1992), Anal Biochem 205:365-368. The nucleic acids may be coated onto gold microparticles, and delivered intradermally by a particle bombardment device, or "gene gun" as described in the literature (see, for example, Tang et al. (1992), Nature 356:152 154), where gold microprojectiles are coated with the DNA, then bombarded into skin cells. Additional nucleic acid delivery protocols of interest include, but are not limited to: those described in U.S. patents of interest include U.S. Pat. Nos. 5,985,847 and 5,922,687 (the disclosures of which are herein incorporated by reference); WO/11092; Acsadi et al., New Biol. (1991) 3:71-81; Hickman et al., Hum. Gen. Ther. (1994) 5:1477-1483; and Wolff et al., Science (1990) 247: 1465-1468; etc. See e.g., the viral and non-viral mediated delivery protocols described above. Accordingly, of interest are pharmaceutical vehicles for use in such delivery methods.

The ribonucleic acids produced by embodiments of the methods find use in a variety of different applications, including but not limited to differential gene expression analysis, gene-silencing applications, nucleic acid library generation applications and therapeutic applications (e.g., in the production of antisense RNA, siRNA, etc.) Additional details regarding these types of utilities for RNA produced according to embodiments described herein are provided in pending U.S. patent application Ser. No. 10/961,991 titled "Array-Based Methods for Producing Ribonucleic Acids," filed on Oct. 8, 2004 and published as US-2006-0078889-A1 on Apr. 13, 2006; the disclosure of which is herein incorporated by reference.

Kits

Also of interest are kits for use in practicing certain embodiments described herein. In certain embodiments, kits include at least 2 different protected monomers, e.g., 2'-thionocarbamate protected nucleotide monomers described herein, where the kits may include the monomers that have the same nucleobase or monomers that include different nucleobases, e.g., A, G, C and U. The kits may further include additional reagents employed in methods described herein, e.g., buffers, oxidizing agents, capping agents, cleavage agents, etc.

Some other kit embodiments comprise components useful for the preparation of nucleotide monomer precursors. The kit may comprise TIPSCl$_2$, thiocarbonyldiimidazole, a dialkyl amine. The kit may further comprise reagents such as HF, pyridine, DCM, CH$_3$CN, Me-THF, a DMT-containing blocking agent (such as DMT chloride) and NCCH$_2$CH$_2$OP(NiPr$_2$)$_2$ or CH$_3$OP(NiPr$_2$)$_2$. The kits may include deprotecting reagents/compositions, e.g., as described above. The kit may also comprise unprotected ribonucleotide monomers, such as adenosine, guanosine, uridine, and/or cytidine ribonucleotides.

In certain embodiments, the kits will further include instructions for practicing the subject methods or means for obtaining the same (e.g., a website URL directing the user to a webpage which provides the instructions), where these instructions may be printed on a substrate, where substrate may be one or more of: a package insert, the packaging, reagent containers and the like. In the subject kits, the one or more components are present in the same or different containers, as may be convenient or desirable.

The following examples illustrate the synthesis of compounds described herein, and are not intended to limit the scope of the invention set forth in the claims appended hereto.

EXAMPLES

Synthesis of Various 2'-thionocarbamate Protected Monomers

Synthesis of 2'-O-(morpholine-4-carbothioate)-5'-O-(4,4'-dimethoxytrityl)-uridine-3'-O— (β-cyanoethyl)-N,N-diisopropyl-phosphoramidite (1)

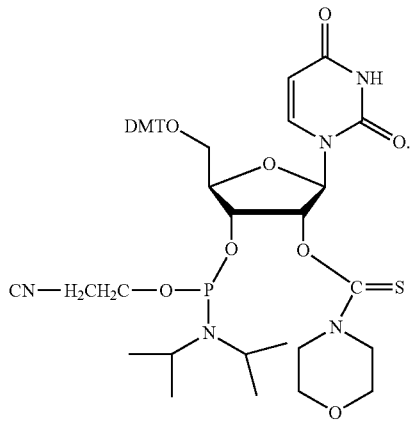

3'-5'-O-(Tetraisopropyldisiloxane-1,3-diyl)-uridine (ChemeGenes, 10 mmol, 4.86 grams) was dissolved in anhydrous acetonitrile (17 mL) in a 50 mL roundbottom flask fitted with a rubber septum. To the reaction of 1,1'-thiocarbonyldiimidazole (Aldrich, 10.5 mmol, 1.87 g) was added. The reaction was allowed to stir for 2 hours. After 2 hours, the reaction mixture was a slurry of crystals. The crystals were isolated by filtration through a medium sintered glass funnel. The product was washed with cold acetonitrile (10 mL) and dried under vacuum. TLC analysis confirmed that the product was a single species giving 5.97 grams of product (100%). ESI-Ion Trap mass spectroscopic analysis confirmed the product as the 5',3'-O-(tetraisopropyldisiloxane-1, 3-diyl)-2'-1-imidazole thionocarbamate with a mass of 597.12 (M+1).

The product was redissolved in 50 mL of anhydrous acetonitrile by heating using a heat gun. To the reaction was added morpholine (11 mmol, 958 mg). The reaction was stirred for 1 hour. TLC analysis demonstrated spot to spot conversion from the starting material to a higher running product. That product was isolated by evaporation of the acetonitrile. ESI-ION TRAP mass spectroscopy analysis confirmed the product as the 5',3'-O-(tetraisopropyldisiloxane-1,3-diyl)-2'-O-(morpholine-4-carbothioate) uridine with a mass of 616.21 (M+1). Hydrogen fluoride-pyridine complex (HF:Py 7:3, 3.1 mL) was carefully added to ice-cold solution of pyridine (4.85 mL) in acetonitrile/DCM (33/16.5 mL). The pyridine-HF reagent so formed (57.45 mL) was then transferred to the flask with 5', 3'-O-(tetraisopropyldisiloxane-1,3-diyl)-2'-O-(morpholine-4-carbothioate) protected uridine (10 mmol), and the mixture was stirred at room temperature for 2 hours. The reaction was quenched with water (100 mL). Crude product was extracted with EtOAc (5×200 mL), and dried with anhydrous Na$_2$SO$_4$. After filtration the organic layer was concentrated to a solid giving 3.5 grams (94% yield) of product shown as a single spot by TLC with a confirmed identity of the 2'-O-(morpholine-4-carbothioate)protected uridine by ESI-ION TRAP mass spectroscopy with a mass of 374.10 (M+1). 2'-O-(morpholine-4-carbothioate)protected uridine (9.4 mmol) was redissolved in anhydrous DCM/Me-THF (47/47 mL), NMM (N-methylmorpholine; 9.4 mmol) and 4,4'-dimethoxytrityl chloride (9.4 mmol) were added, and the mixture was stirred at room temperature until TLC (CHCl$_3$/MeOH 9:1) showed full disappearance of nucleoside substrate (0.5-1 hour). NMM (10.3 mmol) and N,N-diisopropylmethylphosphonamidic chloride (10.3 mmol) was added slowly to the reaction mixture. The reaction mixture was then stirred for 2 hours. The solvent was removed in vacuo, and the crude product was purified by column chromatography using hexanes with a gradient of acetone (10-30%) on silicagel, neutralized by 0.1% TEA in hexanes prior to introduction of phosphoramidite.

Synthesis of 2'-O—(N,O-dimethylhydroxylamino-carbothioate-5'-O-(4,4'-dimethoxytrityl)-uridine-3'-O-[methyl-(N,N-diisopropyl)]-phosphoramidite (2)

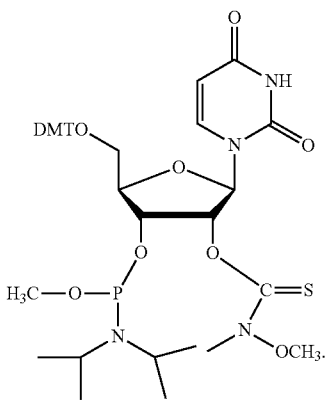

2

3'-5'-O-(Tetraisopropyldisiloxane-1,3-diyl)-uridine (ChemeGenes, 10 mmol, 4.86 grams) was dissolved in anhydrous acetonitrile (17 mL) in a 50 mL roundbottom flask fitted with a rubber septum. To the reaction 1,1'-thiocarbonyldiimidazole (Aldrich, 10.5 mmol, 1.87 g) was added. The reaction was allowed to stir for 2 hours. After 2 hours, the reaction mixture was a slurry of crystals. The crystals were isolated by filtration through a medium sintered glass funnel. The product was washed with cold acetonitrile (10 mL) and dried under vacuum. TLC analysis confirmed that the product was a single species giving 5.97 grams of product (100%). ESI-Ion Trap mass spectroscopic analysis confirmed the product as the 5', 3'-O-(tetraisopropyldisiloxane-1, 3-diyl)-2'-1-imidazole thionocarbamate with a mass of 597.12 (M+1). The product was suspended in 100 mL of anhydrous acetonitrile. To the reaction mixture was added 11 mmol of N,O-dimethylhydroxylamine hydrochloride (Aldrich), 15 mmol of diisopropylethylamine and 1.1 mmol of 4-(dimethyl)aminopyridine. The reaction was heated using a heat gun to dissolve the reagents, producing a clear solution. The mixture was stoppered and stirred for 12 hours. After 12 hours, the reaction mixture was evaporated to an oil, and dried under vacuum. TLC analysis confirmed that the product was a single species giving 5.9 grams of product. ESI-ION TRAP mass spectroscopy analysis confirmed the product as the 5',3'-O-(tetraisopropyldisiloxane-1, 3-diyl)-2'-O-dimethylhydroxylaminocarbothioate with a mass of M+1, 590.24 m/e. Hydrogen fluoride-pyridine complex (HF:Py 7:3, 7 mL) was carefully added to ice-cold solution of pyridine (8 mL) in acetonitrile (46.5 mL). The pyridine-HF reagent so formed (32 mL) was then transferred to the flask with 5',3'-O-(tetraisopropyldisiloxane-1,3-diyl)-2'-O—(N,O-dimethylhydroxylamino-carbothioate) protected uridine (10 mmol), and the mixture was stirred at room temperature for 2 hours. The reaction was quenched with water (300 mL). Crude product was extracted with EtOAc (5 times), and dried with anhydrous Na$_2$SO$_4$. After filtration organic layer was concentrated to a viscous oil giving 3.1 grams (86% yield) of product shown as a single spot by TLC with a confirmed identity of the 2'-O—(N,O-dimethylhydroxylamino-carbothioate) protected uridine by ESI-ION TRAP mass spectroscopy with a mass of M+1, 348.09 m/e. 2'-O—(N,O-dimethylhydroxylamino-carbothioate) protected uridine (8.7 mmol) was redissolved in anhydrous DCM/Me-THF (45/45 mL), NMM (8.7 mmol) and 4,4'-dimethoxytrityl chloride (8.7 mmol) were added, and the mixture was stirred at room temperature until TLC (CHCl$_3$/MeOH 9:1) showed full disappearance of nucleoside substrate (1-2 hours). NMM (9.0 mmol) and 1-methylimidazole (4.5 mmol) were added in one portion and N,N-diisopropylmethylphosphonamidic chloride (22 mmol) was added slowly to the reaction mixture over 10-15 minutes. The reaction mixture was then stirred for another 2 hours. The solvent was removed in vacuo, and the crude product was purified by column chromatography using hexanes with a gradient of EtOAc (0-50%).

Synthesis of 2'-O-(phenylaminecarbothioate)-5'-O-(4,4'-dimethoxytrityl)-uridine-3'-O-(β-cyanoethyl)-N,N-diisopropyl-phosphoramidite (3)

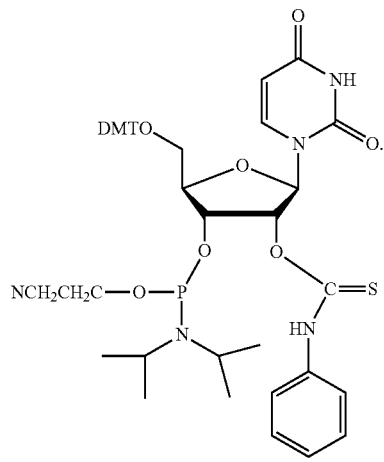

3

3'-5'-tetraisopropyldisiloxane-1,3-diyl-uridine (ChemeGenes, 10 mmol, 4.8 g) was dissolved in 100 mL of anhydrous acetonitrile in a 500 mL roundbottom flask fitted with a rubber septum. To the reaction 1.9 grams of 1,1'-thiocarbonyldiimidazole (Aldrich) was added with 0.2 grams of 4-(dimethyl)aminopyridine. The reaction was heated using a heat gun and stirred until the reagents had dissolved and the solution was clear. The reaction was allowed to stir overnight (12 hours). After 12 hours, the reaction mixture was a slurry of crystals. The crystals were isolated by filtration through a medium sintered glass funnel. The product was washed with cold acetonitrile and dried under vacuum. TLC analysis confirmed that the product was a single species giving 5.97 g of product (100%) ESI-ION TRAP mass spectroscopy analysis confirmed the product as the 5'-3'-O-(tetraisopropyldisiloxane-1,3-diyl)-2'-1-imidazole thionocarbamate with a mass of M+1, 598.12 m/e. The product was suspended in 100 mL of anhydrous acetonitrile. To the reaction mixture was added 11 mmol of aniline (Aldrich), and 11 mmol of 4-(dimethyl)aminopyridine. The reaction was fitted with a reflux condenser and heated to reflux for 12 hours. After 12 hours, the reaction mixture was evaporated to an oil, and dried under vacuum. TLC analysis confirmed that the product was present in about 80% yield along with 2.2-anhydrouridine. The product was purified on silica gel using a methanol/methylene chloride gradient (0-5%). ESI-ION TRAP mass spectroscopy analysis confirmed the product as the 5',3'-O-(tetraisopropyldisiloxane-1,3-diyl)-2'-O-(phenylaminecarbothioate)uridine with a mass of M+1, 622.33 m/e. Hydrogen fluoride-pyridine complex (HF:Py 7:3, 7 mL) was carefully added to ice-cold solution of pyridine (6.5 mL) in acetonitrile (37.2 mL). The pyridine-HF reagent so formed (25 mL) was then transferred to the flask with 5',3'-O-(tetraisopropyldisiloxane-1,3-diyl)-2'-O-phenylamine-carbothioate protected uridine (8 mmol), and the mixture was stirred at room temperature for 2 hours. The reaction was quenched with 5% solution of calcium chloride in water (300 mL). Crude product was extracted with EtOAc (3-5 times), and dried with anhydrous $Na_2SO_4$. After filtration organic layer was concentrated to a viscous oil giving 2.4 grams (81% yield) of product shown as a single spot by TLC with a confirmed identity of the 2'-O-phenylamine-carbothioate protected uridine by ESI-ION TRAP mass spectroscopy with a mass of M+1, 380.18 m/e. 2'-O-phenylamine-carbothioate protected uridine (6.4 mmol) was redissolved in anhydrous THF (65 mL), NMM (45 mmol) and 4,4'-dimethoxytrityl chloride (8.0 mmol) were added, and the mixture was stirred at room temperature until TLC ($CHCl_3$/MeOH 9:1) showed full disappearance of nucleoside substrate (16-24 hours). NMM (6.4 mmol) and 1-methylimidazole (3.2 mmol) were added in one portion and N,N-diisopropylmethylphosphonamidic chloride (16 mmol) was added slowly to the reaction mixture over 10-15 minutes. The reaction mixture was then stirred for another 2 hours. The solvent was removed in vacuo, and the crude product was purified by column chromatography using hexanes with a gradient of EtOAc (0-50%).

2'-O-(1,1-dioxo-1$\lambda^6$-thiomorpholine-4-carbothioate)-5'-O-(4,4'-dimethoxytrityl)-$N^2$-isobutyryl-guanosine-3'-O-(β-cyanoethyl)-N,N-diisopropyl-phosphoramidite (4)

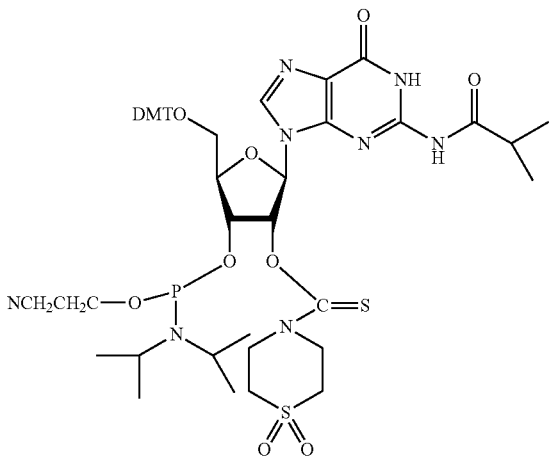

4

2'-O-(1,1-dioxo-1$\lambda^6$-thiomorpholine-4-carbothioate)-$N^2$-isobutyryl-guanosine 3',5'-O-(Tetraisopropyldisiloxane-1,3-diyl)-$N^2$-isobutyryl-guanosine (5.95 g, 10 mmol) was dissolved in ACN (50 mL, 0.2 M) and 1,1'-thiocarbonyldiimidazole (1.88 g, 10.5 mmol) was added and stirred for 2 h at ambient temperature. Thiomorpholine-1,1-dioxide (1.48 g, 11 mmol) was added to the reaction mixture solution and stirred for 2 h. Crystals were collected by filtration, and dried at RT for 2 h in high vacuum (7.7 g, 10 mmol).

3',5'-O-(Tetraisopropyldisiloxane-1,3-diyl)-2'-O-(1,1-dioxo-1$\lambda^6$-thiomorpholine-4-carbothioate)-$N^2$-isobutyryl-guanosine (7.7 g, 10 mmol) was suspended in Me-THF (50 mL) and hydrogen fluoride pyridine (HFxPy) (1.56 mL, 60 mmol HF) and pyridine (3.4 mL, 42 mmol) were added. Reaction mixture might be cooled if warmed up. The reaction solution was stirred for 2.5 h at ambient temperature then extracted with water (50 mL) and the aqueous layer was extracted with Me-THF (2×100 mL). Organics were combined, dried with $Na_2SO_4$ (50 g), filtered and evaporated. Yield 5.17 g (97%). $R_f$ (TLC 10% MeOH/DCM): 0.3. All solvents and reagents must be anhydrous in the following up to the final extraction step.

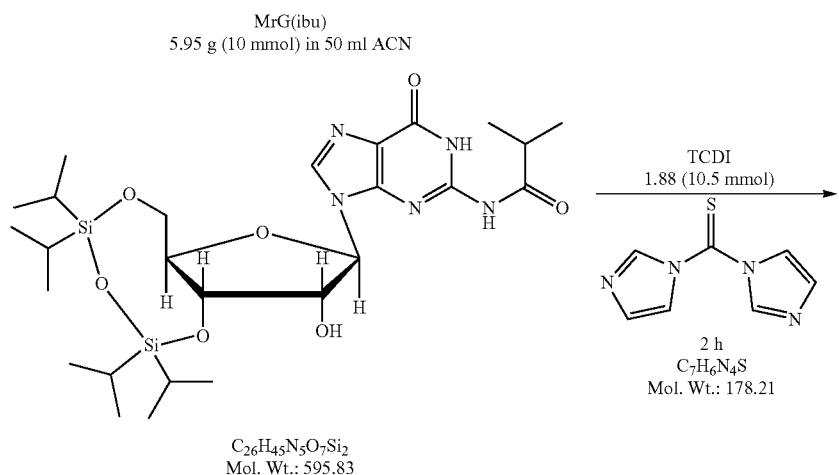
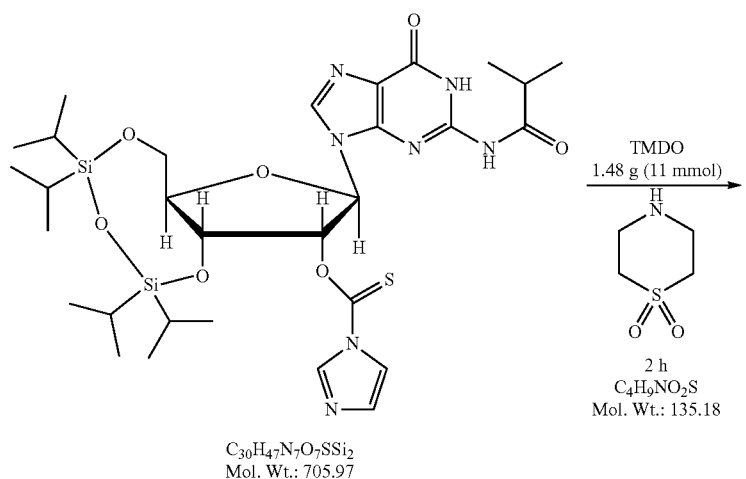
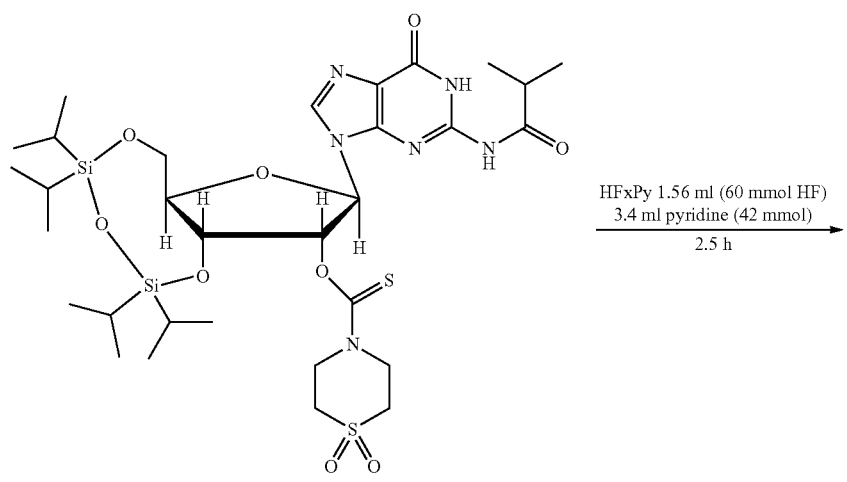

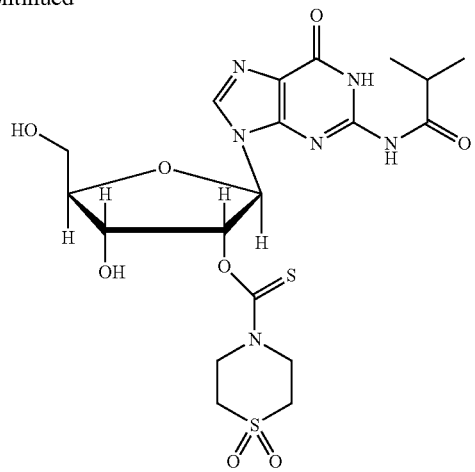

C₁₉H₂₆N₆O₈S₂
Mol. Wt.: 530.58

2'-O-(1,1-dioxo-1λ⁶-thiomorpholine-4-carbothioate)-N²-isobutyryl-guanosine

3',5'-O-(Tetraisopropyldisiloxane-1,3-diyl)-N²-isobutyryl-guanosine (5.95 g, 10 mmol) was dissolved in ACN (50 mL, 0.2 M) and 1,1'-thiocarbonyldiimidazole (1.88 g, 10.5 mmol) was added and stirred for 2 h at ambient temperature. Thiomorpholine-1,1-dioxide (1.48 g, 11 mmol) was added to the reaction mixture solution and stirred for 2 h. Crystals were collected by filtration, and dried at RT for 2 h in high vacuum (7.7 g, 10 mmol).

3',5'-O-(Tetraisopropyldisiloxane-1,3-diyl)-2'-O-(1,1-dioxo-1λ⁶-thiomorpholine-4-carbothioate)-N²-isobutyryl-guanosine (7.7 g, 10 mmol) was suspended in Me-THF (50 mL) and hydrogen fluoride pyridine (HFxPy) (1.56 mL, 60 mmol HF) and pyridine (3.4 mL, 42 mmol) were added. Reaction mixture might be cooled if warmed up. The reaction solution was stirred for 2.5 h at ambient temperature then extracted with water (50 mL) and the aqueous layer was extracted with Me-THF (2×100 mL). Organics were combined, dried with Na₂SO₄ (50 g), filtered and evaporated. Yield 5.17 g (97%). R_f (TLC 10% MeOH/DCM): 0.3. All solvents and reagents must be anhydrous in the following up to the final extraction step.

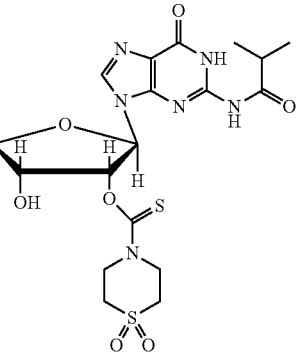

rG(ibu)TC
5.17 g (7.94 mmol) in 195 ml DCM/M—THF

C₁₉H₂₆N₆O₈S₂
Mol. Wt.: 530.58

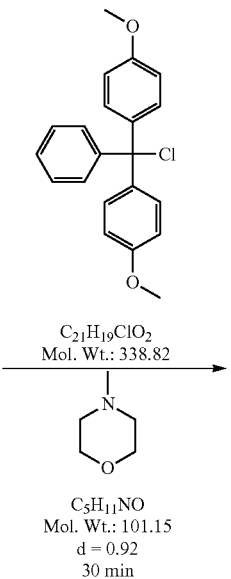

DMTCl 2.48 g (7.3 mmol)
NMM 803 ul (7.3 mmol)

C₂₁H₁₉ClO₂
Mol. Wt.: 338.82

C₅H₁₁NO
Mol. Wt.: 101.15
d = 0.92
30 min

-continued
DMTrG(ibu)TC
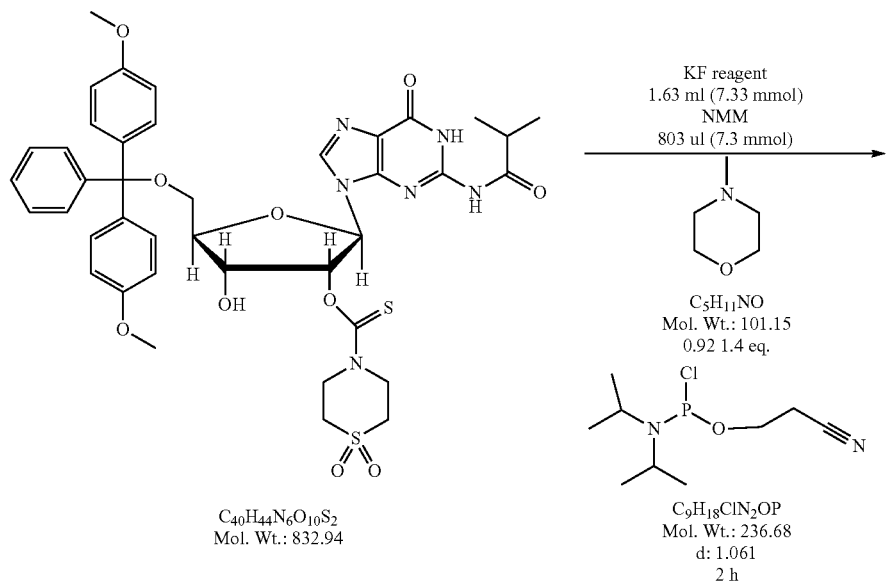
C₄₀H₄₄N₆O₁₀S₂
Mol. Wt.: 832.94
C₅H₁₁NO
Mol. Wt.: 101.15
0.92 1.4 eq.
C₉H₁₈ClN₂OP
Mol. Wt.: 236.68
d: 1.061
2 h
DMTrG(ibu)TC CEPA
6.0 g (60%)
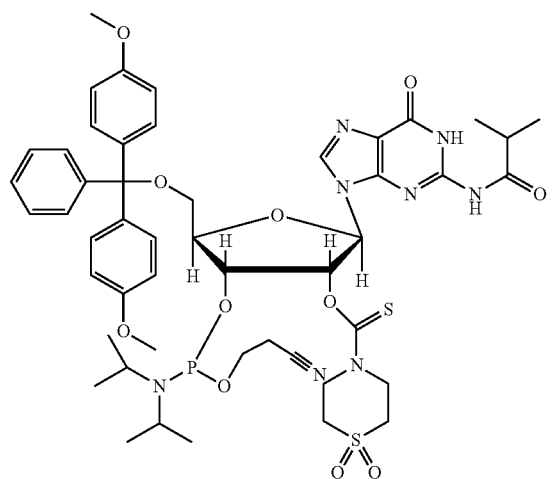
C₄₉H₆₁N₈O₁₁PS₂
Mol. Wt.: 1033.16

2'-O-(1,1-dioxo-1λ⁶-thiomorpholine-4-carbothioate)-5'-O-(4,4'-dimethoxytrityl)-N²-isobutyryl-guanosine 2'-O-(1,1-dioxo-1λ⁶-thiomorpholine-4-carbothioate)-N²-isobutyryl-guanosine (5.17 g, 9.74 mmol), dried by Me-THF co-evaporation (2×50 mL) was suspended in a 1:1 mixture of DCM/Me-THF (195 mL, 0.05M), then 4,4'-dimethoxytrityl chloride (2.48 g, 7.3 mmol) and NMM (0.803 mL, 7.3 mmol) were added in 2 portions (50% then 25%) while stirring. The reaction was complete in 30 min.

2'-O-(1,1-dioxo-1λ⁶-thiomorpholine-4-carbothioate)-5'-O-(4,4'-dimethoxytrityl)-N2-isobutyryl-guanosine-3'-O-(β-cyanoethyl)-N,N-diisopropyl-phosphoramidite 2-Cyanoethyl N,N-diisopropylchlorophosphoramidite (1.63 mL, 7.3 mmol) was added to the reaction mixture, followed by addition of NMM (0.803 mL, 7.3 mmol) and stirred at RT for 2 h. Side products were extracted with saturated NaHCO₃ (195 mL). Organic phase was dried with Na₂SO₄ (20 g) and filtered into hexanes (1000 mL). The suspension was put to the freezer for 2 h. Solvent was decanted and the crude product was immediately dissolved in dry DCM (25 mL) and loaded to a pre-neutralized silica gel column (75 g silica gel). Neutralization of silica gel: silica gel was suspended in 10% acetone/hexanes containing 1% TEA and poured into a flash chromatography column. TEA was washed off from the silica gel with 10% acetone/hexanes (500 mL) containing 0.1% TEA. Then crude product was introduced carefully on the column and eluted with 10-35 acetone/hexanes (0.1% TEA) in around 2.5 L volume of solution. The solvents were evaporated. Product was a diastereomeric mixture of nucleoside phosphoramidites, thus two spots on TLC. Product was redissolved in DCM and evaporated to produce foam. Yield 6.0 g (60%). Reaction was followed by TLC (10% MeOH/DCM, 0.5% TEA, $R_f$=0.65).

Synthesis of 2'-O-(1,1-dioxo-1λ⁶-thiomorpholine-4-carbothioate)-5'-O-(4,4'-dimethoxytrityl)-N⁶-isobutyryl-adenosine-3'-O-(β-cyanoethyl)-N,N-diisopropyl-phosphoramidite (5)

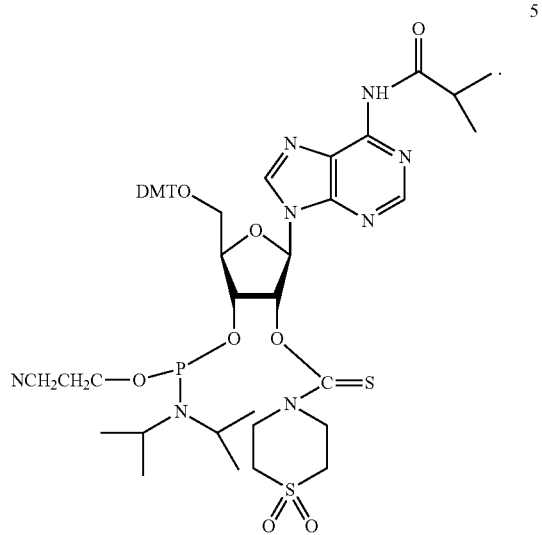

3',5'-O-(Tetraisopropyldisiloxane-1,3-diyl)-2'-O-(1-imidazole-carbothioate)-N⁶-isobutyryl-riboadenosine. 3',5'-(Tetraisopropyldisiloxane-1,3-diyl)-riboadenosine (N⁶-ibu) (20.29 g, 35 mmol) is dissolved in acetonitrile (140 mL, 0.25 M). 1,1'-thiocarbonyldiimidazole (6.87 g, 1.1 eq.) and 4-(dimethylamino)pyridine (427 mg, 0.1 eq.) are added and the reaction mixture is stirred for O/N at RT. After that time the reaction mixture is left in the freezer for 3 hours. The product (white solid) is filtered, washed with cold acetonitrile (3×40 mL) and dried on vacuum pump overnight. Isolated yield at this point 19.0 g (78.8%), $R_f$ (TLC EtOAc): 0.19, ESI-MS: 691 (M+1), 728 (M+K).

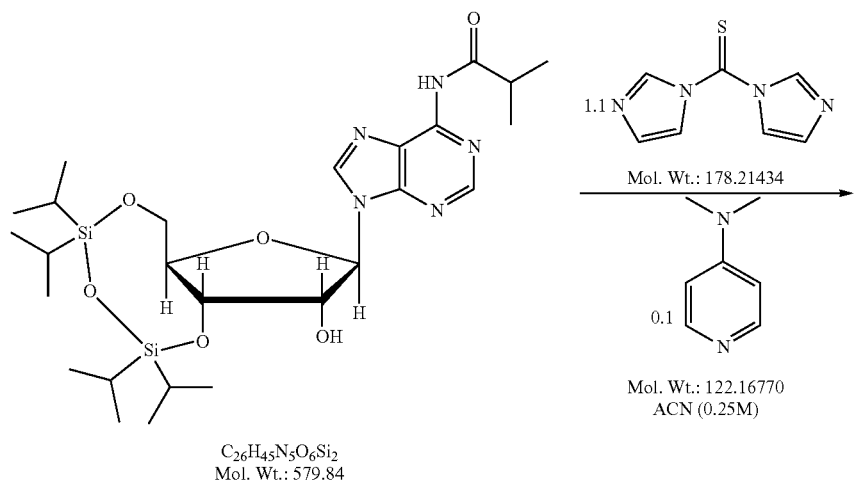

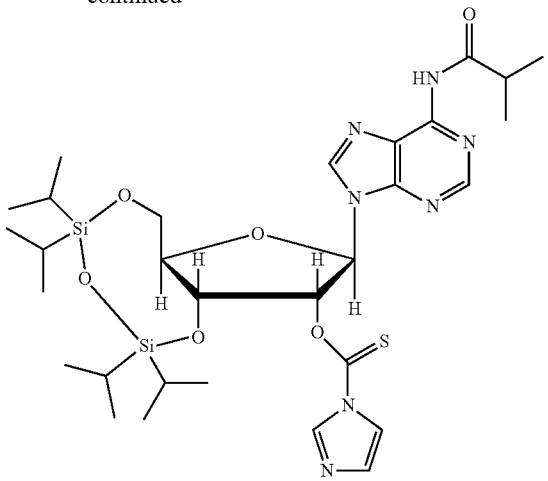

C$_{30}$H$_{47}$N$_7$O$_6$SSi$_2$
Mol. Wt.: 689.97
78.8%

3',5'-O-(Tetraisopropyldisiloxane-1,3-diyl)-2'-O-(1,1-dioxo-1λ$^6$-thiomorpholine-4-carbothioate)-N$^6$-isobutyryl-riboadenosine 3'-5'-O-(Tetraisopropyldisiloxane-1,3-diyl)-2'-O-(1-imidazole-carbothioate)-N$^6$-isobutyryl-riboadenosine (19.0 g, 27.6 mmol) and thiomorpholine 1,1-dioxide (4.48 g, 1.2 eq.) are suspended in acetonitrile (138 mL, 0.2 M). The mixture is heated up to 50° C. to dissolve and stirred for 3 hours at RT. The reaction mixture is concentrated to about half volume and left in the freezer for 2 hours. The product (white solid) is filtered, washed with cold acetonitrile (3×40 mL) and dried on vacuum pump overnight. Isolated yield 16.3 g (77.8%), R$_f$(TLC EtOAc): 0.40, ESI-MS: 757 (M+1), 795 (M+K), 1513 (dimer+1), 1535 (dimer+Na), 1551 (dimer+K).

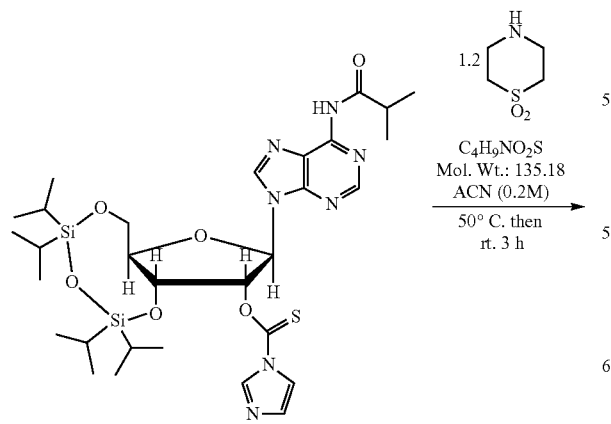

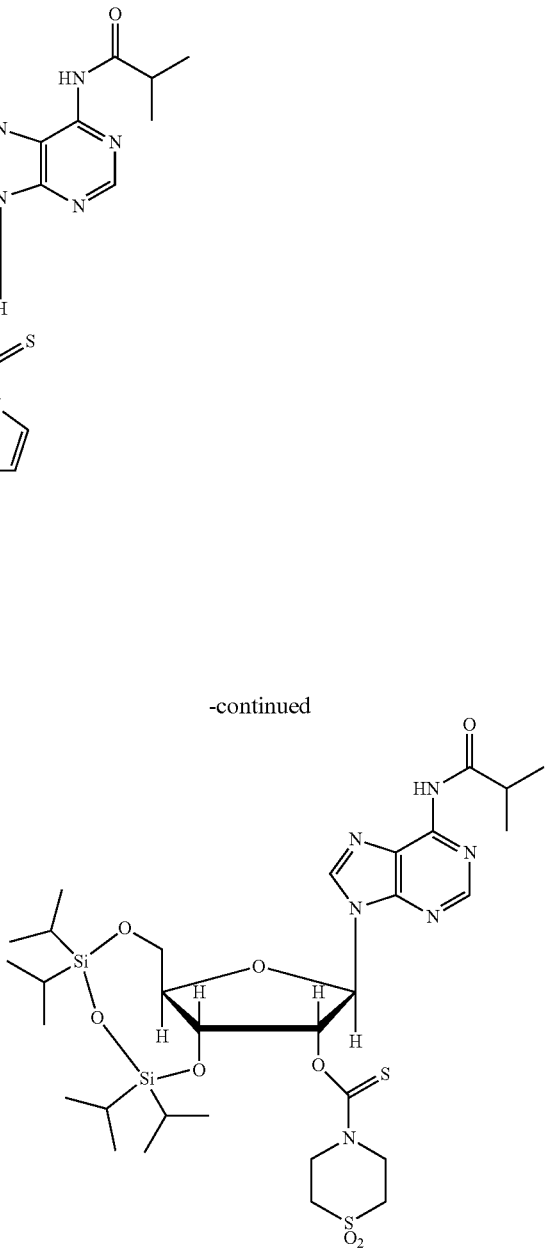

C$_{31}$H$_{52}$N$_6$O$_8$S$_2$Si$_2$
Mol. Wt.: 757.08
77.8%

2'-O-(1,1-dioxo-1λ$^6$-thiomorpholine-4-carbothioate)-N$^6$-isobutyryl-riboadenosine. Hydrogen fluoride pyridine complex (8.3 mL, 319.6 mmol HF, 14 eq.) is added to an ice-cold solution of pyridine (9.5 mL) in acetonitrile (55.4 mL). Deprotection mixture so formed is transferred to the flask with 3',5'-O-(tetraisopropyldisiloxane-1,3-diyl)-2'-O-(1,1-dioxo-1λ$^6$-thiomorpholine-4-carbothioate)-N$^6$-isobutyryl-riboadenosine (17.28 g, 22.8 mmol) and stirred for 2 hours at RT. The reaction was quenched with 5% aqueous CaCl$_2$ (300 mL) and the product was extracted with EtOAc. The organics were combined, dried with MgSO$_4$, filtered and evaporated. Isolated yield: 8.25 g (70.2%). R$_f$ (TLC 10% MeOH/chloroform): 0.30, ESI-MS: 515 (M+1), 552 (M+K), 1029 (dimer+1).

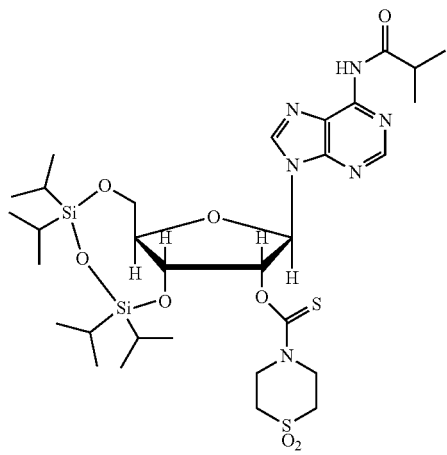

C₃₁H₅₂N₆O₈S₂Si₂
Mol. Wt.: 757.08

14 HFxPy
pyridine/
ACN
2 h rt

5'-O-(4,4'-Dimethoxytrityl)-2'-O-(1,1-dioxo-1λ⁶-thiomorpholine-4-carbothioate)-N⁶-isobutyryl-riboadenosine-3'-O-(β-cyanoethyl)-N,N-diisopropylphosphoramidite 2'-O-(1,1-dioxo-1λ⁶-thiomorpholine-4-carbothioate)-N⁶-isobutyryl-riboadenosine (8.25 g, 16.05 mmol) is dissolved in THF (160 mL, 0.1 M). Collidine (15.96 mL, ~7.5 eq.) and 4,4'-dimethoxytrityl chloride (6.8 g, 1.25 eq.) are added, and the reaction is left with stirring at RT for overnight. TLC (10% MeOH/chloroform) shows that reaction is complete after that time (R_f of the product 0.62). Collidine (2.12 mL, 1 eq.) and 1-methylimidazole (0.64 mL, 0.5 eq.) and then N,N-diisopropylamino cyanoethyl phosphonamidic chloride (9.5 g, 2.5 eq.) are added and the reaction mixture is stirred at RT for 2 hours. White solid (collidine hydrochloride) is filtered, washed with THF (2×50 mL) and then the solvent is evaporated off. The crude product is dissolved in acetonitrile (50 mL), loaded onto a silica gel column (8×30 cm) and purified by chromatography using hexanes/triethylamine (99/1) with a gradient of EtOAc (0-80%). The product may be then precipitated from hexanes (standard procedure). The isolated yield for this two-step synthesis was 9.44 g (57.8%), ESI-MS: 1017.3 (M+1), ³¹P NMR (CD₃CN): 149.95, 149.50.

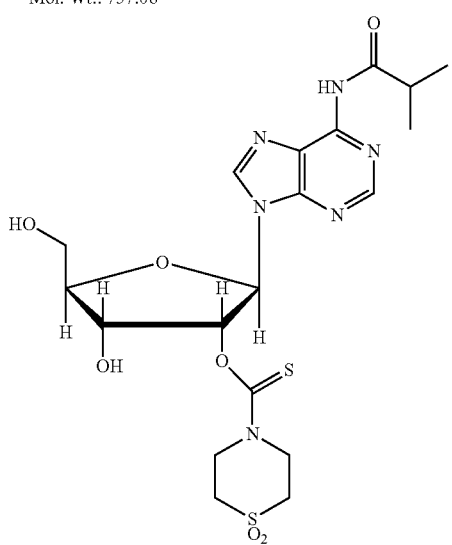

C₁₉H₂₆N₆O₇S₂
Mol. Wt.: 514.58
70.2%

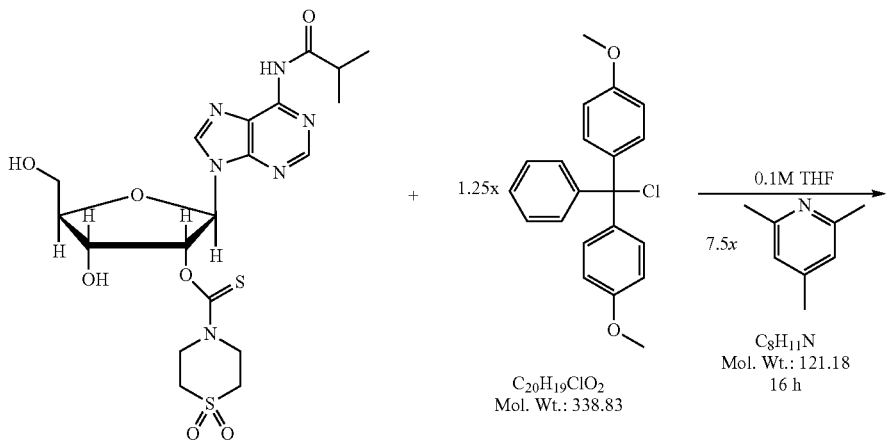

C₁₉H₂₆N₆O₇S₂
Mol. Wt.: 514.58

C₂₀H₁₉ClO₂
Mol. Wt.: 338.83

1.25x 0.1M THF
7.5x
16 h

C₈H₁₁N
Mol. Wt.: 121.18

-continued
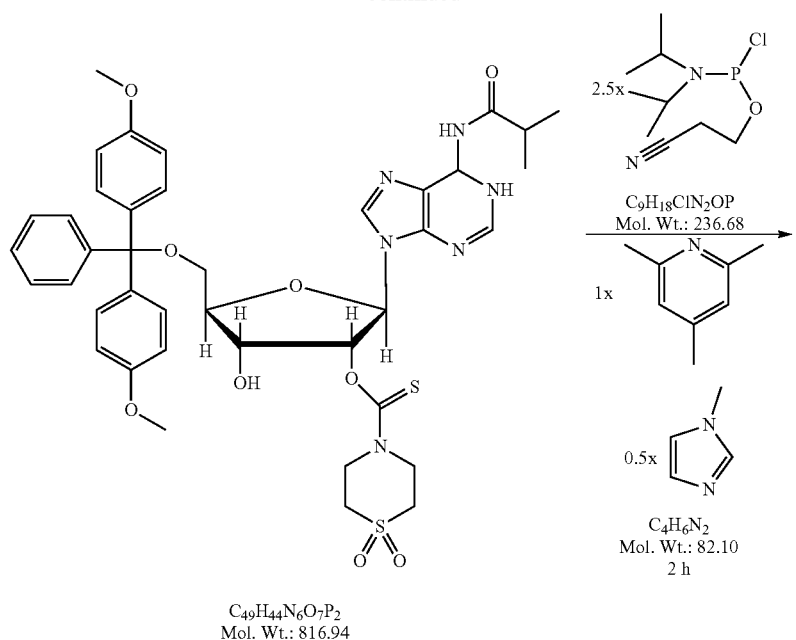
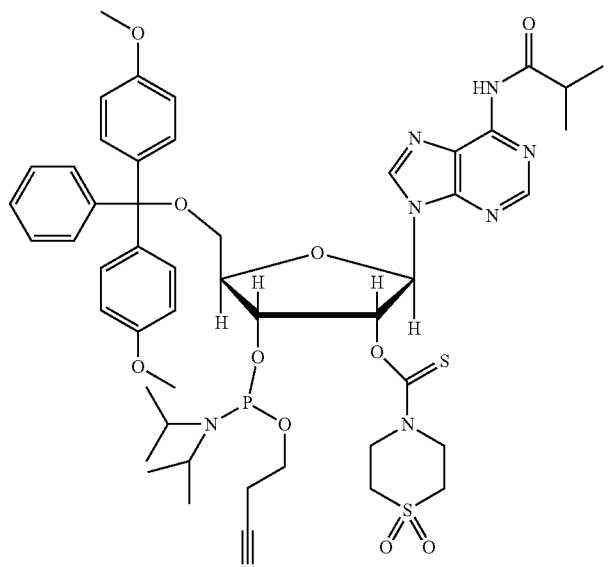

2'-O-(1,1-dioxo-1λ⁶-thiomorpholine-4-carbothioate)-
5'-O-(4,4'-dimethoxytrityl)-N²-acetyl-cytidine-3'-O-
(β-cyanoethyl)-N,N-diisopropyl-phosphoramidite
(6)

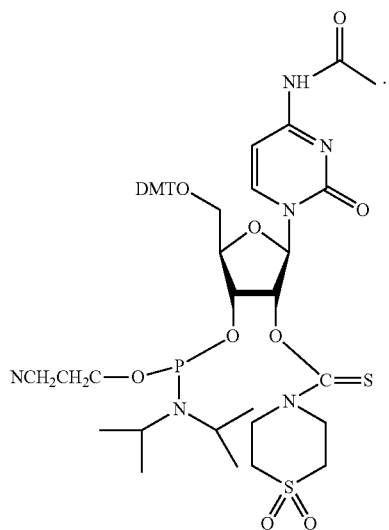

2'-O-(1,1-dioxo-1λ⁶-thiomorpholine-4-carbothioate)-N⁴-acetyl-cytidine. 3',5'-O-(Tetraisopropyldisiloxane-1,3-diyl)-N⁴-acetyl-cytidine (16.26 g, 30.8 mmol) was dissolved in DCM (44 mL, 0.7 M) and 1,1'-thiocarbonyldiimidazole (5.78 g, 32.44 mmol) was added and the mixture stirred for 1.75 h at ambient temperature. The following isolation is optional:

The reaction may be worked up at this step by cooling the reaction mixture, filtering the crystals and washing with DCM (3×60 mL). If no crystallization occurred then it may be initiated by standard methods. The combined filtrate (mother liquor) was evaporated and the residue re-crystallized from ACN (6 mL). Isolated yield: ~89%. R$_f$ (TLC 7% MeOH/DCM): 0.39 (same as starting material, MrC(Ac)). ¹H NMR: 10.95, s, 1H, NH, 8.58, t, 1H, Im, 8.04, d, 1H, C⁵ ᵒʳ ⁶, 7.89, t, 1H, Im, 7.23, d, 1H, C⁵ ᵒʳ ⁶, 7.11, q, 1H, Im, 6.3, d, 1H, 1', 5.96, s, 1H, 2', 4.8, m, 1H, 3', 4.15, m, 2H, 5', 4.0, m, 1H, 4', 2.1, s, 3H, CH₃, 1.89-0.75, m, 28H, TIPS.

Thiomorpholine-1,1'-dioxide (4.58 g, 33.88 mmol) was added followed by 100 mL ACN. Reaction mixture was heated up to ~50° C. to dissolve and stirred for 1.5 h at ambient temperature. The following isolation is again optional:

The solvents were evaporated and the residual crystals re-crystallized from ACN (17% solution). Yield: ~93% (2'-O-(1,1-dioxo-1λ⁶-thiomorpholine-4-carbothioate)-3',5'-O-(tetraisopropyldisiloxane-1,3-diyl)-N²-acetyl-cytidine product contained ~1 equivalent of imidazole as a contaminant). R$_f$ (TLC 7% MeOH/DCM): 0.51. ¹H NMR: 10.92, s, 1H, NH, 8.03, d, 1H, C⁵ ᵒʳ ⁶, 7.21, d, 1H, C⁵ ᵒʳ ⁶, 6.11, m, 1H, 1', 4.74, s, 1H, 2', 4.39, m, 2H, thiomorpholine, 4.21, m, 2H, thiomorpholine, 4.12, m, 1H, 4', 3.97, m, 1H, 3', 3.35, m, 2H, thiomorpholine, 3.1, m, 2H, thiomorpholine, 3.03-2.93, m, 2H, 5', 2.1, s, 3H, CH₃, 1.07-0.92, m, 28H, TIPS.

Hydrogen fluoride pyridine (HFxPy) (9.6 mL, 369.6 mmol) and pyridine (15 mL, 185.4 mmol) were added drop-wise. Reaction mixture might be cooled if warmed up. The mixture was stirred for 2 h at ambient temperature, while the product crystallized from the reaction mixture. The reaction mixture was cooled to −20° C., and filtered. The product was washed with ACN/DCM (5/2, 14 mL), and dried. Yield: 14.54 g (26.4 mmol, 85% for 3 steps, product contains 1 molar equivalent imidazolium fluoride salt and traces of silyl contamination). The salt contamination was removed by repeated extraction. The dried material (14.54 g) was suspended in water (300 mL) and extracted 7 times with ethyl acetate (600 mL each). Ethyl acetate phases were combined, dried with Na₂SO₄, filtered, evaporated and dried on vacuum at RT. Yield 11.9 g (84%). R$_f$ (TLC 7% MeOH/DCM): 0.2. ¹H NMR (ACN-d₃) δ (ppm): 10.94, s, 1H, NH, 8.29, d, 1H, C⁵ ᵒʳ ⁶, 7.23, d, 1H, C⁵ ᵒʳ ⁶, 6.16, m, 1H, 1', 5.77, m, 1H, 2', 5.66, m, 1H, 3'OH, 5.24, m, 1H, 5'OH, 4.52, m, 1H, thiomorpholine, 4.37, m, 1H, 3', 4.19, m, 1H, thiomorpholine, 4.03, m, 1H, 4', 4.01, m, 1H, thiomorpholine, 3.67, m, 2H, 5', 3.47, m, 1H, thiomorpholine, 3.29, m, 2H, thiomorpholine, 3.2, m, 2H, thiomorpholine, 2.08, s, 3H, CH₃.

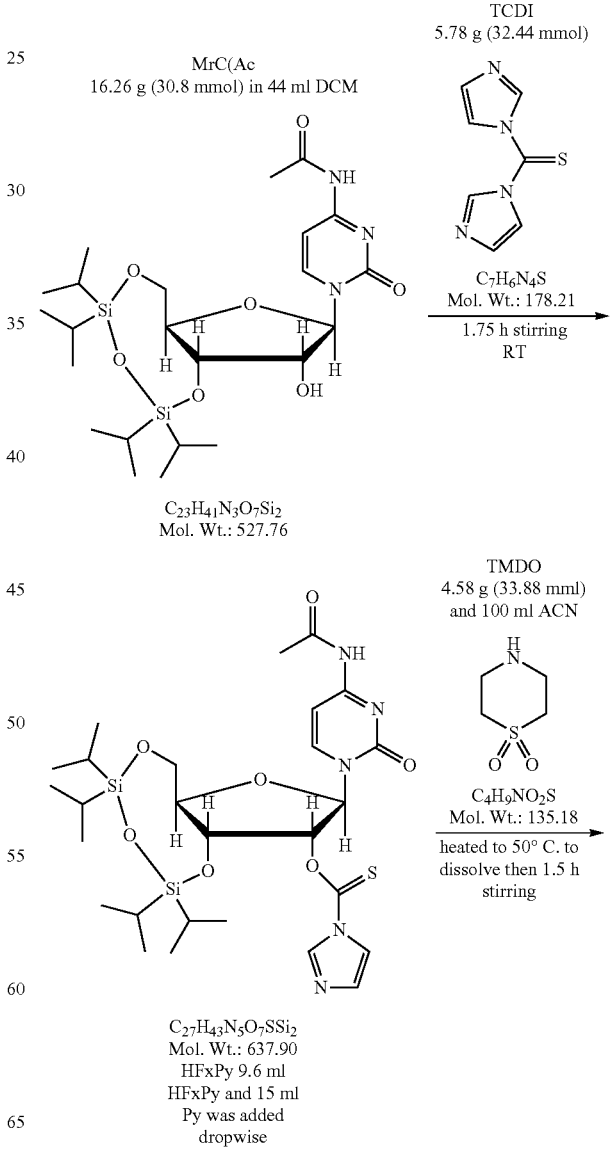

-continued

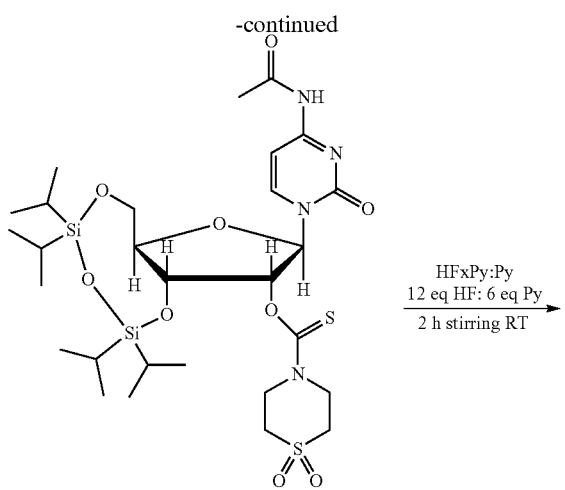

C$_{28}$H$_{48}$N$_4$O$_9$S$_2$Si$_2$
Mol. Wt.: 705.00

HFxPy:Py
12 eq HF: 6 eq Py
2 h stirring RT rC(Ac)TC
m = 11.9 g (84%)

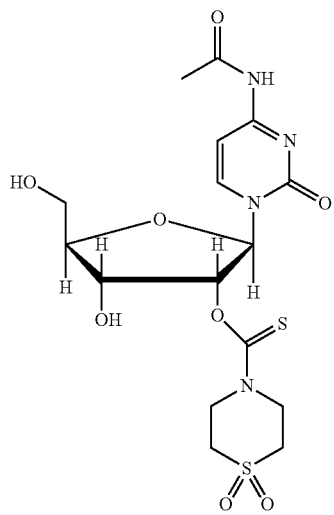

C$_{16}$H$_{22}$N$_4$O$_8$S$_2$
Mol. Wt.: 462.50

All solvents and reagents must be anhydrous in the following up to the final extraction step. 2'-O-(1,1-dioxo-1λ$^6$-thiomorpholine-4-carbothioate)-5'-O-(4,4'-dimethoxytrityl)-N$^4$-acetyl-cytidine.

2'-O-(1,1-dioxo-1λ$^6$-thiomorpholine-4-carbothioate)-N$^4$-acetyl-cytidine (6 g, 12.97 mmol) was dried by co-evaporation with anhydrous Py (2×50 mL). The dried rC(Ac)TC was then suspended in DCM (260 mL, 0.05 M), stirred then 4,4'-dimethoxytrityl chloride (4.83 g, 14.27 mmol) and NMM (1.43 mL, 12.97 mmol) were added. The reaction was complete in 30 min. The reaction may be worked up at this point:

The product was purified by chromatography: 0.1-2% MeOH/DCM. Yield: 7.94 g (80%). The product can be further purified by crystallization from iPrOH (110 mL), resulting in 7.1 g.

2'-O-(1,1-dioxo-1λ$^6$-thiomorpholine-4-carbothioate)-5'-O-(4,4'-dimethoxytrityl)-N$^4$-acetyl-cytidine-3'-O-(β-cyanoethyl)-N,N-diisopropyl-phosphoramidite 2-Cyanoethyl N,N-diisopropylchlorophosphoramidite (3.78 mL, 18.16 mmol) and NMM (2 mL, 18.16 mmol) were added and the mixture was stirred at RT for 2 h. Saturated NaHCO$_3$ (300 mL) was added to the reaction mixture, and the product extracted with DCM (100 mL). Organics were combined, dried with Na$_2$SO$_4$ (20 g) and filtered into hexanes (900 mL). The suspension was put in the freezer for O/N. Solvent was decanted and the residue immediately dissolved in dry DCM (50 mL), and loaded to a pre-neutralized silica gel column (100 g silica gel). Neutralization of silica gel: silica gel was suspended in 10% acetone/hexanes containing 1% TEA, and poured into a flash chromatography column. TEA was washed off from the silica gel with 20% acetone/hexanes (500 mL) containing 0.1% TEA. Then crude product was introduced carefully on column and eluted with 10-45% acetone/hexanes (0.1% TEA) (approximately 2.5 L volume of solution). First a yellow trityl compound is eluted at 30% then the product at 45%, but late fractions might be contaminated with hydrolyzed product (H-phosphonate and other colorful contaminants). The solvents were evaporated off the clean fractions. Product was a diastereomeric mixture of nucleoside phoshoramidites, thus two spots on TLC.

Product was co-evaporated with DCM to produce foam. Yield: 8.3 g (66%). Reaction was followed by TLC (10% MeOH/DCM, 0.5% TEA, R$_f$=0.5) Compound was identified by $^{31}$P, $^1$H NMR and mass spectroscopy. Yield: 67%. $^1$H NMR (ACN-d$_3$) δ: 8.88, s, 1H, NH, 8.09-8.02, dd, 1H, C$^5$ $_{or\ 6}$, 7.5, 7.35, 6.89, m, 13H, DMT, 7.1, dd, 1H, C$^{5\ or\ 6}$, 6.2, m, 1H, 1', 6.11, 6.08, m, 1H, 2', 4.8, 4.71, m, 1H, 3', 4.9, 4.65, m, 2H, thiomorpholine, 4.4, 4.35, m, 1H, 4', 4.05, 3.87, m, 2H, thiomorpholine, 3.49, m, 2H, iPr, 3.48, 3.41, m, 2H, 5', 2.77, m, 2H, thiomorpholine, 2.66, 2.53, m, 2H, thiomorpholine, 2.18, s, 6H, DMT, 2.14, s, 3H, CH$_3$, 1.25, m, 12H, iPr; 31P δ: 150.08, 149.35.

rC(Ac)TC
6 g (12.97 mmol)/DCM (260 ml)

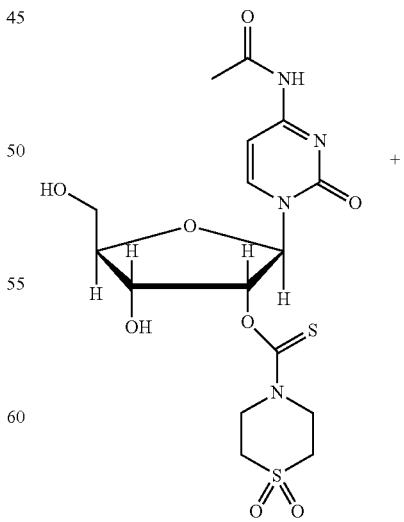

+

C$_{16}$H$_{22}$N$_4$O$_8$S$_2$
Mol. Wt.: 462.50

-continued

DMTCl
4.83 g (14.27 mmol)

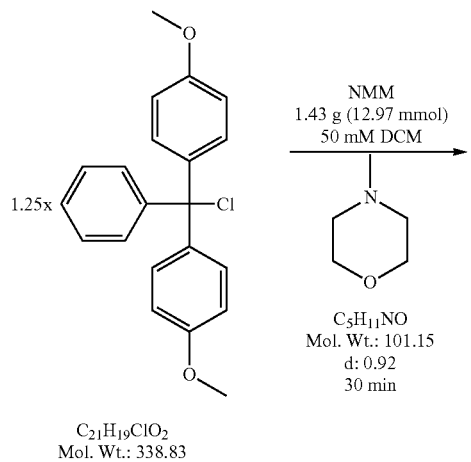

C$_{21}$H$_{19}$ClO$_2$
Mol. Wt.: 338.83

DMTrC(Ac)TC

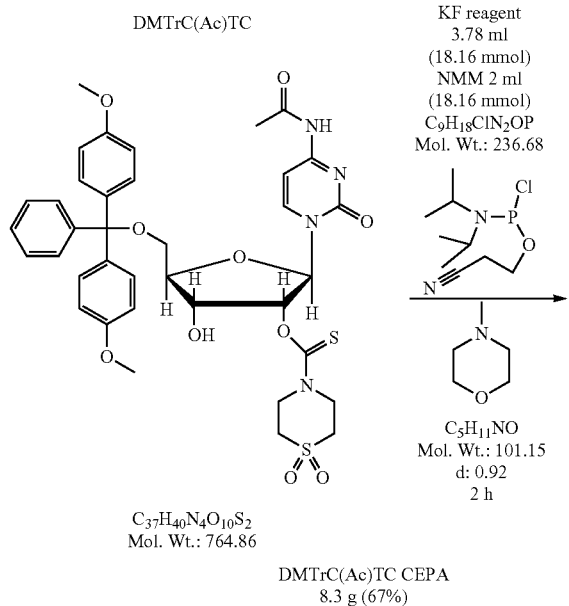

C$_{37}$H$_{40}$N$_4$O$_{10}$S$_2$
Mol. Wt.: 764.86

DMTrC(Ac)TC CEPA
8.3 g (67%)

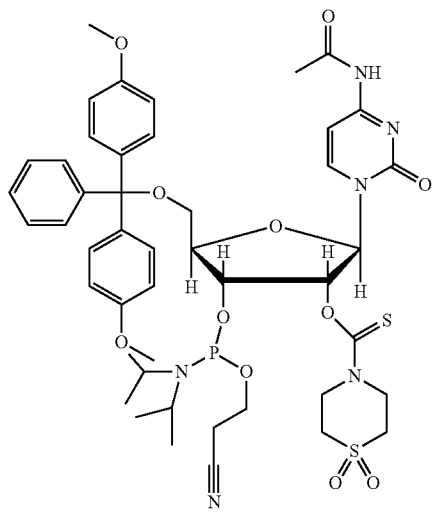

C$_{46}$H$_{57}$N$_6$O$_{12}$PS$_2$
Mol. Wt.: 965.0821

2'-O-(1,1-dioxo-1λ$^6$-thiomorpholine-4-carbothioate)-5'-O-(4,4'-dimethoxytrityl)-uridine-3'-O-(β-cyano-ethyl)-N,N-diisopropyl-phosphoramidite (7)

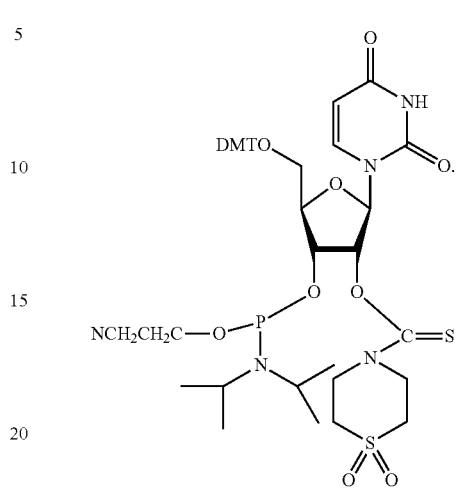

2'-O-(1,1-dioxo-1λ$^6$-thiomorpholine-4-carbothioate)-uridine. 3',5'-O-(Tetraisopropyldisiloxane-1,3-diyl)-uridine (7.3 g, 15 mmol) was dissolved in ACN (75 mL, 0.2 M) and 1,1'-thiocarbonyldiimidazole (2.8 g, 15.75 mmol) was added and the mixture stirred for 2 h at ambient temperature. The precipitated product was collected by filtration and dried for 2 h at RT in high vacuum (8.9 g 99%).

3',5'-O-(Tetraisopropyldisiloxane-1,3-diyl)-2'-O-(1,1-dioxo-1λ$^6$-thiomorpholine-4-carbothioate)-uridine (8.9 g, 15 mmol) was dissolved in Me-THF (75 mL, 0.2 M) and thiomorpholine-1,1-dioxide (2.23 g, 16.5 mmol) was added. Reaction mixture was stirred for 2 h at ambient temperature. Hydrogen fluoride pyridine (HFxPy) (2.33 mL, 90 mmol) and pyridine (5.05 mL, 63 mmol) were added drop-wise. Reaction mixture might be cooled if warmed up. The mixture was stirred for 2.5 h at ambient temperature. The reaction mixture was extracted with water (75 mL). The aqueous phase was extracted with Me-THF (2×150 mL), organics were combined and dried (100 g Na$_2$SO$_4$), filtered and evaporated. Yield 6.3 g (100%). R$_f$ (TLC 10% MeOH/DCM): 0.25.

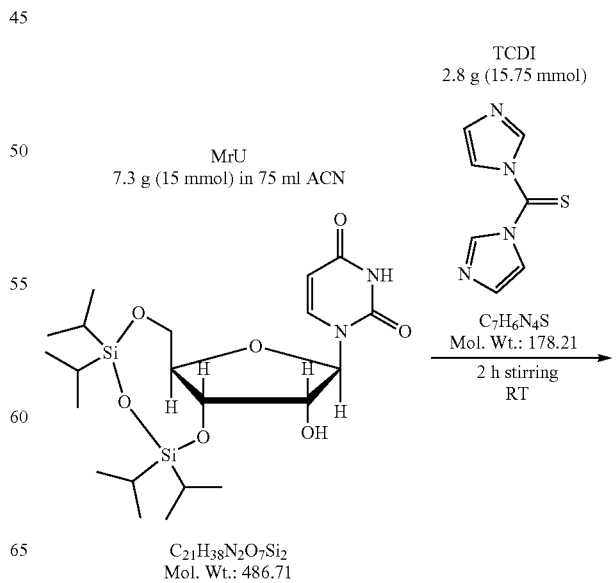

MrU
7.3 g (15 mmol) in 75 ml ACN

C$_{21}$H$_{38}$N$_2$O$_7$Si$_2$
Mol. Wt.: 486.71

-continued

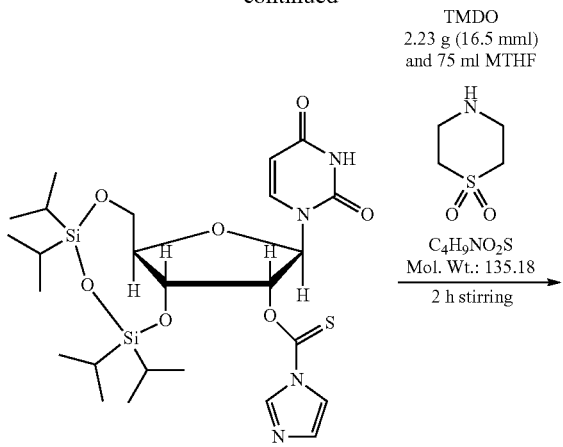

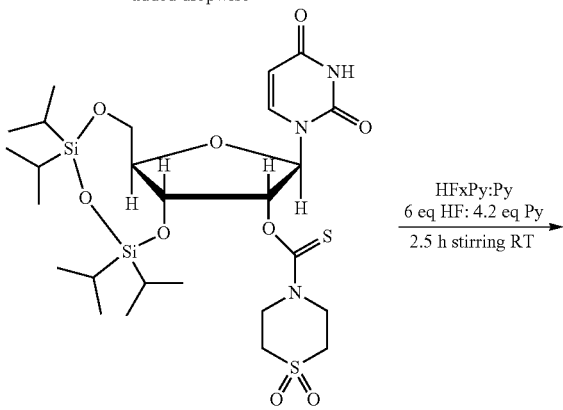

rU—TC
m = 6.3 g (100%)

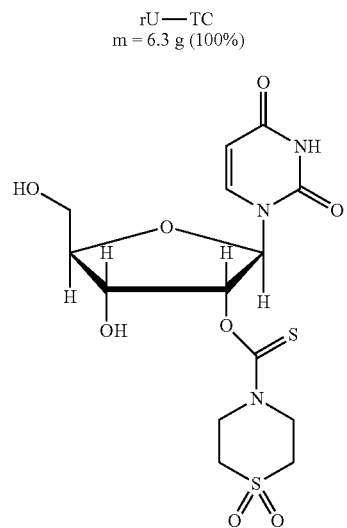

C₁₄H₁₉N₃O₈S₂
Mol. Wt.: 421.45

All solvents and reagents must be anhydrous in the following up to the final extraction step.

2'-O-(1,1-dioxo-1λ⁶-thiomorpholine-4-carbothioate)-5'-O-(4,4'-dimethoxytrityl)-uridine 2'-O-(1,1-dioxo-1λ⁶-thiomorpholine-4-carbothioate)-uridine (6 g, 14.2 mmol) was dried by co-evaporation with anhydrous Me-THF (2×50 mL). The dried rU-TC was then suspended in DCM/Me-THF (50%, 284 mL, 0.05 M), stirred then 4,4'-dimethoxytrityl chloride (3.81 g, 11.25 mmol) and NMM (1.24 mL, 11.25 mmol) were added in 2 portions (7.5+3.75 mmol). The reaction was complete in 30 min.

2'-O-(1,1-dioxo-1λ⁶-thiomorpholine-4-carbothioate)-5'-O-(4,4'-dimethoxytrityl)-uridine-3'-O-(β-cyanoethyl)-N,N-diisopropyl-phosphoramidite 2-Cyanoethyl N,N-diisopropylchlorophosphoramidite (2.51 mL, 11.25 mmol) and NMM (1.24 mL, 11.25 mmol) were added and the mixture was stirred at RT for 2 h. The reaction mixture was extracted with saturated NaHCO₃ (284 mL). Organic phase was dried with Na₂SO₄ (100 g) and evaporated to 50 mL and precipitated by dripping into hexanes (800 mL) and cooled for 2 h. Solvents were decanted, product was dissolved in DCM (20 mL), loaded to a pre-neutralized silica gel column (100 g silica gel). Neutralization of silica gel: silica gel was suspended in 10% acetone/hexanes containing 1% TEA, and poured into a flash chromatography column. TEA was washed off from the silica gel with 20% acetone/hexanes (500 mL) containing 0.1% TEA. Then crude product was introduced carefully on column and eluted with 10-35 acetone/hexanes (0.1% TEA) (approximately 2.5 L volume of solution). Pure compound fractions were coevaporated. Product was a diastereomeric mixture of nucleoside phoshoramidites, thus two spots on TLC.

Product was co-evaporated with DCM to produce foam. Yield: 9.52 g (72.5%). Reaction was followed by TLC (10% MeOH/DCM, 0.5% TEA, R$_f$=0.35). Compound was identified by ³¹P, ¹H NMR and mass spectroscopy.

rU—TC
6 g (14.2 mmol)/DCM/M—THF (284 ml)

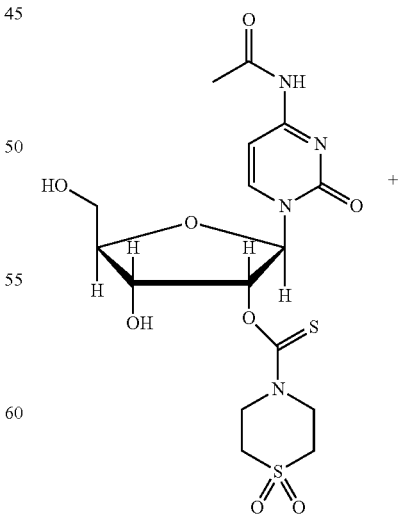

C₁₆H₂₂N₄O₈S₂
Mol. Wt.: 462.50

101
-continued

DMTCl
3.81 g (11.25 mmol)

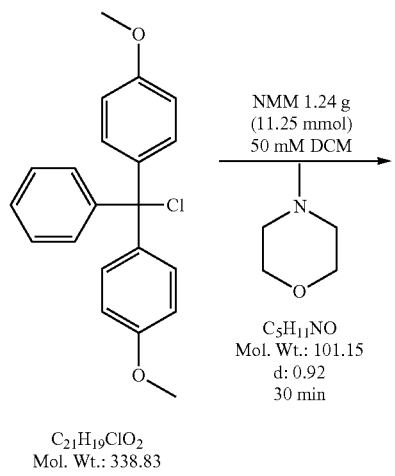

C$_{21}$H$_{19}$ClO$_2$
Mol. Wt.: 338.83

NMM 1.24 g
(11.25 mmol)
50 mM DCM

C$_5$H$_{11}$NO
Mol. Wt.: 101.15
d: 0.92
30 min

DMTrU—TC

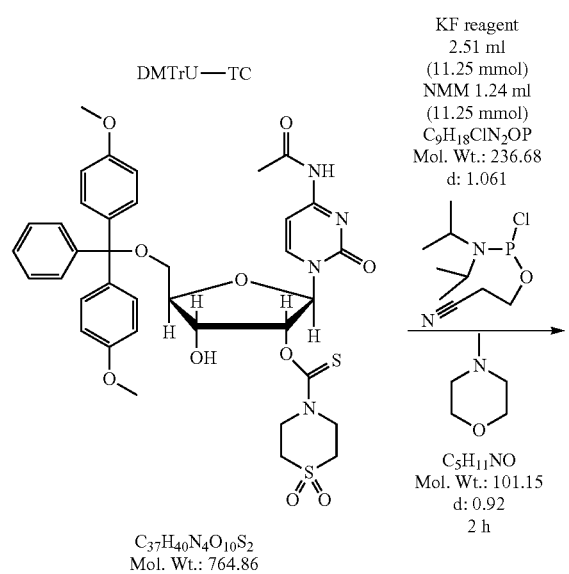

C$_{37}$H$_{40}$N$_4$O$_{10}$S$_2$
Mol. Wt.: 764.86

KF reagent
2.51 ml
(11.25 mmol)
NMM 1.24 ml
(11.25 mmol)
C$_9$H$_{18}$ClN$_2$OP
Mol. Wt.: 236.68
d: 1.061

C$_5$H$_{11}$NO
Mol. Wt.: 101.15
d: 0.92
2 h

102
-continued
DMTrU—TC CEPA
9.52 (72.5%)

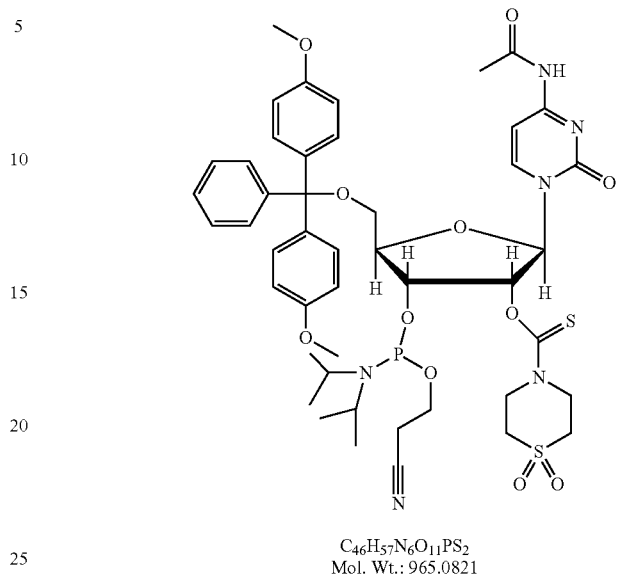

C$_{46}$H$_{57}$N$_6$O$_{11}$PS$_2$
Mol. Wt.: 965.0821

2'-O-(1,1-dioxo-1λ$^6$-thiomorpholine-4-carbothioate)-
5'-O-(4,4'-dimethoxytrityl)-N$^6$-benzoyl-adenosine-
3'-O-(β-cyanoethyl)-N,N-diisopropyl-phosphoramidite (8)

8

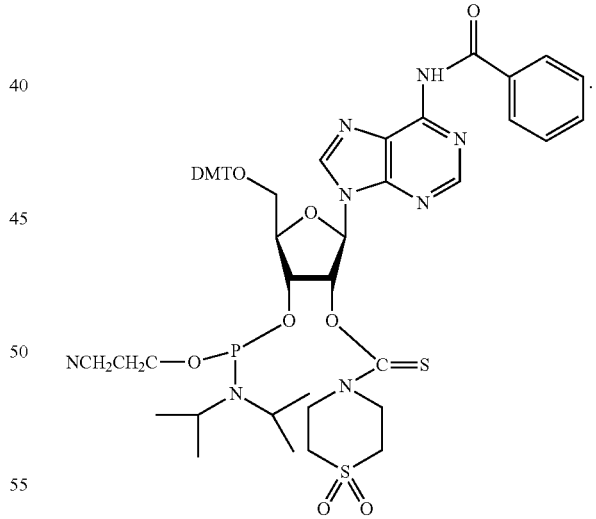

2'-O-(1,1-dioxo-1λ$^6$-thiomorpholine-4-carbothioate)-N$^6$-benzoyl-adenosine. 3',5'-O-(Tetraisopropyldisiloxane-1,3-diyl)-N$^6$-benzoyl-adenosine (6.14 g, 10 mmol) was dissolved in DCM (14 mL, 0.7 M) and 1,1'-thiocarbonyldiimidazole (1.88 g, 10.5 mmol) was added and stirred for 3.5 h at ambient temperature. Thiomorpholine-1,1-dioxide (1.487 g, 11 mmol) was added and stirred for 1.25 h at ambient temperature. ACN (30 mL) was then added to the reaction mixture.

Hydrogen fluoride pyridine (HFxPy) (3.1 mL, 120 mmol) and pyridine (5 mL) was added drop-wise. Reaction mixture might be cooled if warmed up. The mixture was stirred for 2 h at ambient temperature. Ethyl acetate (350 mL) was added resulting in precipitation. The suspension was extracted with water (400 mL) and the aqueous layer was extracted with EtOAc (2×500 mL). Organics were combined, dried with $Na_2SO_4$ (50 g), filtered and evaporated. The salt contamination was removed by repeated extraction. The dried material (5.66 g) was suspended in water (500 mL) and extracted with ethyl acetate (5×500 mL). Ethyl acetate phases are combined, dried with $Na_2SO_4$, filtered, evaporated and dried by evaporation with pyridine (2×50 mL). Yield 5.65 g (>100%, pyridine up to 5% can be seen in $^1H$). $R_f$ (TLC 5% MeOH/DCM): 0.52.

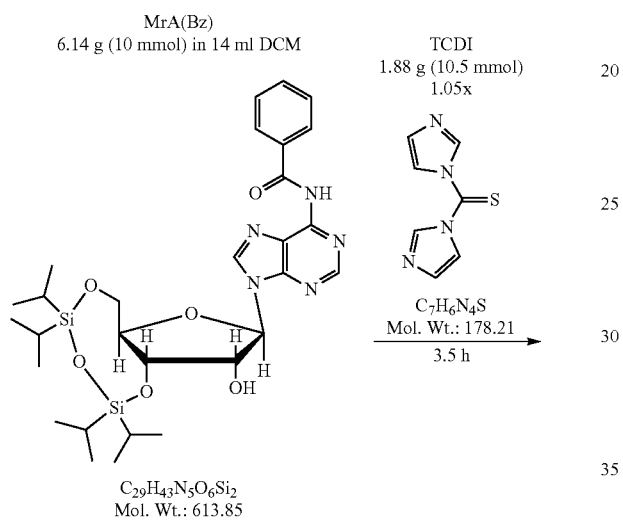

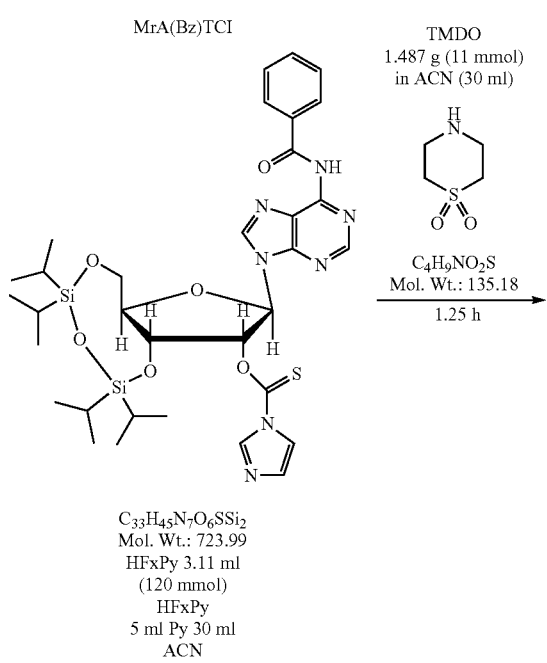

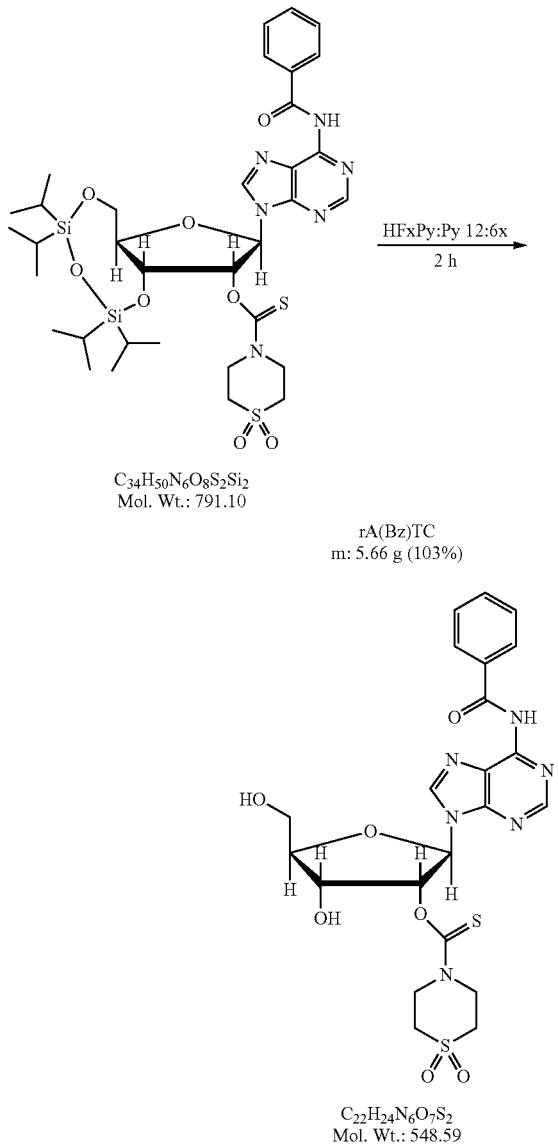

All solvents and reagents must be anhydrous in the following up to the final extraction step.

2'-O-(1,1-dioxo-1$\lambda^6$-thiomorpholine-4-carbothioate)-5'-O-(4,4'-dimethoxytrityl)-$N^6$-benzoyl-adenosine 2'-O-(1,1-dioxo-1$\lambda^6$-thiomorpholine-4-carbothioate)-$N^6$-benzoyl-adenosine (5.49 g, 10 mmol), dried by pyridine co-evaporation was suspended in DCM (200 mL, 0.05 M), then 4,4'-dimethoxytrityl chloride (4.07 g, 12 mmol) and NMM (1.1 mL, 10 mmol) were added while stirred. The reaction was complete in 30 min. 2'-O-(1,1-dioxo-1$\lambda^6$-thiomorpholine-4-carbothioate)-5'-O-(4,4'-dimethoxytrityl)-$N^6$-benzoyl-adenosine-3'-O-($\beta$-cyanoethyl)-N,N-diisopropyl-phosphoramidite.

2-Cyanoethyl N,N-diisopropylchlorophosphoramidite (2.9 mL, 13 mmol) and NMM (1.54 mL, 14 mmol) were added to the reaction mixture and stirred at RT for 2 h. Saturated $NaHCO_3$ (200 mL) was added and the product extracted with DCM (3×100 mL). Organics were combined, dried with Na$_2$SO$_4$ (20 g) and filtered into hexanes (600 mL). The suspension was frozen overnight. Solvent was decanted and the crude product was immediately dissolved in dry DCM (50 mL) and loaded to a pre-neutralized silica gel column (200 g silica gel). Neutralization of silica gel: silica gel was suspended in 10% acetone/hexanes containing 1% TEA and poured into a flash chromatography column. TEA was washed off from the silica gel with 20% acetone/hexanes containing 0.1% TEA (500 mL). Then crude product was introduced carefully on top of the column and eluted with 20-45 acetone/hexanes (0.1% TEA) in around 2.5 L volume of solution (first a yellow trityl compound was eluted at around 30% then the product at 45%, but late fractions might be contaminated with hydrolyzed product and colorful contaminant). The solvents were evaporated. Product was a diastereomeric mixture of nucleoside phosphoramidites, thus two spots on TLC.

Product was redissolved in DCM and evaporated to produce foam m=6.74 g (65%). Reaction was followed by TLC (8% MeOH/DCM, 0.5% TEA, R$_f$=0.35) Compound was identified by $^{31}$P, $^1$H NMR and mass spectroscopy. Yield: 64%.

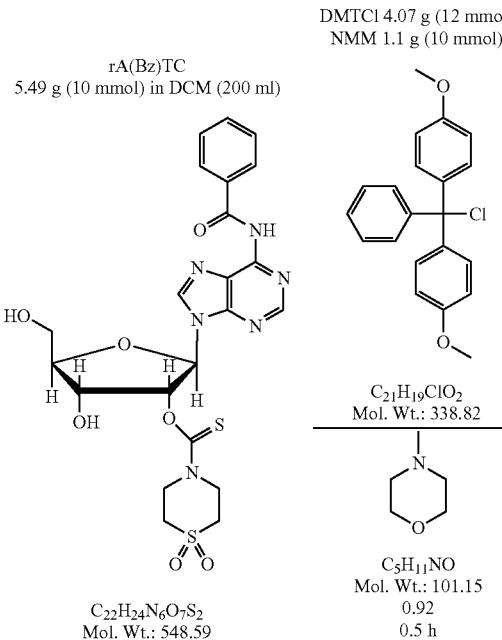

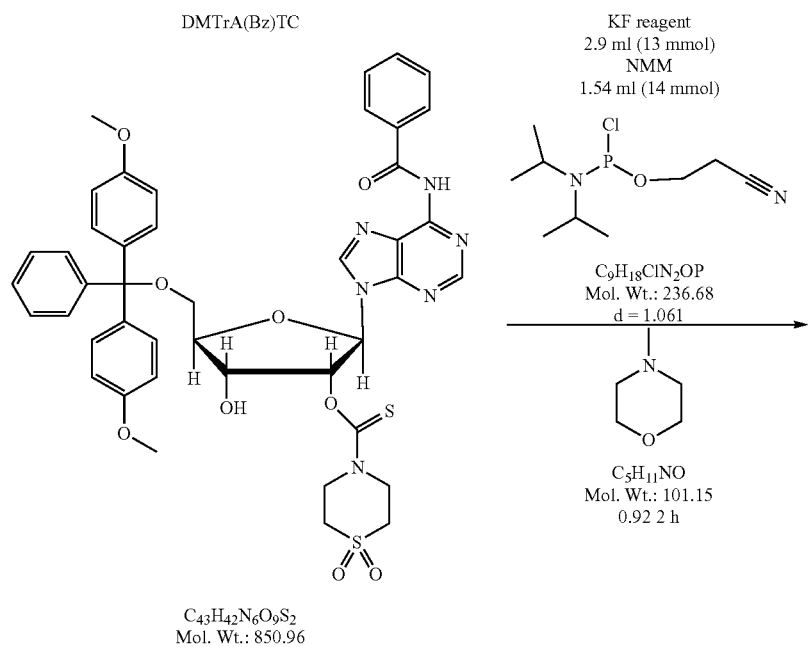

DMTrA(Bz)TC CEPA
6.74 g (64%)

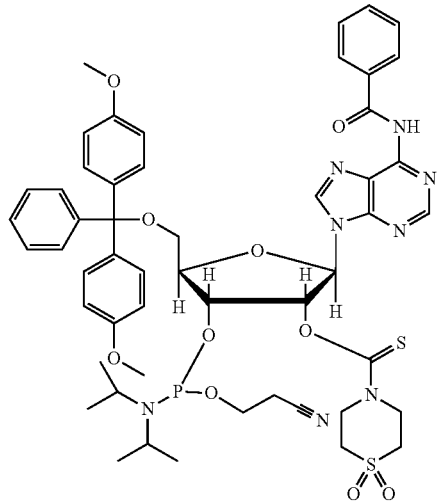

C$_{52}$H$_{59}$N$_8$O$_{10}$PS$_2$
Mol. Wt.: 1051.18

General Procedure for Oligoribonucleotide Synthesis on Solid Support

Syntheses were typically performed on a 1 micromole scale using dT-CPG columns from Glen Research according to the standard RNA cycle on an ABI 394 DNA/RNA synthesizer. For the coupling step, phosphoramidite and tetrazole (or S-ethylthiotetrazole) were delivered to the synthesis column and left for 10 minutes. After completion of all synthesis steps, and in order to remove the methyl protecting group on the phosphate moieties, the oligoribonucleotide (still joined to CPG) was treated with a 1 M solution of disodium 2-carbamoyl-2-cyanoethylene-1,1-dithiolate in DMF (1 mL) for 30 minutes at room temperature, and then washed with water followed by acetonitrile and dried by argon. Alternatively, 2'-protected oligonucleotides containing the cyanoethyl phosphate protecting group could be cleaved using 20% diethylamine in anhydrous acetonitrile for one hour at room temperature (cyanoethyl phosphate protecting groups can be also be removed during the subsequent treatment by 1,2-diaminoethane, without pretreatment with diethylamine).

Oligomers were cleaved from solid support and 2'-deprotected by treatment with neat diamines (e.g. 1,2-diaminoethane) for several hours (2, 6, 17, 24 h) at room temperature or 1,2-diaminoethane dissolved in organic solvents for various times. After washing with acetonitrile, the completely deprotected oligoribonucleotide was washed from the CPG column with water and analyzed with HPLC [ODS-Hypersil (5m), column 4.0×250, flow 1.5 mL/min, 0-20% MeCN in 50 mM TEAB (linear gradient) in 40 min; Alternatively IEX-HPLC (A buffer: 0.15 M TRIS 15% ACN pH set to 8 by formic acid, B buffer: 1 M LiCl in A. Column: DIONEX DNAPac P200 4×250 mm, 1 ml/min flow, 0-80% B in 20 min at 70° C.)]. HPLC-MS buffer systems [(A: 0.2 M HFIP, 8 mM TEA, 5% MeOH pH 7.4, B: MeOH, column: Waters) (Bridge C$_{18}$ 2.5 μm, 2.1×50 mm, 0.2 ml/min flow, 1-25% in 20 min at 55° C.) were applied also].

To investigate solvent effect on 1,2-diaminoethane deprotection a 16-mer with only one uridine on 5'-end (5'-UT$_{15}$-3') was synthesized using 5'-O-(4,4'-dimethoxytrityl)-3'-O-methyl-N,N-diisopropyl-phosphoramidite-2'-O-(1,1-dioxo-1λ$^6$-thiomorpholine-4-carbothioate)-uridine on a dT CPG solid support. This compound was deprotected using various solutions of 1,2-diaminoethane and the products evaluated by HPLC. Neat 1,2-diaminoethane gave complete deprotection of the 2'-O-(1,1-dioxo-1λ$^6$-thiomorpholine-4-carbothioate) protecting group in 1 hour. The deprotections were then repeated in 7.5 M solutions of 1,2-diaminoethane in various organic solvents (MeCN, 1,4-dioxane, THF, Me-THF, toluene, DCM, iPrOH, HFIP, morpholine, MeOH). In most cases addition of solvent had a negligible effect on removal of the 2'-protecting group. In other words, solutions of diaminoethane removed the 2'-O-(1,1-dioxo-1λ$^6$-thiomorpholine-4-carbothioate) protecting group at similar rate as in neat diaminoethane. (MeOH solution dissolved the oligonucleotide yielding only ~40% product). For deprotection of 5'-U$_{15}$T-3' in similar attempts, only the toluene solution of diamine worked comparably to neat 1,2-diaminoethane.

Various diamines have been investigated for deprotection of the 2'-O-(1,1-dioxo-1λ$^6$-thiomorpholine-4-carbothioate) protecting group. 5'-U(TC)T$_{15}$-3' 16-mer was treated with different neat diamines (such as 1,2-diaminoethane; 1,2-diaminopropane; 1,3-diaminopropane; 1,4-diaminobutane; 2,2'-diaminodiethylamine; 2,2-dimethyl-1,3-propanediamine; 1,2-diamino-2-methylpropane; 2-(diisopropylamino) ethylamine; N-(2-aminoethyl)-1,2-diaminoethane; 1,3-diamino-2-propanol and 4,7,10-trioxa-1,13-tridecanediamine). Only with the first five diamines (in the bracketed list above), are 80% or more of the 2'-protecting groups removed in 2 hours at RT. Other substituted diamines gave only 10-20% deprotection after 2 hours.

When the same conditions were applied for deprotection of 5'-U(TC)$_{15}$T-3' or a oligoribonucleotide 21mer (5'-GUG UCA GUA CAG AUG AGG CCT-3'-CPG) (SEQ ID NO. 1) diaminoethane gave similar results (complete deprotection in 2 hours). Other substituted diamines like: 1,3-diaminopropane, 2,2'-diaminodiethylamine, 1,2-diaminopropane and 1,4-diaminobutane removed the 2'-protecting groups and all N² isobutyryls (from G) in 24 h. The longer contact time (24 hours) with the RNA 21-mer oligonucleotide resulted in 15-45% degradation also.

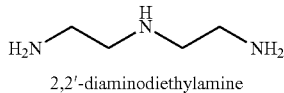
2,2'-diaminodiethylamine

A 21-mer oligoribonucleotide was synthesized on a dT CPG solid support (5'-GUG UCA GUA CAG AUG AGG CCT-3') (SEQ ID NO. 1) using 2'-O-(1,1-dioxo-1$\lambda^6$-thiomorpholine-4-carbothioate)-5'-O-(4,4'-dimethoxytrityl)-N²-acetyl-cytidine-3'-O-(β-cyanoethyl)-N,N-diisopropyl-phosphoramidite, 2'-O-(1,1-dioxo-1$\lambda^6$-thiomorpholine-4-carbothioate)-5'-O-(4,4'-dimethoxytrityl)-N⁶-benzoyl-adenosine-3'-O-(β-cyanoethyl)-N,N-diisopropyl-phosphoramidite, 2'-O-(1,1-dioxo-1$\lambda^6$-thiomorpholine-4-carbothioate)-5'-O-(4,4'-dimethoxytrityl)-N²-isobutyryl-guanosine-3'-O-(β-cyanoethyl)-N,N-diisopropyl-phosphoramidite and 2'-O-(1,1-dioxo-1$\lambda^6$-thiomorpholine-4-carbothioate)-5'-O-(4,4'-dimethoxytrityl)-uridine-3'-O-(β-cyanoethyl)-N,N-diisopropyl-phosphoramidite monomers. The synthesis was performed on a 21 micromole scale on an ÄKTA Oligopilot 10 DNA synthesizer from GE Healthcare (formerly Amersham Biosciences). The coupling was done with a standard RNA 15 minute recycling time and S-ethyltetrazole was used as an activator. Post-synthesis, the solid support was treated with 20% diethylamine in acetonitrile to remove the cyanoethyl phosphate protecting group, washed with acetonitrile and dried with a stream of argon. Alternatively the cyanoethyl phosphate protecting groups were removed without prior treatment with diethylamine, during the 1,2-diaminoethane step that follows. The support was then treated with neat 1,2-diaminoethane for 2-24 hours at room temperature. Under the above conditions 2'-O-(1,1-dioxo-1$\lambda^6$-thiomorpholine-4-carbothioate) protecting groups, cyanoethyl phosphate protection, and the heterobase protecting groups were removed and the oligomer was cleaved from the solid support (CPG), but still associated (adsorbed) to its surface. The solid support was washed with acetonitrile, dried (on vacuum or argon flush) and then the oligonucleotide dissolved by washing the solid support with water or an aqueous buffer. The product was analyzed by HPLC and mass spectrometry.

ABBREVIATIONS

In this disclosure, the following abbreviations have the following meanings. Abbreviations not defined have their generally accepted meanings.

° C.=degree Celsius; RT=room temperature (21° C.); hr or h=hour; min=minute; sec=second; μM=micromolar; mM=millimolar; M=molar; mL=milliliter; μl=microliter; mg=milligram; μg=microgram; O/N=overnight; NMM=N-methylmorpholine; DMAP=N,N dimethylaminopyridine; DMT=4,4'-dimethoxytrityl; NMI=N-methylimidazole; TBAF=tetrabutylammonium fluoride; TBAOH=tetrabutylammonium hydroxide; TBAA=tetrabutylammonium acetate; TBAB=tetrabutylammonium bromide; TBDMS=tert-butyl-dimethylsilyl; TIPS=1,3-tetraisopropyl disiloxane; TEA=triethylamine; TEMED=N,N,N',N'-tetramethylethylenediamine; TEAA=triethylammonium acetate; TEAB=triethylammonium bicarbonate; HFIP=1,1,1,3,3,3-hexafluoroisopropanol; KF reagent=chlorophosphite reagent=2-Cyanoethyl N,N-diisopropylchlorophosphoramidite; DCM=dichloromethane; Me-THF=2-methyl-tetrahydrofurane; EtOAc=ethylacetate; thionocarbamate=amine-substituted carbothioate=—O—C(=S)—NR¹R²; IE=ion exchange; RP-HPLC=Reverse Phase High Performance Liquid Chromatography.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of deprotecting a polynucleotide bound to a solid support with a succinyl linker, a hydroquinone —O,O'-diacidic acid linker (Q-linker), an oxalyl linker or a succinyl derivative of 8,9-Dihydroxy-4-phenyl-10-oxa-4-aza-tricyclo[5.2.1.02,6]decane-3,5-dione (Unylinker), the polynucleotide comprising at least one 2'-protected ribonucleotide having:

a phosphate protecting group, wherein the phosphate protecting group is beta cyanoethyl or methyl;

a 2'-protecting group, wherein the 2'-protecting group is selected from tertbutyldimethylsilyl (TBDMS), triisopropylsilyloxymethyl (TOM) or 2'-O-bis(2-acetoxyethoxy)methyl (ACE); and optionally a nucleobase-protecting group, wherein the nucleobase-protecting group is an exocyclic amine protecting group; and wherein the method comprises:

(a) contacting the solid support bound polynucleotide with a first composition comprising a phosphate deprotection reagent and removing the phosphate protecting group, thereby producing a first deprotected polynucleotide bound to the solid support;

(b) contacting said first deprotected polynucleotide bound to the solid support with a second composition comprising a 2'-deprotection reagent and removing the 2'-protecting group, thereby producing a second deprotected polynucleotide bound to the solid support; and (c) after step (b) has been completed, contacting said second deprotected polynucleotide bound to the solid support with a third composition comprising a diamine, wherein the diamine comprises two amino groups connected by a linker of 2 to 12 atoms in length, in organic solvent, gas-phase or neat, and cleaving the linker and also removing the nucleobase protecting group, if present, and thereby producing a deprotected, cleaved polynucleotide which is retained on the solid support.

2. The method of claim 1, wherein the method further comprises:

(d) washing the deprotected, cleaved polynucleotide retained on the solid support with an organic solvent; and (e) eluting the deprotected, cleaved polynucleotide from the solid support.

3. The method of claim 1, wherein the diamine comprises two primary amino groups.

4. The method of claim 1, wherein the diamine comprises two primary amino groups connected by a linker of about 2 to 6 atoms in length.

5. The method of claim 1, wherein the diamine is selected from 1,2-diaminoethane, 1,2-diaminopropane, 1,3-diaminopropane, 1,4-diaminobutane, N-ethyl-1,2-diaminoethane and 2,2'-diaminodiethylamine, and any mixtures thereof.

6. The method of claim 1, wherein the third composition comprises at least 50% by volume 1,2-diaminoethane in solution, with water content not exceeding 20% v/v.

7. The method of claim 1, wherein the third composition comprises 1,2-diaminoethane and an organic solvent.

8. The method of claim 1, wherein the third composition contains less than 100% diamine and the non-diamine portion of the third composition comprises acetonitrile, tetrahydrofuran (THF), 2-methyl-tetrahydrofuran (2-methyl-THF), toluene, dichloromethane (DCM), 1,4-dioxane, morpholine or any mixtures thereof.

9. The method of claim 1, wherein the solid support is selected from a controlled-pore gas (CPG) support and a polystyrene support.

10. The method of claim 1, wherein the nucleobase is selected from U, $N^6$-benzoyl-A, $N^6$-isobutyryl-A, $N^6$—(N,N)-dimethylacetamidine-A, $N^6$—(N,N)-dibutylformamidine-A, $N^6$-phenoxyacetyl-A, $N^6$-4-tert-butylphenoxyacetyl-A, $N^4$-acetyl-C, $N^4$-isobutyryl-C, $N^4$-phenoxyacetyl-C, $N^4$-4-tert-butylphenoxyacetyl-C, $N^2$-isobutyryl-G, $N^2$—(N,N)-dibutylformamidine-G, $N^2$—(N,N)-dimethylformamidine-G, $N^2$-phenoxyacetyl-G and $N^2$-4-tert-butylphenoxyacetyl-G.

11. The method of claim 1, wherein:

the phosphate deprotection reagent is selected from diethylamine, t-butylamine, diaza(1,3)bicyclo[5.4.0]undecane (DBU), thiophenol, or disodium 2-carbamoyl-2-cyanoethylene-1,1-dithiolate.

12. A method of deprotecting a polynucleotide synthesized on solid support and comprising one or more ribonucleotide moieties containing 2'-protecting groups, wherein the 2'-protecting group is selected from a thionocarbamate protecting group, tertbutyldimethylsilyl (TBDMS), triisopropylsilyloxymethyl (TOM) or 2'-O-bis(2-acetoxyethoxy)methyl (ACE), the method comprising the following steps:

(1) providing a solid support having said synthesized polynucleotide attached thereto, and (2) simultaneously or after having removed the 2'-protecting groups of said polynucleotide, incubating the solid support with a composition comprising a diamine; and thereby deprotecting and cleaving the polynucleotide from the solid support;

(3) removing the composition while the polynucleotide is retained on the solid support; and (4) optionally, washing the solid support with an organic solvent;

wherein the diamine is 1,2-diaminoethane or a substituted 1,2-diaminoethane having the structure of Formula (VII)

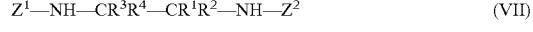

$$Z^1\text{—NH—}CR^3R^4\text{—}CR^1R^2\text{—NH—}Z^2 \qquad (VII)$$

wherein $R^1$, $R^2$, $R^3$, $R^4$ are independently selected from: H, a hydrocarbyl, a substituted hydrocarbyl, an aryl, and a substituted aryl; and wherein $Z^1$ and $Z^2$ are each independently selected from H, hydrocarbyl, substituted hydrocarbyl, aryl, substituted aryls, alkyl-substituted amine, and aminoalkyl-substituted amine.

13. The method of claim 12, wherein the composition further comprises another amine or mixtures thereof.

14. The method of claim 12, wherein the composition comprises an organic solvent or mixtures thereof.

15. The method of claim 13, wherein the method further comprises a step of recovering the polynucleotide by elution with water, an aqueous buffer, or a chromatographic mobile phase.

16. The method of claim 13, wherein the step of removing and/or washing is performed by applying an inert gas, or a vacuum, and/or the step of removing and/or washing further comprises drying and/or evaporation.

17. A method of deprotecting a polynucleotide comprising one or more of the following nucleobases: U, $N^6$-benzoyl-A, $N^6$-isobutyryl-A, $N^6$—(N,N)-dimethylacetamidine-A, $N^6$—(N,N)-dibutylformamidine-A, $N^6$-phenoxyacetyl-A, $N^6$-4-tert-butylphenoxyacetyl-A, $N^4$-acetyl-C, $N^4$-isobutyryl-C, $N^4$-phenoxyacetyl-C, $N^4$-4-tert-butylphenoxyacetyl-C, $N^2$-isobutyryl-G, $N^2$—(N,N)-dibutylformamidine-G, $N^2$—(N,N)-dimethylformamidine-G, $N^2$-phenoxyacetyl-G and $N^2$-4-tert-butylphenoxyacetyl-G; and a ribonucleotide residue comprising a 2'-protecting group selected from tert-butyldimethylsilyl (TBDMS), triisopropylsilyloxymethyl (TOM) or 2'-O-bis(2-acetoxyethoxy)methyl (ACE), the method comprising:
   (a) contacting the polynucleotide with a first composition comprising a 2'-deprotection reagent, under conditions sufficient to remove said 2'-protecting group and produce a first deprotected polynucleotide; and
   (b) contacting the first deprotected polynucleotide with a second composition comprising a diamine, under conditions sufficient to remove said nucleobase protecting group and produce a fully deprotected polynucleotide.

* * * * *

SEQUENCE LISTING

<160> NUMBER OF SEQ ID NOS: 1

<210> SEQ ID NO 1
<211> LENGTH: 21
<212> TYPE: DNA
<213> ORGANISM: Artificial Sequence
<220> FEATURE:
<223> OTHER INFORMATION: Synthesized in a lab

<400> SEQUENCE: 1
gugucaguac agaugaggcc t         21